(12) United States Patent
Titball et al.

(10) Patent No.: US 9,573,981 B2
(45) Date of Patent: Feb. 21, 2017

(54) **EPSILON TOXIN EPITOPES FROM *CLOSTRIDIUM PERFRINGENS* WITH REDUCED TOXICITY**

(71) Applicant: UNIVERSITY OF EXETER, Exeter (GB)

(72) Inventors: Richard W. Titball, Exeter (GB); Monika Bokori-Brown, Exeter (GB); Claire Naylor, Exeter (GB)

(73) Assignee: University of Exeter, Exeter (GB)

( * ) Notice: Subject to any disclaimer, the term of this patent is extended or adjusted under 35 U.S.C. 154(b) by 0 days.

(21) Appl. No.: 14/387,809

(22) PCT Filed: Mar. 28, 2013

(86) PCT No.: PCT/GB2013/050821
§ 371 (c)(1),
(2) Date: Sep. 24, 2014

(87) PCT Pub. No.: WO2013/144636
PCT Pub. Date: Oct. 3, 2013

(65) Prior Publication Data
US 2015/0064207 A1    Mar. 5, 2015

(30) Foreign Application Priority Data

Mar. 29, 2012 (GB) .................................. 1205599.2
Apr. 5, 2012 (GB) .................................. 1206169.3

(51) Int. Cl.
*A61K 39/08* (2006.01)
*C07K 14/33* (2006.01)
(Continued)

(52) U.S. Cl.
CPC ............... *C07K 14/33* (2013.01); *A61K 39/08* (2013.01); *C07K 16/1282* (2013.01); *A61K 39/00* (2013.01)

(58) Field of Classification Search
CPC ......... A61K 39/00; A61K 39/08; A61K 38/00
(Continued)

(56) References Cited

U.S. PATENT DOCUMENTS

| 2010/0261884 | A1 | 10/2010 | Ainley et al. |
| 2011/0033501 | A1 | 2/2011 | Curtiss et al. |
| 2013/0183344 | A1* | 7/2013 | Garg ............ A61K 39/08 424/239.1 |

FOREIGN PATENT DOCUMENTS

| WO | 9323543 | 11/1993 |
| WO | 2008/148166 A1 | 12/2008 |

(Continued)

OTHER PUBLICATIONS

Yao, W et al, Apr. 6, 2016, Nature, Scientific Reports, pp. 1-7, Immunization with a novel Clostridium perfringens epsilon toxin mutant rETXy196E-C confers strong protection in mice.*

(Continued)

*Primary Examiner* — Albert Navarro
*Assistant Examiner* — Ginny Portner
(74) *Attorney, Agent, or Firm* — Dorsey & Whitney, LLP

(57) ABSTRACT

There is provided an epsilon toxin epitope polypeptide comprising a sequence of at least 10 contiguous amino acids from SEQ ID NO:3, the sequence comprising a mutation of at least one tyrosine residue compared to the equivalent sequence in SEQ ID NO:3, the polypeptide being capable of binding an antibody which binds to SEQ ID NO:5 and having reduced toxicity compared with the toxicity of SEQ ID NO:5. The polypeptide is useful in a method of vaccinating a subject against developing a disease caused by *clostridium perfringens* and/or caused by (or associated with the presence of) active epsilon toxin.

15 Claims, 8 Drawing Sheets

(51) Int. Cl.
*C07K 16/12* (2006.01)
*A61K 39/00* (2006.01)

(58) Field of Classification Search
USPC .............................. 424/247.1, 239.1, 184.1
See application file for complete search history.

(56) References Cited

FOREIGN PATENT DOCUMENTS

| WO | 2012/004645 | * | 1/2012 | ............ A61K 39/08 |
|---|---|---|---|---|
| WO | 2012004645 A1 | | 1/2012 | |
| WO | 2013061056 A1 | | 5/2013 | |

OTHER PUBLICATIONS

McClain, MS et al, Infection and Immunity, Apr. 2007, vol. 75(4), pp. 1745-1793, Functional Analysis of Neutralizing Antibodies against Clostridium perfringens Epsilon-Toxin.*
Popoff, Michel R. The FEBS Journal, Epsilon toxin:a fascinating pore forming toxin, vol. 278,pp. 4602-4615, 2011.*
Sakurai, Jun, Reviews in Medical Microbiology, 1995, vol. 6(3), pp. 175-185, Toxins of Clostridium perfringens.*
Ivie, Susan E et al, PLOS One, Gene-Trap Mutaenesis Idnetifies Mammalian Genes Contributing to Intoxication by Clostridium perfringens E-toxin, Mar. 2011, vol. 6(3), e17787, pp. 1-13.*
Pelish, TM et al, The Journal of Biological Chemistry, vol. 284(43), pp. 29446-29453, Oct. 23, 2009, Dominant Negative inhibitors of the Clostridium perfringens E-toxn.*
Ivie Susan E et al, Biochemistry, Sep. 25, 2012, vol. 51(38), pp. 7588-7595, Identification of Amino acids Important for Binding of Clostridium perfringens Epsilon Toxin to Host cells and to HAVCR1.*
Ellis, in Vaccines, 1988, WB Saunders Company, Chapter 29, New Technologies for Making Vaccines, pp. 568-575.*
Boslego, John W. et al, Chapter 17, Gonorrhea Vaccines, pp. 211-223, in Vaccines and Immunotherapy, 1991.*
Intellectual Property Office, Search Report under Section 17(5), Application No. GB1322463.9 dated Jan. 30, 2014, pp. 1-5.
International application No. GB2012/052369 third party observation dated Feb. 14, 2014, pp. 1-24.
International Search Report and Written Opinion for International Application No. PCT/GB2014/053748 dated Apr. 9, 2015, pp. 1-12.
PCT International Search Report dated Oct. 1, 2014 for International Application No. PCT/GB2013/050821, pp. 1-10.
PCT International Search Report dated Aug. 27, 2013 for International Application No. PCT/GB2013/050821, 3 pages.
PCT International Search Report and Written Opinion dated Mar. 1, 2013, PCT Application. No. PCT/GB2012/052639, 69 pages.
Abildgaard, et al., "In Vitro Production of Necrotic Enteritis Toxin B, by NetB-Positive and NetB-Negative Clostridium Perfringens Originating from Healthy and Diseased Broiler Chickens", Veterinary Microbiology, Elsevier BV, NL, vol. 144, No. 1-2, Jul. 29, 2010, pp. 231-235.
Abrami, et al., "Plasma Membrane Microdomains Act as Concentration Platforms to Facilitate Intoxication by Aerolysin", The Journal of Cell Biology, vol. 147, No. 1, Oct. 4, 1999, pp. 175-184.
Adams, et al., "Phenix: a comprehensive Python-based system for macromolecular structure solution", Acta Cryst., (2010), pp. 213-221.
Akiba, et al., "Crystal Structure of the Parasporin-2 Bacillus thuringiensis Toxin That Recognizes Cancer Cells", J. Mol. Biol., 386, (2009), pp. 121-133.
Battye, et al., "iMOSFLM: a new graphical interface for diffraction-image processing with MOSFLM", Acta Cryst., D67, (2011), pp. 271-281.
Bhown, et al., "Structural Studies on ϵ-Prototoxin of Clostridium Perfringens Type D: Location of the Site of Tryptic Scission Necessary for Activation to ϵ-Toxin, Academic Press", Inc., Biochemical and Biophysical Research Communications, vol. 78, (1977), pp. 1-8.
Bokori-Brown, et al., "Clostridium perfringens epsilon toxin H149A mutant as a platform for receptor binding studies", Protein Science, vol. 22, No. 5, May 8, 2013, pp. 650-659.
Bokori-Brown, et al., "Molecular basis of toxicity of Clostridium perfringens epsilon toxin", The FEBS Journal 278, (2011), pp. 4589-4601.
Chassin, et al., "Pre-forming epsilon toxin causes membrane permeabilization and rapid ATP depletion-mediated cell death in renal collecting duct cells", Am. J. Physiol. Renal Physiol 293, (2007), pp. F927-F937.
Cole, et al., "Clostridium perfringens ϵ-toxin shows structural similarity to the pore-forming toxin aerolysin", Nature Structural & Molecular Biology, vol. 11, No. 8, Aug. 2004, pp. 1-2.
Cooper, et al., "Immunization with recombinant alpha toxin partially protects broiler chicks against experimental challenge with Clostridium perfringens", Veterinary Microbiology, 133, (2009), pp. 92-97.
Cooper, et al., "Virulence of Clostridium perfringens in an experimental model of poultry necrotic enteritis", Veterinary Microbiology, 142, (2010), pp. 323-328.
Crouch, C. F. et al., "Safety and efficacy of a maternal vaccine for the passive protection of broiler chickens against necrotic enteritis", Avian Pathology, 39:6, Dec. 10, 2010, pp. 489-497.
Davis, et al., "MolProbity: all-atom contacts and structure validation for proteins and nucleic acids", Nucleic Acids Research, (2007), vol. 35, pp. W375-W383.
Elmsley, et al., "Features and development of Coot", Acta Cryst. (2010). D66, pp. 486-501.
Evans, "Scaling and assessment of data quality", Acta Cryst. (2006). D62, pp. 72-82.
Fernandes Da Costa, et al., "Protection against avian necrotic enteritis after immunisation with NetB genetic or formaldehyde", Vaccine 31, (2013), pp. 4003-4008.
Finnie, "Pathogenesis of brain damage produced in sheep by Clostridium perfringens type D epsilon toxin: a review", Aust Vet J, vol. 81, No. 4, Apr. 2003, pp. 219-221.
Gholamiandehkordi, Ahmad R. et al., "Quantification of gut lesions in a subclinical necrotic enteritis model", Avian Pathology, Oct. 2007, 36(5), pp. 375-382.
Gholamiandekhordi, et al., "Molecular and phenotypical characterization of Clostridium perfringens isolates from poultry flocks with different disease status", Veterinary Microbiology, 113, (2006), pp. 143-152.
Gill, "Bacterial Toxins: a Table of Lethal Amounts", Microbiological Reviews, vol. 46, No. 1, Mar. 1982, pp. 86-94.
Hunter, et al., "Cloning and Nucleotide Sequencing of the Clostridium perfringens Epsilon-Toxin Gene and Its Expression in *Escherichia coli*", Infection and Immunity, vol. 60, No. 1, Jan. 1992, pp. 102-110.
Kaldhusdal, et al., "Necrotic enteritis challenge models with broiler chickens raised on litter: evaluation of preconditions, Clostridium perfringens strains and outcome variables", FEMS Immunology and Medical Microbiology, 24, (1999), pp. 337-343.
Keyburn, et al., "Alpha-Toxin of Clostridium perfringens Is Not an Essential Virulence Factor in Necrotic Enteritis in Chickens", Infect. Immun., (2006), 74(11), p. 6496.
Keyburn, et al., "NetB, a New Toxin That Is Associated with Avian Necrotic Enteritis Caused by Clostridium perfringens", PLoS Pathog, (2008), 4(2), p. e26.
Keyburn, et al., "NetB, a Pore-Forming Toxin from Necrotic Enteritis Strains of Clostridium Perfringens", Toxins, vol. 2, No. 7, Jul. 2010, pp. 1913-1927.
Keyburn, Anthony L. et al., "Maternal immunization with vaccines containing recombinant NetB toxin partially protects progeny chickens from necrotic enteritis", Veterinary Research, (2013), 44:108, pp. 1-7.
Keyburn, Anthony L. et al., "Vaccination with recombinant NetB toxin partially protects broiler chickens from necrotic enteritis", Veterinary Research, (2013), 44:54, pp. 1-8.

(56) References Cited

OTHER PUBLICATIONS

Knight, et al., "In Vitro Tests for the Measurement of Clostridial Toxins, Toxoids and Antisera II. Titration of Clostridium Perfingens Toxins and Antitoxins in Cell Culture", Biologicals, (1990), 18, pp. 263-270.
Kulkarni, et al., "A Live Oral Recombinant *Salmonella* enterica Serovar Typhimurium Vaccine Expressing Clostridium perfringens Antigens Confers Protection against Necrotic Enteritis in Broiler Chickens", Clinical and Vaccine Immunology, vol. 17(2), Feb. 2010, pp. 205-214.
Kulkarni, et al., "Immunization of Broiler Chickens against Clostridium perfringens-Induced Necrotic Enteritis", Clin. Vaccine Immunol., (2007), 14(9):1070.
Kulkarni, et al., "Oral immunization of broiler chickens against necrotic enteritis with an attenuated *Salmonella* vaccine nector expressing Clostridium perfringens antigens", Vaccine, 26, (2008), pp. 4194-4203.
MacKenzie, et al., "Analysis of Receptor Binding by the Channel-forming Toxin Aerolysin Using Surface Plasmon Resonance", J. Biol. Chem., (1999), 274, pp. 22604-22609.
Mancheno, et al., "Structural Analysis of the Laetiporus sulphureus Hemolytic Pore- forming Lectin in Complex with Sugars", J. Biol. Chem., (2005), 280, pp. 17251-17259.
Manich, et al., "Clostridium perfringens Delta Toxin Is Sequence Related to Beta Toxin, NetB, and *Staphylococcus* Pore-Forming Toxins, but Shows Functional Differences", PLoS One , (2008), 3(11): e3764.
McCoy, et al., "Phaser crystallographic software", J. Appl. Cryst., (2007), 40, pp. 658-674.
McDonel, "Clostridium perfringens Toxins (Type A, B, C, D, E)", Pharmac. Ther., (1980), vol. 10, pp. 617-655.
McDonel, James L. , "Toxins of Clostridium Perfringens Types A, B,C, and E", Chapter 22, Pharmacology of Bacterial Toxins, Dorner & Drew, Pergamon Press, (1986), pp. 477-517.
Minami, et al., "Lambda-Toxin of Clostridium perfringens Activates the Precursor of Epsilon-Toxin by Releasing Its N- and C-Terminal Peptides", Microbiol. Immunol., 41(7), (1997), pp. 527-535.
Needleman, et al., "A General Method Applicable to the Search for Similarities in the Amino Acid Sequence of Two Proteins", J. Mol. Biol., (1970), 48, pp. 443-453.
Oyston, et al., "Production of a non-toxic site-directed mutant of Clostridium perfringens epsilon-toxin which induces protective immunity in mice", Microbiology, vol. 144, No. 2, Feb. 1, 1998, pp. 333-341.
Parker, Michael W. et al., "Structure of the Aeromonas toxin proaerolysin in its water-soluble and membrane-channel states", Nature, vol. 367, Jan. 20, 1994, pp. 1-4.
Payne, Dean et al., "The Clostridium perfringens epsilon-toxin", Reviews In Medical Microbiology, (1997), 8 (Suppl 1), S28-S30, pp. 1-3.
Payne, Dean W. et al., "Evaluation of a new cytotoxicity assay for Clostridium perfringens type D epsilon toxin", FEMS Microbiol., (1994), Lett. vol. 116, pp. 161-167.
Pelish, Teal M. et al., "Dominant-negative inhibitors of the Clostridium perfringens epsilon-toxin", Journal of Biological Chemistry, vol. 284, No. 43, 23, Oct. 23, 2009, pp. 29446-29453.
Petit, et al., "Clostridium perfringens: toxinotype and genotype", Elsevier Science, (1999).
Petit, Laetitia et al., "Clostridium perfingens Epsilon Toxin Induces a Rapid Change of Cell Membrane Permeability to Ions and Forms Channels in Artficial Lipid Bilayers", The Journal of Biological Chemistry, vol. 276, No. 19, May 11, 2001, pp. 15736-15740.
Petit, Laetitia et al., "Clostridium perfringens Epsilon-Toxin Acts on MDCK Cells by Forming a Large Membrane Complex", Journal of Bacteriology, Oct. 1997, pp. 6480-6487.
Petit, Laetitia et al., "Clostridium perfringens: toxinotype and genotype", Trends in Microbiology, Mar. 1999, vol. 7. No. 3, pp. 104-110.
Rood, Julian I. , "Virulence Genes of Clostridium Perfringens", Anny. Rev. Microbiol., (1998), 52, pp. 333-360.
Sakurai, Jun et al., "The Inactivation of Clostridium Perfringens Epsilon Toxin by Treatment With Tetranitromethane an N-Acetylimidazole", Taxicon, vol. 25, No. 3, (1987), pp. 279-284.
Sambrook, et al., "Chapter 15: Expression of Cloned Genes", Molecular Cloning: A Laboratory Manual. Cold Spring Harbor Laboratory Press, 2001, pp. 15.1-15.29.
Sambrook, et al., "Protocol 8: Hybridization of Oligonucleotide Probes in Aqueous Solutions: Washing in Buffers Containing Quaternary Ammonium Salts", Molecular Cloning: A Laboratory Manual. Cold Spring Harbor Laboratory Press, (2001), pp. 10.35-10.37.
Sambrook, et al., "Protocol 8: Tetracycline as Regulator of Inducible Gene Expression in Mammalian Cells", Molecular Cloning: A Laboratory Manual. Cold Spring Harbor Laboratory Press, (2001), pp. 17.52-17.99.
Savva, et al., "Molecular Architecture and Functional Analysis of NetB, a Pore-Forming Toxin from Clostridium Perfringens", Journal of Biological Chemistry, vol. 288, No. 5, Feb. 1, 2013, pp. 3512-3522.
Shimamoto, Seiko et al., "Changes in Ganglioside Content Affect the Binding of Clostridium perfringens Epsilon-Toxin to Detergent-Resistant Membranes of Madin-Darby Canine Kidney Cells", Microbiol. Immunol., 49(3), (2005), pp. 245-253.
Shortt, SJ et al., "An assessment of the in vitro toxicology of Clostridium perfringens type D E-toxin in human and animal cells", Human & Experimental Toxicology, (2000), 19, pp. 108-116.
Smart, et al., "Exploiting structure similarity in refinement: automated NCS and target-structure restraints in Buster", Acta Cryst. (2012). D68, pp. 368-380.
Song, et al., "Structure of Staphylococcal a-Hemolysin, a Heptameric Transmembrane Pore", Science, New Series, vol. 274, No. 5294, Dec. 13, 1996, pp. 1859-1866.
Songer, "Clostridial Enteric Diseases of Domestic Animals", Clinical Microbiology Reviews, vol. 9(2), Apr. 1996, pp. 216-234.
Studier, F. W., "Protein production by auto-induction in high-density shaking cultures", Protein Expression and Purification 41, (2005), pp. 207-234.
Unknown, "Biological and Chemical Terrorism: Strategic Plan for Preparedness and Response", Centers for Disease Control and Prevention. Recoomendations of the CDC Strategic Planning Workgroup. MMWR, (2000); 49(No. RR-4), 26 pages.
Worthington, R.W. et al., "Physical Changes in the Epsilon Prototoxin Molecule of Clostridium perfringens During Enzymatic Activation", Infection and Immunity, Nov. 1977, vol. 18, No. 2, pp. 549-551.
Zekarias, et al., "Recombinant Attenuated *Salmonella* enterica Serovar Typhimurium Expressing the Carboxy-Terminal Domain of Alpha Toxin from Clostridium perfringens Induces Protective Responses against Necrotic Enteritis in Chickens", Clinical and Vaccine Immunology, vol. 15(5), May 2008, pp. 805-816.

\* cited by examiner

| PelB | Activated toxin | C-terminal peptide | His |

1　　　　　　　　25　　　　　　　　　　　　　　H149A　　　　　　　285　　　　315

MKYLLPTAAAGLLLLAAQPAMAMGKASYDNVDTL...　　　　　...EYVIPVDKKEKS............H

↑ Periplasmic signal peptidase　　　　　　　　　　↑ Trypsin

EPSILON TOXIN EPITOPES FROM *CLOSTRIDIUM PERFRINGENS* WITH REDUCED TOXICITY

This application is a national stage application under 35 U.S.C. §371 of International Application No. PCT/GB2013/050821, filed Mar. 28, 2013, entitled "EPSILON TOXIN EPITOPES FROM CLOSTRIDIUM PERFRINGENS WITH REDUCED TOXICITY," which claims priority to European Patent Application No. 1205599.2, filed Mar. 29, 2012 and European Patent Application No. 1206169.3, filed Apr. 5, 2012

FIELD OF THE INVENTION

The invention relates to novel polypeptides useful as a vaccine against diseases caused by or associated with the epsilon toxin of *Clostridium perfringens*, particularly in animals susceptible to development of enterotoxemia.

BACKGROUND

The rod-shaped, spore-forming, Gram-negative, anaerobe bacterium *Clostridium perfringens* is able to produce at least 17 toxins, making *C. perfringens* one of the most pathogenic species in the *Clostridium* genus. Depending on its ability to produce the four typing toxins, namely α-, β-, ε-, and ι-toxin, *C. perfringens* strains are classified into one of five toxinotypes, referred to as types A-E (Petit et al. (1999) Trends Microbiol. vol. 7, 104-110).

In addition to the typing toxins, the bacterium is able to produce a variety of so called minor toxins such as β1, β2, δ, θ, λ, μ, ν, and enterotoxin (Rood (1998) Annu. Rev. Microbiol. vol. 52, 333-360). Epsilon toxin (Etx) is produced by toxinotypes B and D. These strains are responsible for a severe disease called enterotoxemia, which affects predominantly sheep and lambs but also causes infections in other ruminant species, including goats and calves (Songer (1996) Clin. Microbiol. Rev. vol. 9, 216-234). Enterotoxemia in naturally infected animals is usually characterised by systemic lesions in sheep and enterocolitis in goats.

The most important factor in initiating disease is overeating rich food, resulting in the presence of high amounts of carbohydrates in the intestine. This leads to disruption of the microbial balance in the gut, leading to proliferation of *C. perfringens* and consequent overproduction of Etx. The toxin causes an increase in intestinal permeability, facilitating its entry into the bloodstream and allowing its dissemination to the main target organs of the kidneys and the brain (McDonel (1980) Pharmacol Ther 10(3): 617-655). Here, intoxication results in fluid accumulation due to increased permeability of blood vessels. Accumulation in the central nervous system results in neurological disorder rapidly leading to death (Finnie (2003) Aust. Vet. J. vol. 81, 219-221).

Etx is expressed with a signal sequence that directs export of the prototoxin from the bacterium (McDonel (1986) in *Pharmacology of bacterial toxins* eds. Dorner & Drew, Pergamon Press, 477-517). In development of disease, the relatively inactive prototoxin is converted to the active toxin by proteolytic cleavage in the gut lumen, either by digestive proteases of the host, such as trypsin and chymotrypsin (Bhown & Habeerb (1977) Biochem. Biophys. Res. Commun. vol. 78, 889-896), or by *C. perfringens* λ-protease (Minami et al. (1997) Microbiol. Immun. vol. 41, 527-535). Proteolytic activation of Etx can also be achieved in vitro by controlled proteolysis (Hunter et al. (1992) Infect. Immun. vol. 60, 102-110). Depending on the protease, proteolytic cleavage results in the removal of 10-13 amino-terminal and 22-29 carboxy-terminal amino acids (Bhown & Habeerb (1977); Minami et al. (1997)). Maximal activation occurs when both N- and C-termini are cleaved (Worthington & Mulders (1977) Infect. Immun. vol. 18, 549-551).

The 3D structure of Etx has been determined (Cole et al. (2004) Nature Structural & Molecular Biology vol. 11, 797-798) and reveals a molecule composed mainly of β-sheets, which can be divided into three functional domains. Domain I at the N-terminus contains the suggested receptor interaction region. Domain II in the middle contains an amphipathic β-hairpin, which is predicted to play a role in membrane insertion. Domain III at the C-terminus contains the C-terminal peptide, which has to be removed for activation to occur.

Epsilon toxin is an aerolysin-like β-pore forming toxin (β-PFT), with the amphipathic β-hairpin loops inserting into the membrane to form β-barrel structures. The overall fold of Etx shows similarity to the structure of aerolysin from the Gram-negative bacterium *Aeromonas hydrophila* (Parler et al. (1994) Nature vol. 367, 292-295), to parasporin-2 (PS) from *Bacillus thuringiensis* (Akiba et al. (2009) J. Mol. Biol. vol. 386, 121-133) and to a pore-forming lectin, LSL, from *Laetiporus sulphurous* (Mancheno et al. (2005) J. Biol. Chem. vol. 280, 17251-17259). The structural similarities between these toxins are most striking in their two C-terminal domains. Their N-terminal domains show a greater structural variation, which is likely to account for their differences in target cell specificities and potencies (Bokori-Brown et al. (2011) FEBS J. vol. 278, 4589-4601).

In aerolysin, the two amino-terminal domains (Domains I-II) are thought to play a role in binding to cell surfaces with overlapping functions (MacKenzie et al. (1999) J. Biol. Chem. vol, 274, 22604-22609) and it has been suggested that domain I of Etx, which is equivalent to domain II of aerolysin, performs a similar function (Cole et al. (2004)), but this has yet to be demonstrated. Domain II of aerolysin contains the mannose 6-phosphate binding loops. However, the residues of domain II involved in mannose-6-phosphate binding in aerolysin are not conserved in domain I of Etx, suggesting that the structural variation in the N-terminal receptor binding domains of these toxins is likely to account for the differences between their target cell specificities.

Etx is unique among β-PFTs because it is highly potent and has high cell specificity. Because of its high potency, Etx is considered to be a potential biological weapon for international terrorism by the U.S. Government Centres for Disease Control and Prevention (Morbidity and Mortality Weekly Report (MMWR) Recommendations and Reports (2000) vol. 49, 1-14). The 50% lethal dose ($LD_{50}$) of Etx in mice after intravenal injection is typically 100 ng/kg (Gill (1982) Microbiol. Rev. vol. 46, 86-94), making Etx the most potent clostridial toxin after botulinum neurotoxin. Etx also shows high cell specificity. Among the many cell lines tested, only four have been identified to be susceptible to the toxin. These include kidney cell lines of dog (MDCK (Knight et al. (1990) Biologicals vol. 18, 263-270)), mouse (mpkCCDc14 (Chassin et al. (2007) Am. J. Physiol. Renal Physiol. vol. 293, F927-937)) and human (G-402 (Shortt et al. (2000) Hum. Exp. Toxicol. vol. 19, 108-116) and ACHN (Ivie et al. (2011) PloS ONE vol. 6, e17787)) origin. Most in vitro studies on Etx have been carried out using the Madin-Darby Canine Kidney (MDCK) cell line, as this cell line is the most susceptible to the toxin (Payne et al. (1994)

FEMS Microbiol. Lett. vol. 116, 161-167). The dose of Etx to kill 50% of MDCK cells ($CT_{50}$) is reported to be as low as 15 ng/ml.

The binding of Etx to MDCK cells is associated with the formation of a stable, high molecular weight complex (Petit et al. (1997) J. Bacteriol. vol. 179, 6480-6487). Intoxicated cells undergo morphological changes that include swelling and membrane blebbing before cell death (Petit et al. (1997) J. Bacteriol. vol. 179, 6480-6487). The rapid toxin-induced cell death and the specificity of epsilon toxin for only a few cell lines suggest the presence of a specific receptor(s) on target cells. The mechanism of Etx binding to cells is not known, but chemical modification studies of Etx have previously indicated that a tyrosine residue is necessary for binding of the toxin to target cells (Sakurai & Nagahama (1987) Toxicon vol. 25, 279-284). Toxicity appears to be a consequence of the formation of pores in the target cell membrane (Petit et al. (2001) J. Biol. Chem. vol. 276, 15736-15740).

Since progression of enterotoxemia from onset to death can be rapid in agricultural animals and given the potential for Etx to be used as a biological weapon, there is a need to identify molecules with potential for use as a vaccine against disease caused by or associated with the presence of Etx and/or caused by infection by C. perfringens.

SUMMARY OF INVENTION

According to a first aspect of the invention, there is provided an epsilon toxin epitope polypeptide comprising a sequence of at least 10 contiguous amino acids from SEQ ID NO:3, the contiguous sequence comprising a mutation of at least one tyrosine residue compared to the equivalent sequence in SEQ ID NO:3, the polypeptide being capable of binding an antibody which binds to SEQ ID NO:5 (activated wild-type C. perfringens epsilon toxin) and/or SEQ ID NO:22 (a reduced toxicity variant of SEQ ID NO:5) and having reduced toxicity compared with the toxicity of SEQ ID NO:5.

As stated in Table 3 below, SEQ ID NO:2 is full length wild type C. perfringens epsilon toxin and SEQ ID NO:3 is the same sequence, but lacking the first 32 amino acids. This sequence SEQ ID NO:3 is the sequence published for the crystal structure (see the Research Collaboratory for Structural Bioinformatics (RCSB) databank at www.rcsb.org/pdb; PDB ID: 1UYJ) and numbering of tyrosine residues referred to herein is on the basis of this sequence. SEQ ID NO:1 shows 100% sequence identity to SEQ ID NO:3 from SEQ ID NO:1 residue 33 onwards. Therefore, SEQ ID NOs:1 and 3 have 90% identity at the global alignment level, when determined as outlined below.

As mentioned above, SEQ ID NO:5 is activated wild type C. perfringens epsilon toxin which remains after protease cleavage, with N- and C-termini removed. SEQ ID NOs:2 and 5 have 80% identity at the global alignment level, when determined as outlined below.

SEQ ID NO:22 is a sequence equivalent to SEQ ID NO:5 but with a H>A mutation at position 151 of SEQ ID NO:5 (mentioned in the Examples below as the H149A mutation, with the difference in residue numbering explained below). This is a variant of the activated toxin which may be studied in the laboratory at ACGM level 2 (Oyston et al. (1998) Microbiol. vol. 144 (Pt 2), 333-341) and so may be more convenient practically for determining antibody binding.

The polypeptide according to the invention may include a sequence of at least 15, 20, 25, 30, 35, 40, 45, 50, 60, 70, 80, 90 or 100 contiguous amino acids from SEQ ID NO:3, the sequence comprising a mutation of at least one tyrosine residue compared to the equivalent sequence in SEQ ID NO:3. The inclusion of a mutation within the contiguous amino acid sequence has the result that the sequence included in the polypeptide is identical to the equivalent sequence from SEQ ID NO:3, apart from a tyrosine amino acid in at least one of the positions within that sequence being substituted for a different amino acid. That is, the sequences are identical apart from at the mutated position(s). Preferably, the contiguous amino acid sequence from SEQ ID NO:3 is also found in SEQ ID NO:5.

In some embodiments, where the contiguous amino acid sequence from SEQ ID NO:3 comprises position 162 of SEQ ID NO:3, the amino acid at this position is mutated to one other than the histamine found in SEQ ID NO:3. For example, it may be substituted by alanine. This is the H149A mutation described elsewhere herein and its inclusion would doubly ensure that the polypeptide according to the invention could be used at ACGM level 2.

The level of toxicity may be determined as described herein, for example by use of a MDCK.2 cell-based LDH assay. The polypeptides of the invention provide protection, when administered to a subject such as a lamb, to the subject from developing a disease (such as enterotoxemia) caused by infection by Clostridium perfringens and/or caused by the presence of active epsilon toxin (or associated with the presence of the toxin). Such protection may be partial, whereby the probability of an individual subject within a population of developing disease is reduced, or complete, whereby the subject will not develop disease (i.e., the probability of developing disease caused by C. perfringens and/or by Etx is 0%).

The term "epsilon toxin epitope polypeptide" as used herein means a polypeptide which comprises one or more (or all) epitopes of mature activated wild-type epsilon toxin ("active toxin"), as represented by SEQ ID NO:5. The term "epitope" refers to the amino acids (typically a group of around 5 or more amino acids) within a polypeptide sequence which are essential in the generation of an immune response. These amino acids can be consecutive in the sequence but, more typically, are non-consecutive, grouping together when the tertiary structure of the native protein is formed. Provided that these amino acids are within a polypeptide environment which enables them to form the correct epitopic tertiary structure, they can be used to provide a protective vaccine composition. For example, an epsilon toxin epitope polypeptide may be one which is capable of binding to an antibody which binds to the mature activated wild-type epsilon toxin having sequence SEQ ID NO:5 and/or to the low-toxicity variant sequence SEQ ID NO:22.

In the present study, the inventors investigated the role of domain I of Etx in cell binding, to identify the key residues involved in this. This allowed them to determine the requirement for toxicity. For this, they generated site directed mutants by replacing tyrosine residues with alanine. Cytotoxicity and binding studies of these single tyrosine mutants indicated that a cluster of surface exposed tyrosines in domain I is critical for the interaction of Etx with the receptor on MDCK.2 cells. Reduced cytotoxicity of the mutants correlated with their reduced ability to bind to MDCK.2 cells. To further evaluate the roles of tyrosine residues in receptor binding, the inventors generated a double tyrosine mutant of Etx, Y43A/Y209A. Replacement of Y43 and Y209 with alanine resulted in cytotoxicity equivalent to that of inactive wild-type prototoxin, indicating that Y43A/Y209A is inactive. This apparent loss of cytotoxic activity related to the inability of Y43A/Y209A to bind to MDCK.2 cells.

Therefore, the mutated tyrosine residue in the epsilon toxin epitope polypeptide of the invention may be one or more within loop 1 (residues K32-I55, residue number according to equivalent positions in SEQ ID NO:3, as explained above) or loop 2 (S201-S220) of domain I of Etx. The mutated tyrosine residue may be, for example, one or more of Y29, Y33, Y42, Y43, Y49 and/or Y209, residue numbering being according to the equivalent positions in SEQ ID NO:3. In a particular embodiment, the polypeptide comprises mutation of two tyrosine residues compared to SEQ ID NO:3, Y43 and Y209. The polypeptide may comprise an alanine at each of these residue positions. Alternatively or additionally to the ability to bind an antibody which binds to SEQ ID NO:5 and/or SEQ ID NO:22, the polypeptide may bind an antibody which binds to SEQ ID NO:2, the non-activated prototoxin form of the epsilon toxin.

The polypeptide according to the invention may comprise the amino acid sequence RMEKYXPNAM (SEQ ID NO:33) and/or the amino acid sequence YNYLKRMEKYXPNA-MAYFDK (SEQ ID NO:34), wherein "X" is any amino acid other than Y. The polypeptide according to the invention may comprise the amino acid sequence GEIPSXLAFP (SEQ ID NO:35) and/or the amino acid sequence SGSEWGEIPSXLAFPRDGYK (SEQ ID NO:36), wherein "X" is any amino acid other than Y. "X" may be amino acid alanine. The polypeptide according to the invention may comprise all of SEQ ID NOs:33-36.

The polypeptide according to the invention may form part of a fusion protein. The polypeptide may have at least about 60% sequence identity to SEQ ID NO:6 (activated toxin sequence comprising Y43A and Y209A mutations) or SEQ ID NO:25 (activated recombinant toxin comprising Y43A, Y209A and H149A mutations) and comprising a mutation at position 43 and position 209 (as compared to the equivalent positions in SEQ ID NO:3), such that a tyrosine residue at each of those positions is replaced by another amino acid such as alanine. That is, the polypeptide is at least about 60% identical to SEQ ID NO:6 (or SEQ ID NO:25) and comprises any amino acid other than tyrosine at the position equivalent to positions 32 and 198 of SEQ ID NO:6 (or positions 32 and 198 of SEQ ID NO:25), when aligned with SEQ ID NO:6 (or SEQ ID NO:25) using a global sequence alignment tool as described below. In another embodiment, the polypeptide according to the invention comprises an amino acid sequence at least about 60% identical to SEQ ID NO:1 (full-length wild type toxin sequence) and comprising a mutation at position 43 and position 209 (as compared to the equivalent positions in SEQ ID NO:3), such that a tyrosine residue at each of those positions is replaced by another amino acid such as alanine. That is, the polypeptide is at least about 60% identical to SEQ ID NO:1 and comprises any amino acid other than tyrosine at the position equivalent to positions 75 and 241 of SEQ ID NO:1, when aligned with SEQ ID NO:1 using a global sequence alignment tool as described below.

The polypeptide may have equal or similar toxicity to SEQ ID NO:22 and/or be non-toxic.

The polypeptide may have at least about 60%, 65%, 70%, 75%, 80%, 85%, 90%, 91%, 92%, 93%, 94%, 95%, 96%, 97%, 98% or about 99% sequence identity to SEQ ID NOs:1, 4, 6, 15, 19 or 25. The epsilon toxin epitope polypeptide may consist of or may comprise an amino acid sequence selected from SEQ ID NOs:1, 4, 6, 15, 19 or 25 (i.e., sequences comprising at least the Y43A and Y209A mutations, some also comprising the H149A mutation).

As outlined further below, sequence identity may be determined using the Needleman-Wunsch Global Sequence Alignment Tool available from the National Center for Biotechnology Information (NCBI), Bethesda, Maryland, USA, for example at blast.ncbi.nlm.nih.gov/Blast.cgi, using default parameter settings. When comparing the level of sequence identity to (for example) SEQ ID NO:6, this typically should be done relative to the whole length of SEQ ID NO:6, to avoid short regions of high identity overlap resulting in a high overall assessment of identity (i.e., a global alignment method is used). For example, a short polypeptide fragment having, for example, five amino acids might have a 100% identical sequence to a five amino acid region within the whole of SEQ ID NO:6, but this does not provide a 100% amino acid identity unless the fragment forms part of a longer sequence which also has identical amino acids at the other positions equivalent to positions in SEQ ID NO:6.

Therefore, the skilled person is readily able to determine equivalent positions between two sequences, by aligning sequences to achieve maximum identical amino acids at as many positions as possible, for example by using a global sequence alignment program such as is available at blast.ncbi.nlm.nih.gov/Blast.cgi, discussed further below.

An epitope polypeptide according to the invention may be, as mentioned above, any which comprises at least one epitope of epsilon toxin and is capable of binding an antibody which will bind to a polypeptide having sequence SEQ ID NO:5 and/or 22.

Therefore, the polypeptide may be as little as about 20 amino acids in length provided that it still binds to such an antibody, for example, it may be at least about 30, 40, 50, 70, 90, 120, 150 or about 170 amino acids in length. In some embodiments, the polypeptide may be at least about 190 amino acids in length, for example, it may be between 190 and 360 amino acids in length, such as between 200-350, 220-340 or 250-330 in length. In some embodiments, the polypeptide may be at least about 200 amino acids in length, for example, at least about 220, 230, 240, 250, 260, 270, 280, 290, 300, 310, 320 or about 330 amino acids in length. In certain specific embodiments, the polypeptide may be 263, 293, 315 or 328 amino acids in length (the lengths of SEQ ID NO:6, 28, 15 and 1, respectively).

The present invention also encompasses polypeptides comprising variants of the epitope polypeptides and methods utilising these variant polypeptides. As used herein, a "variant" means a polypeptide in which the amino acid sequence differs from the base sequence from which it is derived in that one or more amino acids within the sequence are substituted for other amino acids. The variant is a functional variant, in that the functional characteristics of the polypeptide from which the variant is derived are maintained. For example, the variant polypeptide may have a similar ability to bind an antibody capable of binding to a non-variant polypeptide (such as, by way of non-limiting example, SEQ ID NOs:1, 4, 6, 15, 19, 25). In particular, any amino acid substitutions, additions or deletions must not alter or significantly alter the tertiary structure of one or more epitopes contained within the polypeptide from which the variant is derived, so that the variant polypeptide retains the ability to bind to an antibody which binds to SEQ ID NO:5 or 22. The skilled person is readily able to determine appropriate functional variants and to determine the tertiary structure of an epitope and any alterations thereof, without the application of inventive skill.

Amino acid substitutions may be regarded as "conservative" where an amino acid is replaced with a different amino acid with broadly similar properties. Non-conservative substitutions are where amino acids are replaced with amino acids of a different type.

By "conservative substitution" is meant the substitution of an amino acid by another amino acid of the same class, in which the classes are defined as follows:

| Class | Amino acid examples |
| --- | --- |
| Nonpolar: | Ala, Val, Leu, Ile, Pro, Met, Phe, Trp |
| Uncharged polar: | Gly, Ser, Thr, Cys, Tyr, Asn, Gln |
| Acidic: | Asp, Glu |
| Basic: | Lys, Arg, His. |

As is well known to those skilled in the art, altering the primary structure of a polypeptide by a conservative substitution may not significantly alter the activity of that polypeptide because the side-chain of the amino acid which is inserted into the sequence may be able to form similar bonds and contacts as the side chain of the amino acid which has been substituted out. This is so even when the substitution is in a region which is critical in determining the polypeptide's conformation.

As mentioned above, non-conservative substitutions are possible provided that these do not disrupt the tertiary structure of an epitope within the polypeptide, for example, which do not interrupt the immunogenicity (for example, the antigenicity) of the polypeptide.

Broadly speaking, fewer non-conservative substitutions will be possible without altering the biological activity of the polypeptide. As mentioned above, variants may suitably be at least about 60% identical to the base sequence.

As already briefly mentioned, sequence identity between amino acid sequences can be determined by comparing an alignment of the sequences. When an equivalent position in the compared sequences is occupied by the same amino acid, then the molecules are identical at that position. Scoring an alignment as a percentage of identity is a function of the number of identical amino acids at positions shared by the compared sequences. When comparing sequences, optimal alignments may require gaps to be introduced into one or more of the sequences, to take into consideration possible insertions and deletions in the sequences. Sequence comparison methods may employ gap penalties so that, for the same number of identical molecules in sequences being compared, a sequence alignment with as few gaps as possible, reflecting higher relatedness between the two compared sequences, will achieve a higher score than one with many gaps. Calculation of maximum percent identity involves the production of an optimal alignment, taking into consideration gap penalties. As mentioned above, the percentage sequence identity may be determined using the Needleman-Wunsch Global Sequence Alignment tool, publicly available at blast.ncbi.nlm.nih.gov/Blast.cgi, using default parameter settings. The Needleman-Wunsch algorithm was published in J. Mol. Biol. (1970) vol. 48:443-53.

A further aspect of the invention provides a polynucleotide having a nucleic acid sequence which encodes for a polypeptide according to the first aspect of the invention. Examples are provided herein as SEQ ID NOs:55-60, which encode amino acid sequences SEQ ID NOs: 1, 4, 6, 15, 19 and 25, respectively, as shown in Table 4. The invention also encompasses variant nucleic acids encoding the polypeptides of the invention. The term "variant" in relation to a nucleic acid sequence means any substitution of, variation of, modification of, deletion of, or addition of one or more nucleic acid(s) from or to a polynucleotide sequence, providing the resultant polypeptide sequence encoded by the polynucleotide exhibits at least the same properties as the polypeptide encoded by the basic sequence. The term therefore includes allelic variants and also includes a polynucleotide (a "probe sequence") which substantially hybridises to the polynucleotide sequence of the present invention. Such hybridisation may occur at or between low and high stringency conditions. In general terms, low stringency conditions can be defined as hybridisation in which the washing step takes place in a 0.330-0.825 M NaCl buffer solution at a temperature of about 40-48° C. below the calculated or actual melting temperature ($T_m$) of the probe sequence (for example, about ambient laboratory temperature to about 55° C.), while high stringency conditions involve a wash in a 0.0165-0.0330 M NaCl buffer solution at a temperature of about 5-10° C. below the calculated or actual $T_m$ of the probe sequence (for example, about 65° C.). The buffer solution may, for example, be SSC buffer (0.15M NaCl and 0.015M tri-sodium citrate), with the low stringency wash taking place in 3×SSC buffer and the high stringency wash taking place in 0.1×SSC buffer. Steps involved in hybridisation of nucleic acid sequences have been described for example in Sambrook et al. (2001; "Molecular Cloning: a laboratory manual", $3^{rd}$ Edition, Cold Spring Harbor Laboratory Press, New York).

Polypeptides and nucleic acids of the invention may be prepared synthetically using conventional synthesizers. Alternatively, they may be produced using recombinant DNA technology and may be incorporated into suitable expression vector, which is then used to transform a suitable host cell, such as a prokaryotic cell such as *E. coli*. The transformed host cells are cultured and the polypeptide isolated therefrom.

Therefore, the invention also provides a vector comprising such a polynucleotide. This includes recombinant constructs comprising one or more of the nucleic acid molecules described above. The constructs comprise a vector, such as a plasmid or viral vector, into which a nucleic acid molecule of the invention has been inserted, in a forward or reverse orientation. In a preferred aspect of this embodiment, the construct further comprises regulatory sequences, including, for example, a promoter operably linked to the sequence. Large numbers of suitable vectors and promoters are known to those of skill in the art and are commercially available. Appropriate cloning and expression vectors for use with prokaryotic and eukaryotic hosts are also described in Sambrook, et al.

A further aspect of the invention provides a cell comprising any of the polypeptide, polynucleotide or vector according to the invention. For example, a suitable cell may be a *Salmonella* cell, such as a *Salmonella enterica* cell, in some embodiments from the serovar *typhimurium*. The *Salmonella* may be an attenuated strain. Strains χ8914 and χ9241 may optionally be employed. For example, a suitable system is described in Kulkarni et al. (2008, Vaccine vol. 26, 4194-4203). Preferably the host cell is not a stem cell, especially not a human stem cell.

A further aspect of the invention provides an antibody raised against a polypeptide according to the first aspect of the invention.

A further aspect of the invention provides a subunit vaccine comprising a polypeptide according to the first aspect of the invention. For example, this may be in the form of a fusion protein and/or in the form of a recombinant viral vaccine.

A further aspect provides a vaccine composition which may comprise a polypeptide, polynucleotide, vector, antibody and/or subunit vaccine according to preceding aspects of the invention. The composition may further comprise excipients and/or diluents appropriate for the means by which the composition is to be administered to a subject in need of vaccination against developing disease caused by *C. perfringens* and/or Etx. Selection of appropriate components is within the routine capability of the skilled person without the application of inventive activity.

For example, the vaccine composition of the invention may conveniently be formulated using a pharmaceutically acceptable excipient or diluent, such as, for example, an aqueous solvent, non-aqueous solvent, non-toxic excipient, such as a salt, preservative, buffer and the like. Examples of non-aqueous solvents are propylene glycol, polyethylene glycol, vegetable oil and injectable organic esters such as ethyloleate. Aqueous solvents include water, alcoholic/aqueous solutions, saline solutions, parenteral vehicles such as sodium chloride, Ringer's dextrose, etc. Preservatives include antimicrobial, anti-oxidants, chelating agents and inert gases. The pH and exact concentration of the various components the vaccine composition are adjusted according to routine skills.

Optionally, the vaccine formulation may include a carrier. Commonly used carrier molecules are bovine serum albumin (BSA), keyhole limpet hemocyanin (KLH), ovalbumin, mouse serum albumin, rabbit serum albumin and the like. Synthetic carriers may be used and are readily available. Means for conjugating peptides to carrier proteins are well known in the art and include glutaraldehyde, m-maleimidobenzoyl-N-hydroxysuccinimide ester, carbodiimide and bis-biazotized benzidine.

In certain situations, it may also be desirable to formulate the vaccine composition to comprise an adjuvant to enhance the immune response. Such adjuvants include all acceptable immunostimulatory compounds such as, for example, a cytokine, toxin, or synthetic composition. Commonly used adjuvants include aluminium hydroxide, aluminium phosphate, calcium phosphate, Freund's adjuvants and Quil-A saponin. In addition to adjuvants, it may be desirable to co-administer biologic response modifiers (BRM) with the peptide or variant or derivative to down regulate suppressor T cell activity.

Possible vehicles for administration of the vaccine formulation include liposomes. Liposomes are microscopic vesicles that consist of one or more lipid bilayers surrounding aqueous compartments. Liposomes are similar in composition to cellular membranes and, as a result, liposomes generally can be administered safely and are biodegradable. Techniques for preparation of liposomes and the formulation (e.g., encapsulation) of various molecules, including peptides and oligonucleotides, with liposomes are well known.

Depending on the method of preparation, liposomes may be unilamellar or multilamellar and can vary in size with diameters ranging from 0.02 µm to greater than 10 µm. Liposomes can also adsorb to virtually any type of cell and then release the encapsulated agent. Alternatively, the liposome fuses with the target cell, whereby the contents of the liposome empty into the target cell. Alternatively, an absorbed liposome may be endocytosed by cells that are phagocytic. Endocytosis is followed by intralysosomal degradation of liposomal lipids and release of the encapsulated agents. In the present context, the polypeptide according to the invention can be localized on the surface of the liposome, to facilitate antigen presentation without disruption of the liposome or endocytosis. Irrespective of the mechanism or delivery, however, the result is the intracellular disposition of the associated polypeptide.

Liposomal vectors may be anionic or cationic. Anionic liposomal vectors include pH sensitive liposomes which disrupt or fuse with the endosomal membrane following endocytosis and endosome acidification. Cationic liposomes are preferred for mediating mammalian cell transfection in vitro, or general delivery of nucleic acids, but are used for delivery of other therapeutics, such as peptides.

Other suitable liposomes that are used in the methods of the invention include multilamellar vesicles (MLV), oligolamellar vesicles (OLV), unilamellar vesicles (UV), small unilamellar vesicles (SUV), medium-sized unilamellar vesicles (MIN), large unilamellar vesicles (LUV), giant unilamellar vesicles (GUV), multivesicular vesicles (MVV), single or oligolamellar vesicles made by reverse-phase evaporation method (REV), multilamellar vesicles made by the reverse-phase evaporation method (MLV-REV), stable plurilamellar vesicles (SPLV), frozen and thawed MLV (FATMLV), vesicles prepared by extrusion methods (VET), vesicles prepared by French press (FPV), vesicles prepared by fusion (FUV), dehydration-rehydration vesicles (DRV), and bubblesomes (BSV). Techniques for preparing these liposomes are well known in the art.

Other forms of delivery particle, for example, microspheres and the like, also are contemplated for delivery of the peptide epitopes or polyepitopes.

Alternatively, nucleic acid-based vaccines may be produced that comprise nucleic acid, such as, for example, DNA or RNA, encoding the immunologically active peptide epitope or polyepitope and cloned into a suitable vector (e.g., vaccinia, canarypox, adenovirus, or other eukaryotic virus vector).

Alternatively, the polypeptide may be administered in the form of a cellular vaccine via the administration of autologous or allogeneic APCs or dendritic cells that have been treated in vitro so as to present the peptide on their surface. *Salmonella enterica* or *Escherichia coli* strains harbouring mutations which reduce their virulence and allow them to colonise a host animal without causing disease might be used to deliver vaccine antigens, especially for administration to non-human animals. The bacteria used might include strains which are already used as vaccine in livestock where the attenuating lesion is not fully characterised. In addition, strains in which mutations have been deliberately introduced into the bacterium to rationally attenuate virulence could be used to deliver the epsilon toxoid. Such mutations include those in the shikimate pathway, purine biosynthesis pathway, mutations in genes encoding adenylate cyclase (cya) and camp receptor protein (crp) or mutations in the phoP and phoQ genes, involved in the two-component regulatory system. Other rationally mutated strains which have been studied include those with deletions in genes involved in the biosynthesis of peptidoglycan, DNA recombination and repair or DNA methylation. Bacteria which are able to normally colonise the gut but are non-pathogenic such as *Lactobacillus* sp. or *Lactococcus* sp. strains or *Bacillus subtilis*, might also be used to deliver vaccine antigens. In the case of *B. subtilis*, the vaccine antigen might be expressed on the vegetative cell or the spore. The antigen might also be delivered as a naked DNA vaccine where the gene encoding the epsilon toxoid is cloned into a mammalian expression vector and expressed from a eukaryotic promoter.

Such an approach, for example using *Salmonella*, offers a number of advantages. First, live *Salmonella* vaccines can be given orally (the natural route of infection), enabling a non-invasive route of vaccine administration. Second, both mucosal and systemic immune responses can be elicited, which may be important for protection against infection. In addition, live attenuated *Salmonella* vaccines are able to simulate both humoral and cellular immune responses that may be important for protection against disease. Finally, since *Salmonella* is genetically tractable, recombinant *Salmonella* vaccines are relatively easy to develop and are also relatively cost effective to produce.

One of the most widely studied classes of attenuated *Salmonella* used as carriers of foreign antigens are auxotrophs. For example, genetically defined mutants of the aroA gene, encoding 5-enolpyruvylshikimate-3-phosphate synthase, have been constructed in both *S. enterica* var. *Typhimurium* and var. *Typhi*. These mutants are attenuated and immunogenic in mice. Examples of other auxotrophic mutants include *Salmonella* with deletions in the genes involved in the purine biosynthetic pathway. Another well-studied group of attenuated *Salmonella* are mutants that have defined deletions in genes involved in the regulation of *Salmonella* virulence. For example, mutations in genes encoding adenylate cyclase (cya) and camp receptor protein (crp) affect the expression of genes involved.

In one embodiment, the vaccine composition may be included in a foodstuff (i.e., a food material suitable for consumption by a human or an animal) comprising a polypeptide and/or a polynucleotide and/or a vector and/or a cell and/or a subunit vaccine and/or vaccine composition according to preceding aspects of the invention. This may, in non-limiting examples, be in the form of pellets, crumbs or a mash which may further comprise, again for example only, grain, grass and/or protein components. The composition may also be included in drinking liquids and/or administered via a spray into the atmosphere surrounding the animal which is, consequently, inhaled by the animal.

If the vaccine composition is for administration to a human subject, it may be in a form suitable for administration orally (e.g. in a dietary supplement) and/or parenterally, for example, by injection, inhalation, or by transdermal administration via a patch, lotion or gel. The particular forms outlined above are also generally useful for administration to a human subject.

A polypeptide, polynucleotide, vector, subunit vaccine, antibody and/or vaccine composition according to the invention may be for use in a method of vaccinating a subject against developing a disease caused by *Clostridium perfringens*, the disease for example involving accumulation in the subject's bloodstream of epsilon toxin which may be released by *C. perfringens*, particularly active epsilon toxin lacking the N- and C-termini of the full length prototoxin. The invention also provides a method of vaccinating a subject against developing a disease caused by *Clostridium perfringens* and/or caused by (or associated with the presence of) the epsilon toxin, especially active toxin, the method comprising administering to a subject a protective amount of a polypeptide, polypeptide, polynucleotide, vector, subunit vaccine, antibody and/or vaccine composition according to the invention. The subject may be a human or a non-human animal. The non-human animal may be a ruminant animal, such as a sheep, pig or goat, or a bovine animal such as a domestic cow. Young animals such as lambs, piglets, kids and calves are also included.

A "protective amount" is an amount sufficient to induce an immune response in the subject, such that the probability of the subject developing a disease caused by *C. perfringens*, for example caused by (or associated with the presence of) epsilon toxin, especially active toxin, is reduced or removed. For example, antibodies capable of binding to SEQ ID NO:5 and/or 22 may be detectable after the administration, where such antibodies were not detectable prior to the administration, or only detectable at lower concentrations than after administration.

The invention also provides a kit comprising a polypeptide, polynucleotide, vector, subunit vaccine, antibody and/or vaccine composition according to the invention, the kit having uses, for example, in methods of vaccinating a subject against developing a disease caused by infection with *Clostridium perfringens*, particularly a disease caused by epsilon toxin. The kit may further comprise instructions enabling a user to carry out a method of vaccinating a subject against developing a disease caused by *Clostridium perfringens*, particularly a disease caused by epsilon toxin.

A disease caused by *Clostridium perfringens* and/or by active epsilon toxin, as mentioned herein may be, for example, enterotoxemia including pre-disease symptoms such as systemic lesions and enterocolitis. Other symptoms may include oedema of the main target organs of the kidneys and brain and damage to vascular endothelial cells. The terminal phase of enterotoxaemia is characterized by severe neurological disorders that include opisthotonus, seizures and agonal struggling.

Throughout the description and claims of this specification, the words "comprise" and "contain" and variations of the words, for example "comprising" and "comprises", mean "including but not limited to" and do not exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Preferred features of each aspect of the invention may be as described in connection with any of the other aspects.

Other features of the present invention will become apparent from the following examples. Generally speaking the invention extends to any novel one, or any novel combination, of the features disclosed in this specification (including the accompanying claims and drawings). Thus, features, integers, characteristics, compounds or chemical moieties described in conjunction with a particular aspect, embodiment or example of the invention are to be understood to be applicable to any other aspect, embodiment or example described herein, unless incompatible therewith.

Moreover, unless stated otherwise, any feature disclosed herein may be replaced by an alternative feature serving the same or a similar purpose.

BRIEF DESCRIPTION OF THE FIGURES

Embodiments of the invention will now be described, by way of example only, with reference to FIGS. 1-8 in which:

FIG. 1 is a schematic representation of SEQ ID NO:16, a recombinant epsilon protoxin (P-Etx), with a N-terminal PeIB leader peptide in place of the 13 amino acids N-terminal peptide sequence and with a C-terminal His-tag to aid purification (the amino acid sequences around the processing sites are also shown)(the depicted sequence "MKYLL-PTAAAGLLLLAAQPA MAMGKASYDNVDTL" are residues 1-35 of SEQ ID NO: 16, "EYVIPVDKKEKS" are residues 277-288 of SEQ ID NO: 16, and the terminal H, residue 315, is also depicted);

FIG. 7A shows trypsin-treated wild-type and Y43A/Y209A epsilon toxins alongside inactivated wild-type prototoxin were added to the medium overlying MDCK cells in 96-well plates, cytotoxicity being assessed using the LDH assay; data represent the means and standard deviations of three independent experiments performed in duplicates;

FIG. 7B shows detection of MDCK cells with bound purified recombinant wild-type and Y43A/Y209A epsilon prototoxins; all samples were run in quadruplicates and data were analyzed by 1 way ANOVA-values significantly different from control (wild-type toxin) are shown as ***$P<0.001$;

FIG. 8A shows that the cytotoxicity of trypsin activated Y43A/Y209A in wild-type background was identical to that of Y43A/Y209A in H149A background;

FIG. 8B shows that the fluorescent signal of cells treated with Y43A/Y209A in wild-type background was equivalent to that of cells treated with Y43A/Y209A in H149A background and PBS;

EXAMPLES

Materials and Methods

Chemicals

Figure 2:
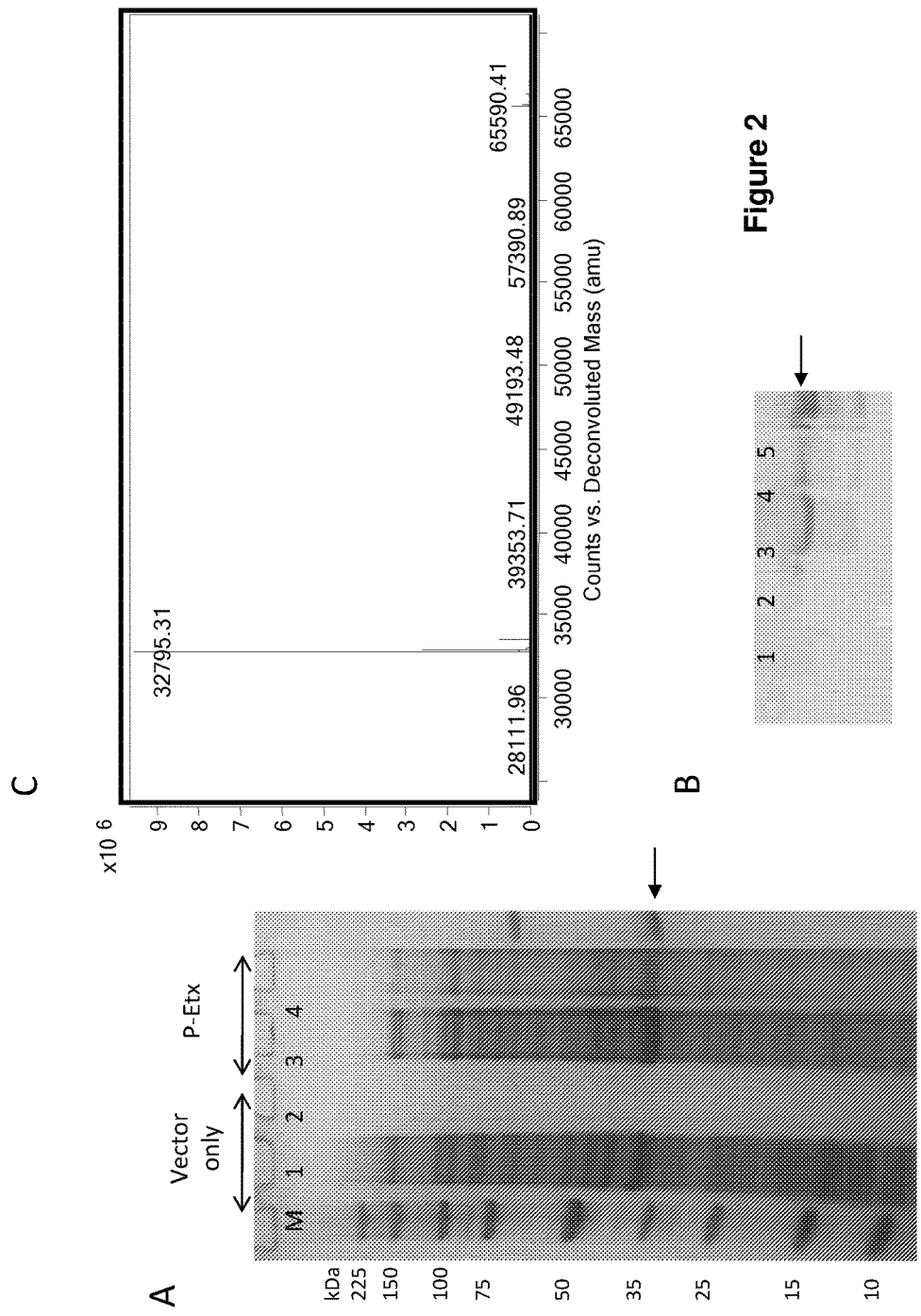
FIG. 2A shows Coomassie staining visualisation of P-Etx expression: lane 1, post-induction bacterial protein extract from cells expressing vector only, soluble fraction; lane 2, post-induction bacterial protein extract from cells expressing vector only, insoluble fraction; lane 3, post-induction bacterial protein extract from cells expressing P-Etx, soluble fraction, P-Etx showing as an intense ~35 kDa band; lane 4, post-induction bacterial protein extract from cells expressing P-Etx, insoluble fraction; lane 5, P-Etx after affinity purification, with an arrowhead indicating the position of epsilon prototoxin.
FIG. 2B shows Western blot analysis of P-Etx expression using anti-His6 antibody (lanes as in FIG. 2A), with the positions of molecular mass markers are shown (M)
FIG. 2C shows mass spectrometry analysis showing the actual molecular weight of the prototoxin, which corresponds to the expected molecular weight of 32.79 kDa.

All chemicals were obtained from Sigma Chemical Co. (St. Louis, Mo.) unless otherwise specified.

Cell Culture

MDCK.2 cells (ATCC-LGC Standards, Teddington, UK) were routinely cultured in Eagle's Minimum Essential Medium (EMEM) supplemented with 10% Foetal Bovine Serum Gold (PAA, Pasching, Austria) at 37° C. in a humidified atmosphere of 95% air/5% $CO_2$. The culture medium was replaced every 2-3 days. Cells were routinely detached by incubation in trypsin/EDTA and split as appropriate (typically 1:6 dilutions).

Cloning of Recombinant Epsilon Prototoxin (P-Etx)

The gene encoding epsilon prototoxin, etxD, from *C. perfringens* Type D strain NCTC 8346 was PCR amplified and cloned into plasmid pC10 as described by Oyston et al. (1998). The etxD gene was subsequently PCR amplified from plasmid pC10 using the oligonucleotides:

```
                                         (SEQ ID NO: 30)
5'-GGAATTCCCATGGGTAAAGCTTCTTATGATAATGT-3'

(SEQ ID NO: 31)
5'-ATTGCCGCTCGAGTTTTATTCCTGGTGCC-3'
```

These incorporated NcoI and XhoI restriction sites, respectively (restriction enzyme cleavage sites are underlined). The PCR cycle consisted of 1 min initial denaturation of template DNA at 94° C. followed by 25 cycles of 94° C. for 30 sec, 50° C. for 30 sec and 72° C. for 30 sec, followed by 10 min final extension at 72° C. The PCR amplified fragment was digested with NcoI and XhoI restriction endonucleases and cloned into the similarly digested expression vector pET-26b(+) (Merck, Darmstadt, Germany). This placed the etxD gene under the regulation of the bacteriophage T7 RNA polymerase and fused the N-terminal end of the prototoxin (P-Etx) without the 13 N-terminal residues (KEISNTVSNEMSK; SEQ ID NO:32) to the PelB leader peptide and the C-terminal end of the prototoxin to a polyhistidine (6×His) affinity tag to aid purification of the protein. In addition, recombinant P-Etx contains the H149A mutation (amino acid numbering corresponds to prototoxin without the N-terminal peptide sequence, SEQ ID NO:26), generating a low toxicity variant of Etx to enable manipulation of activated toxin at containment level 2 (Oyston et al. (1998)). The recombinant plasmid expressing P-Etx with the H149A mutation (SEQ ID NO:16) is termed pET26-b(+)/P-Etx_H149A.

Site Directed Mutagenesis

Mutations were introduced into the gene encoding P-Etx using the QuikChange Lightning Site-Directed Mutagenesis Kit (Agilent Technologies, Inc. Santa Clara, US) according to the manufacturer's instructions. Synthetic oligonucleotide primer pairs (Eurofins MWG Operon, Ebersberg, Germany) were used to change each tyrosine codon to an alanine codon. Primers used for site directed mutagenesis are listed in Table 2 below. To create Tyr mutants, plasmid pET26-b(+)/P-Etx_H149A served as template, unless otherwise stated. The presence of the intended mutations was verified by DNA sequencing (Source BioScience, Cambridge, UK).

Expression and Purification of Recombinant Epsilon Prototoxin (P-Etx) and its Derivatives Recombinant P-Etx and its derivatives were expressed in *E. coli* Rosetta 2 (DE3) cells (Merck, Darmstadt, Germany) grown in ZYM-5052 autoinducing media (Studier et al. (2005)) supplemented with 50 μg/mL kanamycin and 34 μg/mL chloramphenicol. Cells (100 mL) were grown at 37° C. for 2-3 h and cultured for a further 24 h at 20° C.

For protein purification, cells were harvested by centrifugation and 2 g of cell paste was extracted by 10 mL Bugbuster protein extraction reagent (Merck, Darmstadt, Germany) containing 10 μL rlysozyme (1 KU/μL) (Merck, Darmstadt, Germany) and 10 μL benzonase nuclease (25 u/μL) (Merck, Darmstadt, Germany). The cell suspension was incubated on a rotating mixer at a slow setting for 25 min at room temperature and centrifuged at 16,000×g for 20 min at 4° C. to separate soluble (supernatant) and insoluble (pellet) fractions. The supernatant was applied to a His GraviTrap column (GE Healthcare Life Sciences, Little Chalfont, UK) following the manufacturer's guidelines. In brief, His-tagged proteins were bound to the affinity column using a buffer composed of 20 mM sodium phosphate, 500 mM NaCl, 20 mM imidazole, pH 7.4. The column was washed with a buffer composed of 20 mM sodium phosphate, 500 mM NaCl, 60 mM imidazole, pH 7.4. P-Etx was eluted in a buffer composed of 20 mM sodium phosphate, 500 mM NaCl, 500 mM imidazole, pH 7.4. All purification steps were carried out at 4° C. The P-Etx containing eluate was applied to a PD-10 Desalting Column (GE Healthcare Life Sciences, Little Chalfont, UK) for buffer exchange and further sample clean up. P-Etx was eluted from PD-10 column in 10 mM phosphate buffer, 2.7 mM potassium chloride, 137 mM NaCl, pH 7.4. Protein concentrations were determined using the BCA assay (Fisher Scientific UK Ltd, Loughborough, UK) and protein was stored in aliquots at 80° C.

The purity of P-Etx and its derivatives was confirmed by SDS-PAGE. Proteins were resolved by 4-12% Bis-Tris NuPAGE gels (Invitrogen Ltd., Paisley, UK) using Surelock Xcell apparatus (Invitrogen Ltd., Paisley, UK) and NuPAGE MES SDS running buffers (Invitrogen Ltd., Paisley, UK). All samples were heated prior to loading at 95° C. for 5 min in NuPAGE LDS sample buffer (Invitrogen Ltd., Paisley, UK) containing 0.1 M dithiothreitol (DTT). Gels were typically run at 200 V for 45 min. After electrophoretic separation, proteins were either visualized by SimplyBlue staining (Invitrogen Ltd., Paisley, UK) or transferred to nitrocellulose membrane using iBlot transfer stacks (Invitrogen Ltd., Paisley, UK) and iBlot apparatus (Invitrogen Ltd., Paisley, UK) according to the manufacturer's instructions. His-tag specific monoclonal antibody conjugated to horseradish peroxidise (Merck, Darmstadt, Germany) was used to detect P-Etx. Prestained molecular weight standards (Merck, Darmstadt, Germany) were used as markers. Lysate from *E. coli* Rosetta 2 (DE3)/pET26-b(+) served as a negative control.

Trypsin Treatment of Epsilon Prototoxin (P-Etx)

For cytotoxicity assays, purified P-Etx was activated with trypsin from bovine pancreas to generate the active toxin (Etx). Trypsin was prepared in PBS and added to prototoxin at 1:100 (w:w) ratio and incubated at room temperature for 30 min. Protease Inhibitor Cocktail, EDTA-Free (Fisher Scientific UK Ltd, Loughborough, UK) was added to the supernatant to inhibit residual trypsin in the samples. Conversion of the prototoxin to toxin was assessed by SDS-PAGE.

CD Spectra Analysis of Purified Recombinant Epsilon Prototoxin and its Variants

To confirm that the Tyr mutations do not alter the secondary structure of the proteins, purified mutants were analysed by CD spectroscopy (King's College, London).

Cytotoxicity Assay

The cytotoxic activity of trypsin-activated epsilon toxins towards MDCK.2 cells was determined by measuring the release of lactate dehydrogenase (LDH) from necrotic cells using the CytoTox 96 nonradioactive cytotoxicity assay kit (Promega UK, Southampton, UK) according to the manufacturer's protocol. In brief, a 2-fold dilution series of each activated toxin (ranging from 3 μM to 1.46 nM) was prepared in PBS and added to MDCK.2 cells seeded into 96-well plate ($2 \times 10^4$ cells/well). Following incubation at 37° C. for 3 hours, cell culture medium (50 μL) was harvested from sample monolayers and transferred to a fresh 96-well enzymatic assay plate and 50 μL of reconstituted substrate mix was added to each well. The plate was incubated for 30 min at room temperature, protected from light. Absorbance was read at 490 nm using a Model 680 Microplate Reader (Bio-Rad). The toxin dose required to kill 50% of the cell monolayer ($CT_{50}$) was determined by nonlinear regression analysis (GraphPad). The absorbance values for each sample were normalized by subtracting the absorbance value obtained for the culture medium from untreated cells. All experiments were performed in triplicates with three technical replicates each.

Binding Assay

On-Cell Western assays were used to measure direct binding of the purified prototoxin and its variants to MDCK.2 cells. The inactive prototoxin binds to the same surface cell receptors as the full active molecule and can prevent its binding and further toxicity (Petit et al. (1997)). Briefly, black 96-well microtiter plates were seeded with $2 \times 10^4$ MDCK.2 cells/well in EMEM medium containing 10% foetal bovine serum. To allow cells to attach, the plates were incubated overnight at 37° C. in a humidified atmosphere of 95% air/5% $CO_2$. The next day plates were washed with phosphate-buffered saline (PBS) containing 1 mM $MgCl_2$ and 1 mM $CaCl_2$. Each affinity-purified prototoxin was added to triplicate wells containing MDCK.2 cells at a final concentration of 5 μM. Cells were incubated with prototoxin for 30 min at 37° C. in a humidified atmosphere of 95% air/5% $CO_2$. For background control, triplicate wells were incubated with PBS only. Unbound toxin was removed by washing cell monolayers three times in PBS. Cells were then fixed with 4% formaldehyde at room temperature for 15 min. After washing of the cell monolayers with PBS three times, wells were blocked for 1.5 hours using Odyssey blocking buffer (LI-COR Biosciences, Lincoln, Nebr., USA). Bound protein was detected with a 1:500 dilution of mouse anti-His Tag monoclonal antibody (Invitrogen Ltd., Paisley, UK) and a 1:500 dilution of IRDye 800CW goat anti-mouse IgG (H+L) antibody (LI-COR Biosciences, Lincoln, Nebr., USA). Plates were imaged at 800 nm to detect IRDye-labeled secondary antibody using the Odyssey CLx infrared imaging system (LI-COR Biosciences, Lincoln, Nebr., USA). All experiments were performed in triplicates with three technical replicates each.

Immunisation of Rabbits

Epsilon prototoxin variant Y43A/Y209A in wild-type background was sent to Immune Systems Ltd for immunization of New Zealand White rabbits. For each injection, 1.7 mg protein was lyophilized and used to immunize three rabbits. For the initial immunisation Freund's complete adjuvant was used. The remainder immunizations used Freund's incomplete adjuvant. Injections were carried out every 14 days and harvest bleed was done on day 107, 9 days after the last injection.

Results

Expression of Recombinant Epsilon Prototoxin (P-Etx) and its Variants in E. coli Recombinant P-Etx contains the H149A mutation (numbering of this mutation corresponds to prototoxin without the N-terminal peptide, SEQ ID NO:26), which makes trypsin activated toxin 6-fold less toxic to MDCK cells and 67-fold less toxic in mice (Oyston et al. (1998)), allowing manipulation of activated toxin at containment level 2. H149 is located in Domain III of Etx, in close proximity to the tip of the β-hairpin in Domain II, with the side-chain of His buried by the C-terminal peptide in Domain III. Therefore, the presence of this mutation is unlikely to interfere with receptor binding of Etx, which is suggested to be mediated by Domain I at the N-terminus. H149A is likely to reduce cytoxicity of Etx either by interfering with oligomerisation or with the mechanism of extension of the β-hairpin. In addition, MDCK cell assay of the H149A site directed mutant (EtxB) showed that H149 does not play a key role in Etx activity (Payne, et al. (1997) Rev. Med. Microbiol. vol. 8, S31).

To identify residues involved in receptor binding of Etx, the gene encoding epsilon prototoxin (P-Etx) was cloned into the expression vector pET-26b(+) as described in Materials and Methods. Recombinant P-Etx contains the PelB signal peptide in place of the 13 amino acids N-terminal peptide, and a C-terminal polyhistidine (6×His) tag downstream of the C-terminal peptide sequence to aid subsequent purification of the prototoxin by affinity chromatography (FIG. 1). The PelB signal peptide directs the expressed P-Etx protein to the bacterial periplasm where this sequence is removed by a signal peptidase.

For high level expression of P-Etx, recombinant plasmid was transferred into DE3 lysogen E. coli strain Rosetta 2 carrying a chromosomal copy of the bacteriophage T7 RNA polymerase gene under the control of the lacUV5 promoter, and expression was induced using the autoinduction system as described by Studier (2005; Prot. Exp. Purif. vol. 41, 207-234). As shown in FIG. 2A, recombinant P-Etx protein is expressed mainly in the soluble fraction. Full length P-Etx without the PelB leader peptide sequence was predicted to encode a 32.79 kDa protein. The recombinant protein had an apparent molecular size of 35 kDa (His-tagged protein) as detected by SDS-PAGE and Western blot analysis (FIGS. 2A, B). His-tag affinity purification resulted in high yields of about 100 mg purified protein per L culture. The actual molecular weight of the prototoxin was determined by mass spectrometry analysis, which corresponded to the expected molecular weight of 32.79 kDa (FIG. 2C).

Figure 3:
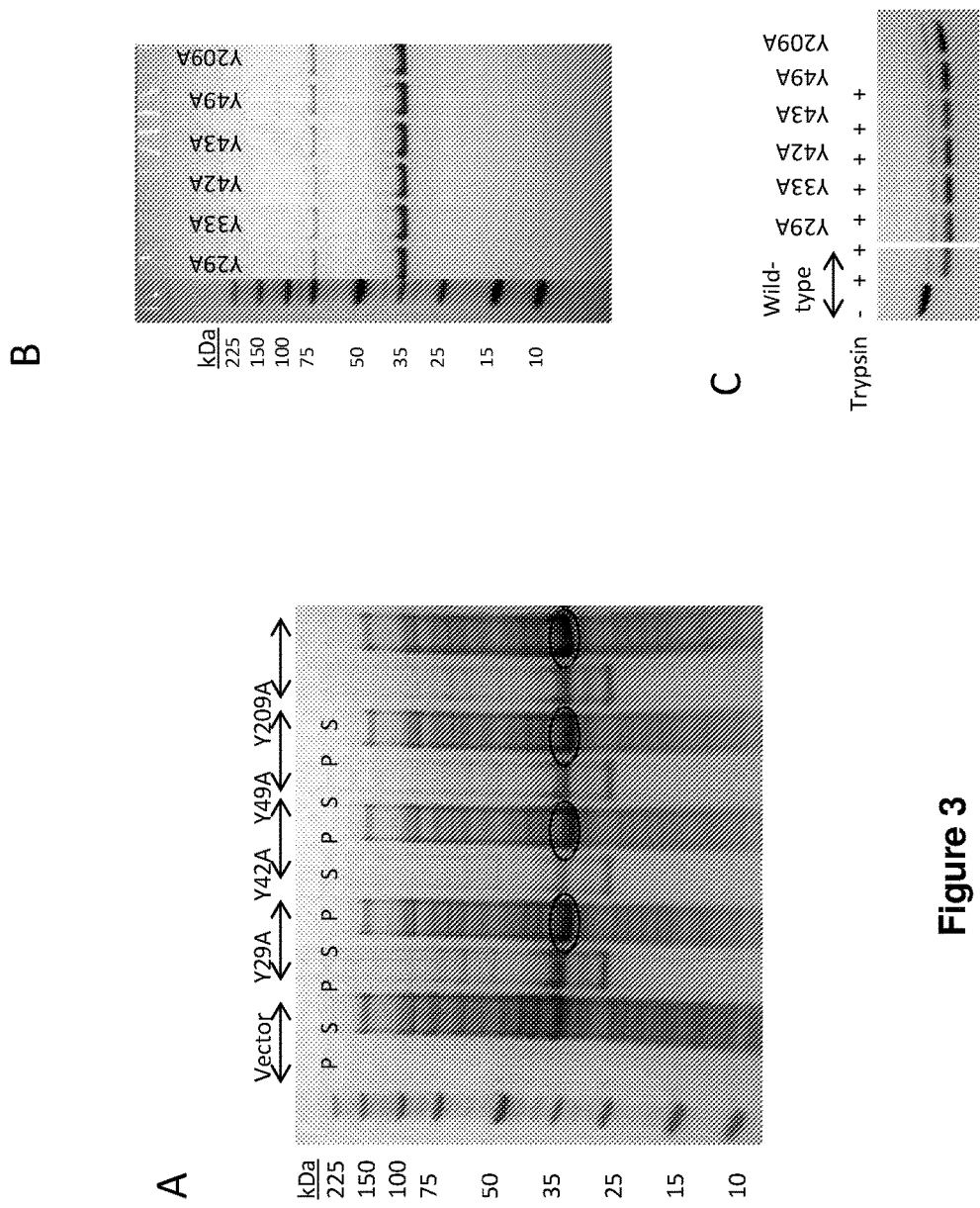
FIG. 3A shows Coomassie staining visualisation of expression of recombinant P-Etx mutants were expressed in *E. coli* Rosetta2(DE3) cells, with insoluble (P) and soluble (S) fractions of post-induction bacterial protein extracts marked; recombinant Tyr mutants are expressed mainly in the soluble fraction (S), indicated by the presence of an intense ~35 kDa band (circled)
FIG. 3B shows the result of affinity purification of Tyr mutants.
FIG. 3C shows purified recombinant epsilon prototoxin trypsin treated samples separated by SDS-PAGE and visualized by Coomassie staining.

Site Directed Mutagenesis of P-Etx to Identify the Role of Tyrosines in Receptor Binding To test the role of the N-terminal domain I of Etx in cell binding, the inventors initially targeted two loops in this region by deletion mutagenesis, termed loop 1 (ΔK32-I55) and loop 2 (ΔS201-S220). However, loop deletions lead to toxin instability as most of the protein expressed in the insoluble fraction and purification of soluble protein resulted in yields that were impractical for further cytotoxicity and binding assays. To identify the role of loops 1 and 2 in cell binding, the inventors next concentrated on mutagenesis of individual residues within these loops. Six surface exposed tyrosines were selected for site directed mutagenesis, five residues in loop1 (Y29, Y33, Y42, Y43 and Y49) and one residue in loop2 (Y209), each being replaced individually with alanine. Each Tyr mutant was expressed and purified using the method developed for wild-type P-Etx. Similar to wild-type P-Etx, all Tyr mutants expressed mostly in the soluble fraction and gave similar yields and purity to wild-type P-Etx (FIGS. 3A, 3B), indicating that these mutations do not affect the structure of the toxin. In addition, the trypsin digest profiles of all Tyr mutants were identical to that of wild-type P-Etx, producing a lower molecular weight active toxin (FIG. 3C). Further CD spectra analysis confirmed that all Tyr mutants are adopting a predominantly β-sheet conformation, similar to wild-type P-Etx (data not shown), indicating that the single tyrosine mutants are folded correctly.

Cytotoxic Activity of Single Tyrosine Mutants

Recombinant P-Etx can be activated by trypsin digestion, which removes a C-terminal peptide together with the His-tag (FIG. 1). To determine the effect of the single tyrosine mutations on cytotoxic activity of Etx, each mutant prototoxin was activated by trypsin digestion. A 2-fold dilution series (ranging from 3 µM to 1.46 nM) of each activated toxin was added to MDCK.2 cells seeded into 96-well plate as described in Materials and Methods. Following 3 h incubation at 37° C., the cell culture medium was harvested and cytotoxicity was measured by the LDH assay, which quantitatively measures the amount of LDH released from the cytosol of lysed cells into the cell culture medium. The tissue culture dose of each toxin that killed 50% of the cells ($CT_{50}$) was determined by nonlinear regression analysis and compared to that of "wild-type" Etx (comprising the H149A mutation). Cytotoxic activity of tyrosine mutants was expressed as the fold-change in $CT_{50}$ relative to "wild-type" toxin. Mutants Y43A and Y209A showed significantly reduced cytotoxic activity relative to "wild-type" toxin (27-fold and 10-fold increase in CT50, respectively, FIG. 4). The Y43A mutation is located in loop 1. The cytotoxicity of MDCK.2 cells treated with inactivated P-Etx was indistinguishable from that of untreated control cells (data not shown). The average $CT_{50}$ for "wild-type" epsilon toxin was determined to be 22 nM in 100 µl (721 ng per ml).

Binding of Single Tyrosine Mutants to MDCK 2 Cells

Figure 5:
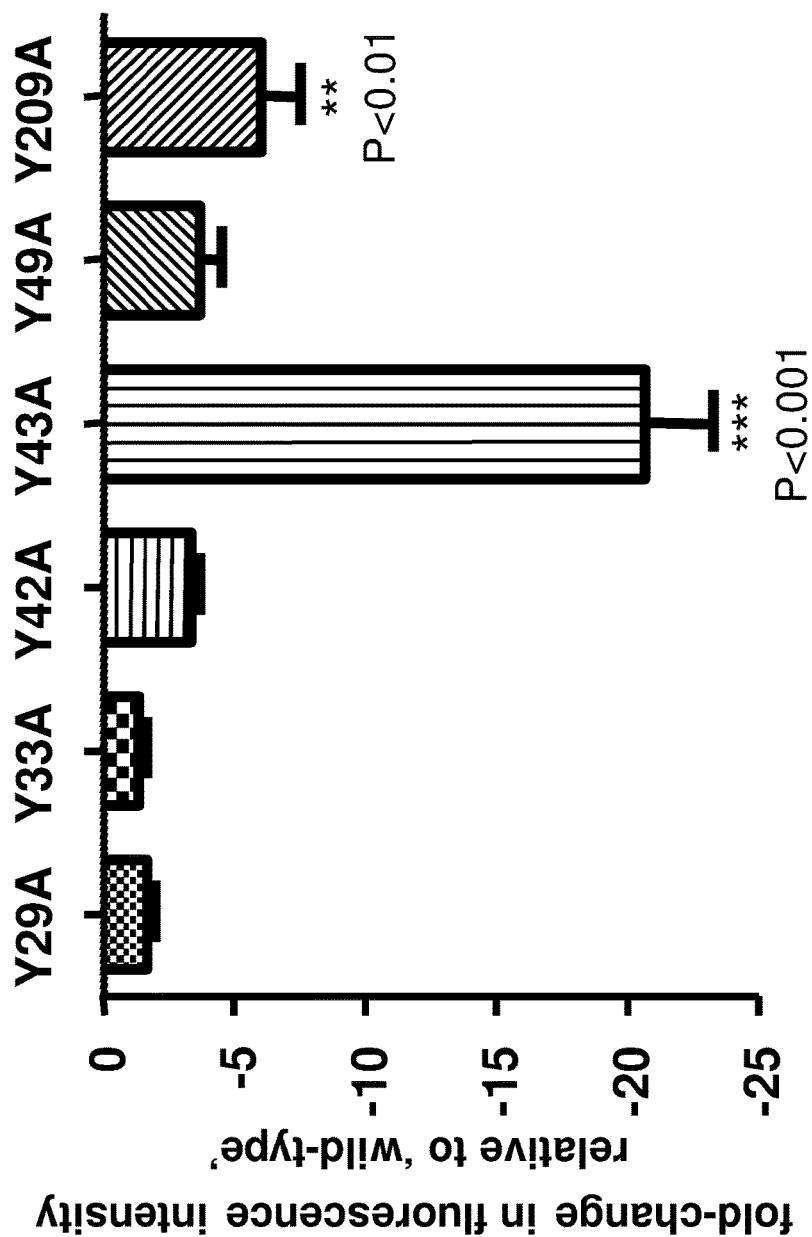
FIG. 5 shows the effects of Tyr mutations on the binding of epsilon prototoxin to MDCK.2 cells, with mutants Y43A and Y209A showing significantly reduced binding activity relative to "wild-type" prototoxin (−21-fold and −6-fold, respectively) as determined by quantifying the fluorescent signal from each well using One-Way ANOVA analysis followed by Dunnett's post test; data represent the means and standard deviations of three independent experiments performed in triplicates.

The inventors next tested if the reduced cytotoxicity of the single Tyr mutants related to their reduced ability to bind to MDCK.2 cells. For this, on-cell Western studies were carried out using prototoxin as described in Materials and Methods. In brief, 96-well plates seeded with $2 \times 10^4$ MDCK.2 cells/well were incubated with purified prototoxin at a final concentration of 5 µM for 30 min at 37° C. Bound protein was detected with a His-tag specific primary antibody and an IRDye 800CW-labeled secondary antibody. Plates were imaged using an Odyssey imager. All binding studies used prototoxin as it can bind to cells without causing cell lysis (see FIG. 7A). Mutants Y43A and Y209A showed significantly reduced binding activity relative to 'wild-type' prototoxin (−21-fold and -6-fold, respectively; FIG. 5) as determined by quantifying the fluorescent signal from each well using one-way ANOVA analysis. The most significant reduction in fluorescent signal was observed with the Y43A mutant, indicating that Y43 plays a critical role in cell binding. The reduced binding ability of the Tyr mutants correlated with their reduced ability to bind to cells (Table 1).

TABLE 1

| Tyrosine mutant | % cytoxic activity relative to wild-type | % binding activity relative to wild-type |
|---|---|---|
| Y33A | 45 | 75 |
| Y29A | 32 | 62 |
| Y42A | 19 | 33 |
| Y49A | 15 | 26 |
| Y209A | 10 | 19 |
| Y43A | 4 | 5 |

Figure 4:
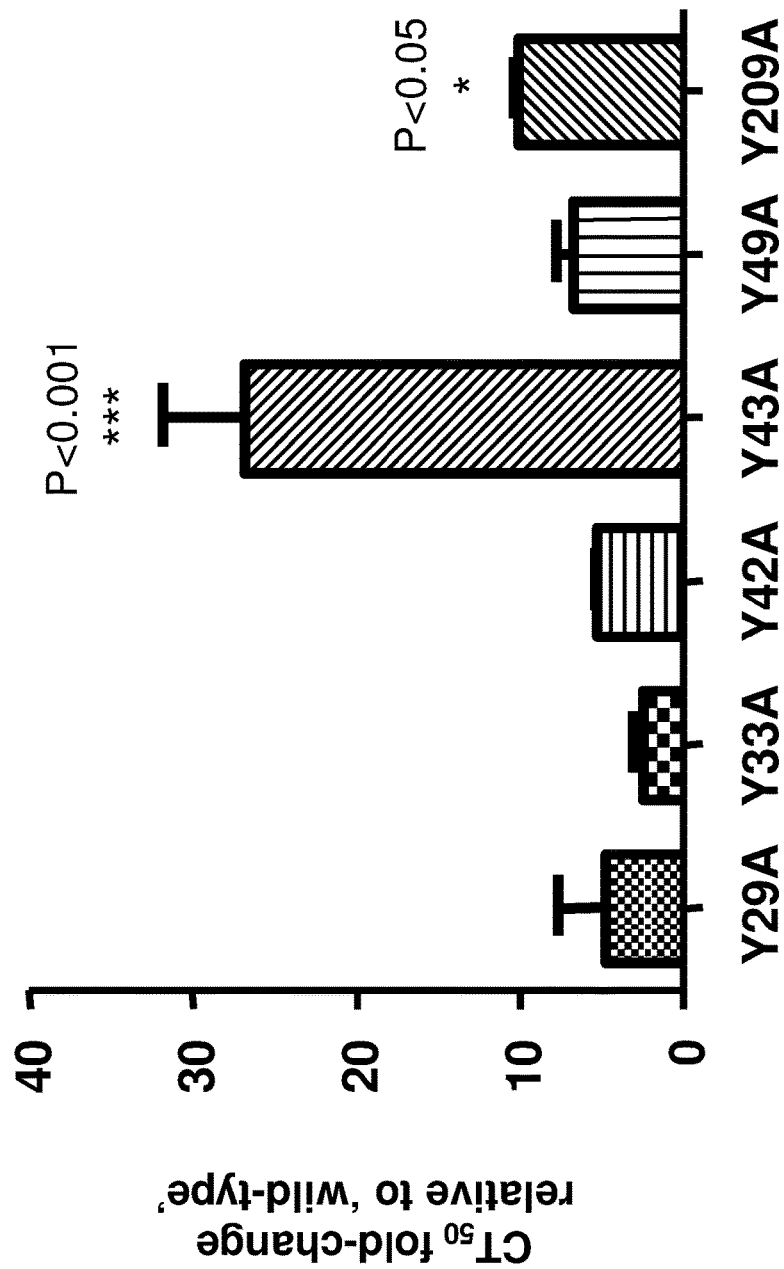
FIG. 4 shows that tyrosine mutants exhibit reduced cytotoxic activity towards MDCK.2 cells, with data representing the means and standard deviations of three independent experiments performed in triplicates.

The % cytotoxic activity of the tyrosine mutants is based on the $CT_{50}$ fold-change relative to wild-type as determined in FIG. 4. The % binding activity of the tyrosine mutants is based on the fluorescent signal intensity relative to wild-type as determined in FIG. 5.

The Double Tyr Mutant Y43A/Y209A is Inactive

Figure 6:
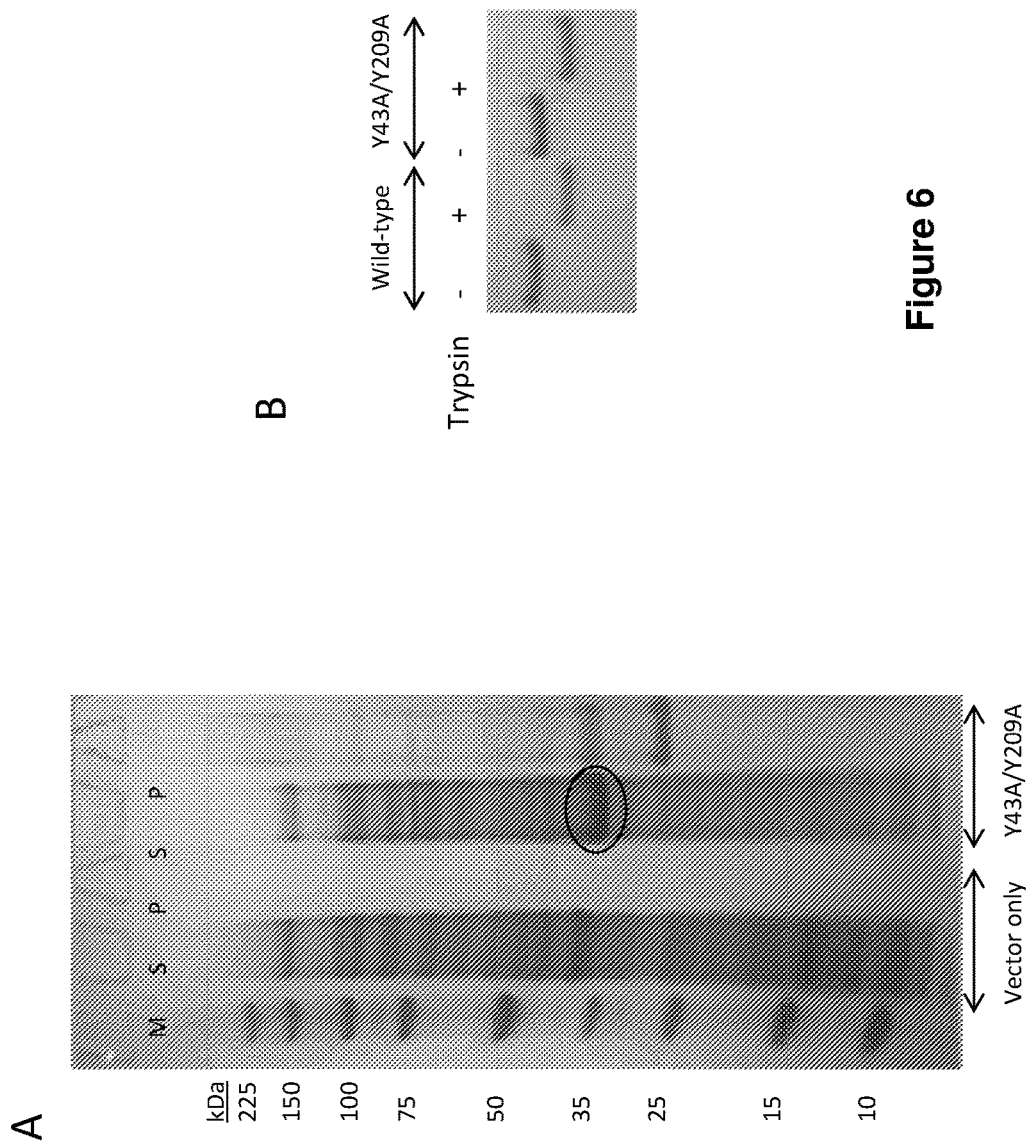
FIG. 6A shows Coomassie staining visualisation of recombinant Y43A/Y209A P-Etx expression, with insoluble (P) and soluble (S) fractions of post-induction bacterial protein extracts marked, which shows recombinant Y43A/Y209A expressed mainly in the soluble fraction (S), indicated by the presence of an intense ~35 kDa band (circled)
FIG. 6B shows wild-type and Y43A/Y209A purified recombinant epsilon prototoxins treated with trypsin, separated by SDS-PAGE and visualized by Coomassie staining.

To further evaluate the roles of the tyrosine residues in cell binding, a double Tyr mutant was generated combining the Y43A and Y209A mutations, termed Y43A/Y209A, which had the largest effect on reducing cytotoxic and binding activities of epsilon toxin. Y43A/Y209A was expressed and purified using the method developed for wild-type P-Etx. Similar to wild-type P-Etx, Y43A/Y209A expressed mostly in the soluble fraction and gave similar yields and purity to "wild-type" P-Etx (FIG. 6A). In addition, its trypsin digest profile was identical to that of "wild-type" P-Etx, indicating that combining mutations Y43A and Y209A does not affect the structure of the toxin (FIG. 6B). CD spectra analysis further confirmed that the double tyrosine mutant is adopting a predominantly β-sheet conformation, similar to "wild-type" P-Etx (data not shown).

Figure 7:
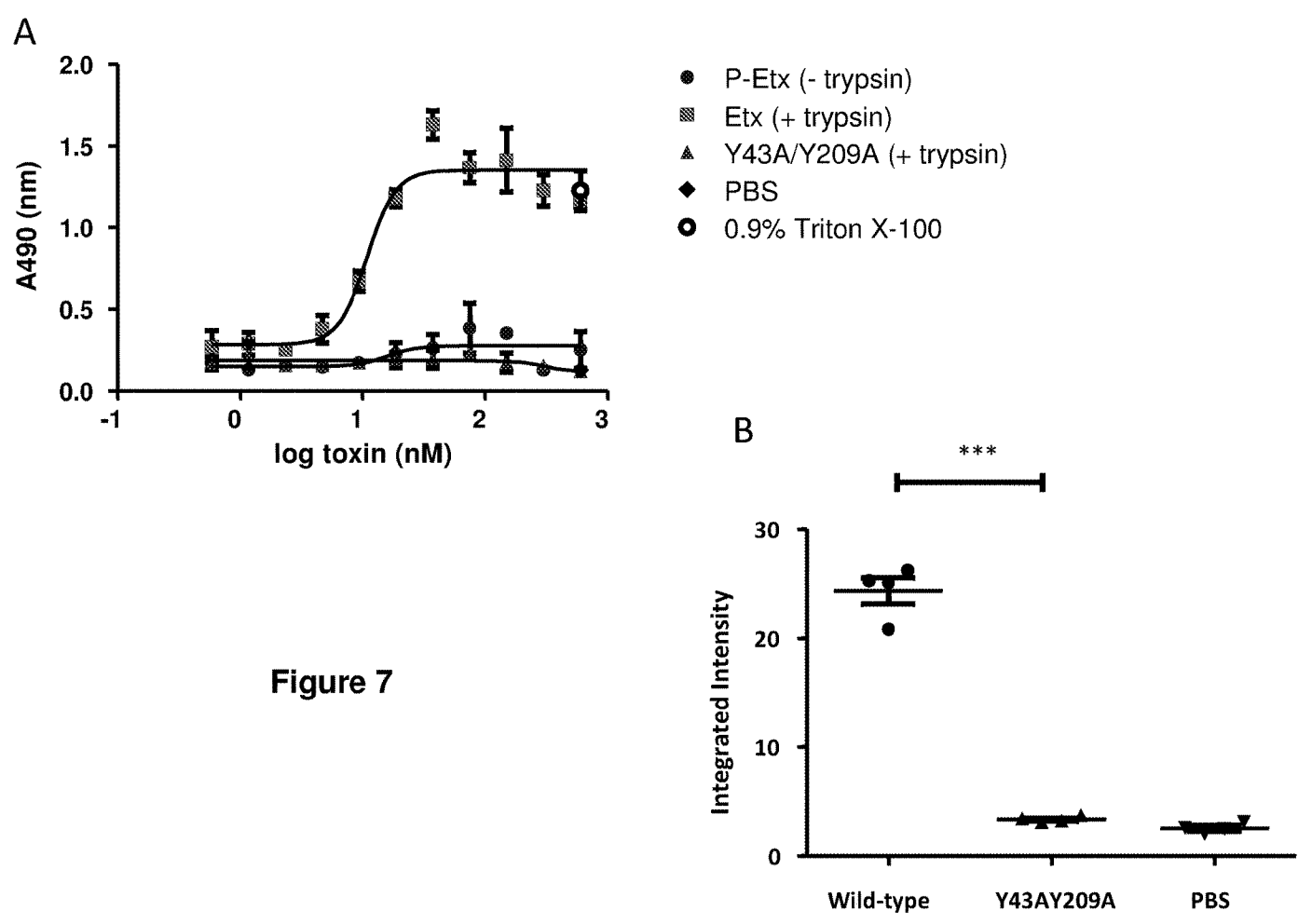

To determine the effect of Y43A/Y209A on cytotoxic activity of epsilon toxin, a 2-fold dilution series (ranging from 3 μM to 1.46 nM) of trypsin activated toxin was added to MDCK.2 cells seeded into 96-well plate as described in Materials and Methods. Following 3 h incubation at 37° C., the cell culture medium was harvested and cytotoxicity was measured using the LDH assay. The cytotoxic activity of trypsin activated Y43A/Y209A was compared to that of inactivated "wild-type" P-Etx. As shown in FIG. 7A, the cytotoxicity of trypsin activated Y43A/Y209A was equivalent to that of inactivated "wild-type" P-Etx, indicating that this mutant is inactive and combining mutations Y43A and Y209A has a cumulative effect on reducing cytotoxicity of Etx. To test if the loss of cytotoxic activity of Y43A/Y209A correlated with its inability to bind to MDCK.2 cells, on-cell Western studies were carried out using inactive prototoxin as described in Materials and Methods. As shown in FIG. 7B, the fluorescent signal of cells treated with Y43A/Y209A is equivalent to that of cells treated with PBS only, indicating that the apparent loss of cytotoxic activity of Y43A/Y209A is due to its inability to bind to cells.

Y43A/Y209A as Vaccine Candidate

Figure 8:
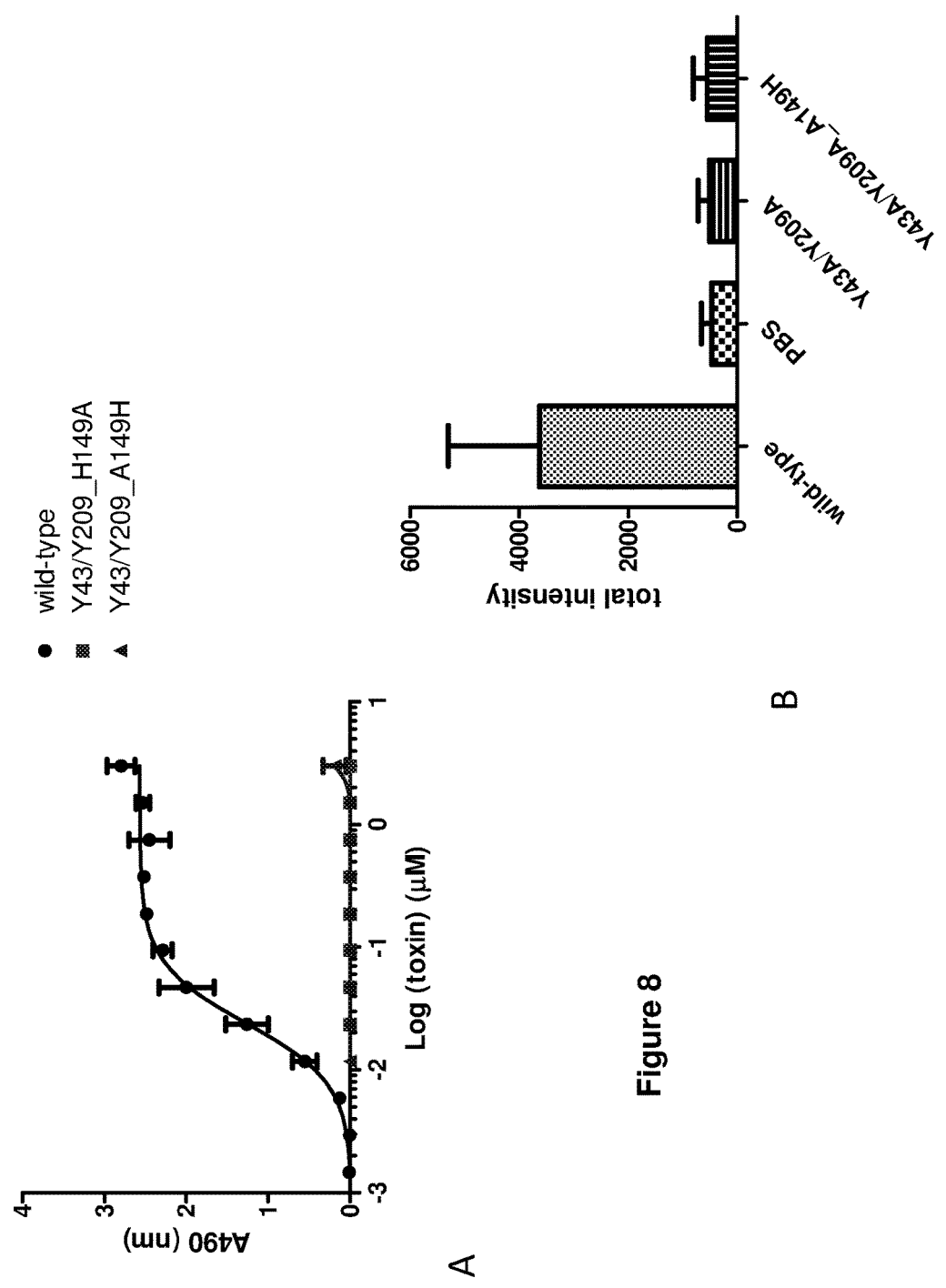

The inactive Y43A/Y209A mutant identified in this study also carries the H149A mutation so the toxin can be manipulated at ACGM level 2. To exclude the possibility that the double Tyr mutant is inactive because of a cumulative effect based on the presence of the H149A mutation, H149 was re-introduced into the double Tyr mutant by site directed mutagenesis to create the double mutant in the H149 wild type background. The cytotoxic activity and binding activity of Y43A/Y209A mutant in wild-type background (Y43A/Y209A_A149H) was identical to that of in H149A background (FIG. 8). This mutant was selected for further testing as a vaccine candidate.

Antiserum raised in rabbits was screened for its ability to protect cultured MDCK.2 cells against "wild-type" toxin induced cytotoxicity. Antiserum was also tested for its ability to block binding of wild-type P-Etx to MDCK.2 cells.

Discussion

The present data shows that Domain I of epsilon toxin plays a role in cell binding. The inventors' initial approach was to determine whether the loop regions in domain I are involved in cell binding, but they were unable to generate sufficient amount of soluble and stable protein from these loop deletion mutants for further assays. In contrast, all of the Tyr mutants were soluble and CD analysis indicated that these proteins were correctly folded, ruling out the possibility that the reduced cytotoxic activity of these mutants was due to their change in structure. The results confirm that domain I of Etx plays a role in cell binding and also that cytotoxicity cannot occur in the absence of binding.

Therefore, the results confirm that domain I of Etx plays a role in recognition of the cell surface. However, the identity of the cell surface receptor(s) for Etx is yet to be determined. Like aerolysin and PS, Etx appears to target the DRM domains on cell surfaces (Abrami & van Der Groot (1999) J. Cell Biol. vol. 147, 175-184). Both monomeric and heptameric Etx accumulate on these DRMs. Although the prototoxin is unable to heptamerise, it is able to bind to the same receptor as that used by activated toxin, indicating that heptamerisation is not a prerequisite for binding to target cells. It has been shown that changes in ganglioside content in DRMs affect the binding of the toxin (Shimamoto et al. (2005) Microbiol. Immunol. vol. 49, 245-253). However, there is no direct evidence of toxin-binding to ganglioside.

The inventors also identified a double Tyr mutant Y43A/Y209A with apparent lack of cytotoxic and binding activity and have shown that the presence of the H149A mutation does not contribute to its loss of activity. Y43A/Y209A in wild-type background (Y43A/Y209A_A149H) could form the basis of a recombinant vaccine against Etx-mediated enterotoxemia in animals. The presence of two mutations in Y43A/Y209A greatly reduces the risk of reversion to full activity compared to a recombinant protein with only a single mutation, making Y43A/Y209A an ideal vaccine candidate. In addition, recombinant vaccines offer low batch to batch variability compared the existing commercially available vaccine against Etx that is based on treating *C. perfringens* type D culture filtrate with formaldehyde.

In conclusion, the inventors have identified a distinct cluster of surface exposed Tyrosine residues in domain I of epsilon toxin that is critical for the interaction of Etx with the receptor on MDCK.2 cells, providing further evidence that Etx binding to cells is mediated via domain I. However, the identity of the receptor on the target cell remains to be elucidated. A recombinant Y43A/Y209A variant protein was also generated, that could be used to develop a more effective vaccine against Etx-mediated enterotoxemia in animals.

TABLE 2 primers used for site directed mutagenesis

| Amino acid change | SEQ ID NO | Primer sequence[a] |
|---|---|---|
| Y29A_F | 37 | CTTCTTATGATAATGTAGATACATTAATTGAGAAAGG AAGAGCGAATACAAAATATAATTACTTAAAGAGAATG GAAAAATATTA |

TABLE 2-continued primers used for site directed mutagenesis

| Amino acid change | SEQ ID NO | Primer sequence[a] |
|---|---|---|
| Y29A_R | 38 | TAATATTTTTCCATTCTCTTTAAGTAATTATATTTTG TATT<u>CGC</u>TCTTCCTTTCTCAATTAATGTATCTACATT ATCATAAGAAG |
| Y33A_F | 39 | GTAGATACATTAATTGAGAAAGGAAGATATAATACAA AA<u>GCG</u>AATTACTTAAAGAGAATGGAAAAATATTATCC TAATGCT |
| Y33A_R | 40 | AGCATTAGGATAATATTTTTCCATTCTCTTTAAGTAA TT<u>CGC</u>TTTTGTATTATATCTTCCTTTCTCAATTAATG TATCTAC |
| Y42A_F | 41 | AAAGGAAGATATAATACAAAATATAATTACTTAAAGA GAATGGAAAAA<u>GCG</u>TATCCTAATGCTATGGCATATTT TGATAA |
| Y42A_R | 42 | TTATCAAAATATGCCATAGCATTAGGATA<u>CGC</u>TTTTT CCATTCTCTTTAAGTAATTATATTTTGTATTATATCT TCCTTT |
| Y43A_F2 | 45 | GAAAGGAAGATATAATACAAAATATAATTACTTAAAG AGAATGGAAAAATAT<u>GCG</u>CCTAATGCTATGGCATATT TTGATAAGG |
| Y43A_R2 | 46 | CCTTATCAAAATATGCCATAGCATTAGG<u>CGC</u>ATATTT TTCCATTCTCTTTAAGTAATTATATTTTGTATTATAT CTTCCTTTC |
| Y49A_F | 47 | GAATGGAAAAATATTATCCTAATGCTATGGC<u>AGC</u>GTT TGATAAGGTTACTATAAATCCACAAGGAAA |
| Y49A_R | 48 | TTTCCTTGTGGATTTATAGTAACCTTATCAAA<u>CGC</u>TG CCATAGCATTAGGATAATATTTTTCCATTC |
| Y209A_F | 49 | GTGAATGGGGAGAGATACCTAGT<u>GCG</u>TTAGCTTTTCC TAGGGATGGTTA |
| Y209A_R | 50 | TAACCATCCCTAGGAAAAGCTAA<u>CGC</u>ACTAGGTATCT CTCCCCATTCAC |
| A149H_F | 51 | CAAATACAAATACAAATACTAATTCAAAAGAAATTAC T<u>CAT</u>AATGTCCCTTCACAAGATATACTAG |
| A149H_R | 52 | CTAGTATATCTTGTGAAGGGACATT<u>ATG</u>AGTAATTTC TTTTGAATTAGTATTTGTATTTGTATTTG |

[a]Underlined bases are the codons used for substitution. Amino acid numbering for Y mutations correspond to prototoxin with the N-terminal peptide sequence (corresponds to PDB 1UYJ; SEQ ID NO: 3).
Amino acid numbering for the A149H mutation corresponds to prototoxin without the N-terminal peptide sequence.

TABLE 3 identity of sequences included in application

| SEQ ID NO | Identity of sequence |
|---|---|
| 1 | full length epsilon toxin with Y43A and Y209A mutations |
| 2 | full length wild-type native epsilon toxin |
| 3 | sequence used to obtain crystal structure (PDB ID:1YUJ) |
| 4 | full length epsilon toxin with Y43A, Y209A and H149A mutations |
| 5 | trypsin activated wild-type recombinant epsilon toxin |
| 6 | trypsin activated recombinant epsilon toxin with Y43A and Y209A mutations |
| 7 | full length epsilon toxin with Y43A mutation |
| 8 | full length epsilon toxin with Y209A mutation |
| 9 | full length epsilon toxin with H149A mutation |
| 10 | full length epsilon toxin with Y43A and H149A mutations |
| 11 | full length epsilon toxin with Y209A and H149A mutations |
| 12 | full length recombinant epsilon toxin |
| 13 | full length recombinant epsilon toxin with Y43A mutation |
| 14 | full length recombinant epsilon toxin with Y209A mutation |
| 15 | full length recombinant epsilon toxin Y43A and Y209A mutation |
| 16 | full length recombinant epsilon toxin with H149A mutation |
| 17 | full length recombinant epsilon toxin with H149A and Y43A mutations |
| 18 | full length recombinant epsilon toxin with H149A and Y209A mutations |
| 19 | full length recombinant epsilon toxin with H149A, Y43A and Y209A mutations |
| 20 | trypsin activated wild-type recombinant epsilon toxin with Y43A mutation |
| 21 | trypsin activated wild-type recombinant epsilon toxin with Y209A mutation |
| 22 | trypsin activated recombinant epsilon toxin with H149A mutation |
| 23 | trypsin activated recombinant epsilon toxin with H149A and Y43A mutations |
| 24 | trypsin activated recombinant epsilon toxin with H149A and Y209A mutations |
| 25 | trypsin activated recombinant epsilon toxin with H149A, Y43A and Y209A mutations |
| 26 | native epsilon toxin without N-terminal peptide |
| 27 | native epsilon toxin without N-terminal peptide and with H149A mutation |
| 28 | recombinant epsilon toxin without PelB leader peptide |
| 29 | recombinant epsilon toxin without PelB leader peptide with H149A mutation |

TABLE 4

DNA sequences encoding for amino acid sequences

| DNA SEQ ID NO | Encoding for amino acid SEQ ID NO |
|---|---|
| 55 | 1 |
| 56 | 4 |
| 57 | 6 |
| 58 | 15 |
| 59 | 19 |
| 60 | 25 |

The invention claimed is:

1. An epsilon toxin epitope polypeptide comprising a sequence at least about 260 amino acids in length with at least 95% identity to SEQ ID NO:3 and having a mutation at position Y43, the polypeptide being capable of binding an antibody which binds to SEQ ID NO:5 and having reduced toxicity compared with the toxicity of SEQ ID NO:5.

2. The polypeptide according to claim 1 further comprising a mutation at position Y29, Y33, Y42, Y49 or Y209, as found in SEQ ID NO: 3.

3. The polypeptide according to claim 2 wherein the mutation is at position Y209.

4. The polypeptide according to claim 2 wherein amino acid Y is replaced with amino acid A.

5. The polypeptide according to claim 1, wherein the amino acid sequence further comprises RMEKYXPNAM (SEQ ID NO:33), or YNYLKRMEKYXPNAMAYFDK (SEQ ID NO:34), or GEIPSXLAFP (SEQ ID NO:35), or SGSEWGEIPSXLAFPRDGYK (SEQ ID NO:36), wherein "X" is any amino acid other than Y.

6. The polypeptide according to claim 1 wherein "X" is amino acid alanine.

7. The polypeptide according to claim 1 wherein the polypeptide is non-toxic.

8. The polypeptide according to claim 1, comprising an amino acid sequence selected from SEQ ID NO:1, 4, 6, 15, 19 or 25.

9. A composition comprising a polypeptide according to claim 1.

10. A kit comprising a polypeptide according to claim 1.

11. A method of reducing the risk of a subject developing a disease caused by *Clostridium perfringens*, by inducing an immune response through administering to the subject a protective amount of a polypeptide according to claim 1.

12. The method according to claim 11 wherein the subject is a sheep, pig, goat or a domestic cow.

13. The method according to claim 11 wherein the subject is a young animal selected from the group consisting of a lamb, a piglet, a goat kid and a calf.

14. The method according to claim 11 wherein the polypeptide further comprises RMEKYXPNAM (SEQ ID NO:33), or YNYLKRMEKYXPNAMAYFDK (SEQ ID NO:34), or GEIPSXLAFP (SEQ ID NO:35), or SGSEWGEIPSXLAFPRDGYK (SEQ ID NO:36), wherein "X" is any amino acid other than Y.

15. (New; Withdrawn) The method according to claim 11 wherein the disease is enterotoxemia.

* * * * *

SEQUENCE LISTING

```
<160> NUMBER OF SEQ ID NOS: 60

<210> SEQ ID NO 1
<211> LENGTH: 328
<212> TYPE: PRT
<213> ORGANISM: Artificial Sequence
<220> FEATURE:
<223> OTHER INFORMATION: Mutation sequence

<400> SEQUENCE: 1
```

```
Met Lys Lys Asn Leu Val Lys Ser Leu Ala Ile Ala Ser Ala Val Ile
1               5                   10                  15

Ser Ile Tyr Ser Ile Val Asn Ile Val Ser Pro Thr Asn Val Ile Ala
                20                  25                  30

Lys Glu Ile Ser Asn Thr Val Ser Asn Glu Met Ser Lys Lys Ala Ser
            35                  40                  45

Tyr Asp Asn Val Asp Thr Leu Ile Glu Lys Gly Arg Tyr Asn Thr Lys
 50                  55                  60

Tyr Asn Tyr Leu Lys Arg Met Glu Lys Tyr Ala Pro Asn Ala Met Ala
 65                  70                  75                  80

Tyr Phe Asp Lys Val Thr Ile Asn Pro Gln Gly Asn Asp Phe Tyr Ile
                85                  90                  95

Asn Asn Pro Lys Val Glu Leu Asp Gly Glu Pro Ser Met Asn Tyr Leu
            100                 105                 110

Glu Asp Val Tyr Val Gly Lys Ala Leu Leu Thr Asn Asp Thr Gln Gln
            115                 120                 125

Glu Gln Lys Leu Lys Ser Gln Ser Phe Thr Cys Lys Asn Thr Asp Thr
            130                 135                 140

Val Thr Ala Thr Thr Thr His Thr Val Gly Thr Ser Ile Gln Ala Thr
145                 150                 155                 160

Ala Lys Phe Thr Val Pro Phe Asn Glu Thr Gly Val Ser Leu Thr Thr
                165                 170                 175

Ser Tyr Ser Phe Ala Asn Thr Asn Thr Asn Thr Asn Ser Lys Glu Ile
                180                 185                 190

Thr His Asn Val Pro Ser Gln Asp Ile Leu Val Pro Ala Asn Thr Thr
            195                 200                 205

Val Glu Val Ile Ala Tyr Leu Lys Lys Val Asn Val Lys Gly Asn Val
            210                 215                 220

Lys Leu Val Gly Gln Val Ser Gly Ser Glu Trp Gly Glu Ile Pro Ser
225                 230                 235                 240

Ala Leu Ala Phe Pro Arg Asp Gly Tyr Lys Phe Ser Leu Ser Asp Thr
                245                 250                 255

Val Asn Lys Ser Asp Leu Asn Glu Asp Gly Thr Ile Asn Ile Asn Gly
            260                 265                 270

Lys Gly Asn Tyr Ser Ala Val Met Gly Asp Glu Leu Ile Val Lys Val
            275                 280                 285

Arg Asn Leu Asn Thr Asn Asn Val Gln Glu Tyr Val Ile Pro Val Asp
            290                 295                 300

Lys Lys Glu Lys Ser Asn Asp Ser Asn Ile Val Lys Tyr Arg Ser Leu
305                 310                 315                 320

Ser Ile Lys Ala Pro Gly Ile Lys
                325

<210> SEQ ID NO 2
<211> LENGTH: 328
<212> TYPE: PRT
<213> ORGANISM: Clostridium perfringens

<400> SEQUENCE: 2

Met Lys Lys Asn Leu Val Lys Ser Leu Ala Ile Ala Ser Ala Val Ile
1               5                   10                  15

Ser Ile Tyr Ser Ile Val Asn Ile Val Ser Pro Thr Asn Val Ile Ala
                20                  25                  30

Lys Glu Ile Ser Asn Thr Val Ser Asn Glu Met Ser Lys Lys Ala Ser
            35                  40                  45
```

Tyr Asp Asn Val Asp Thr Leu Ile Glu Lys Gly Arg Tyr Asn Thr Lys
             50                  55                  60

Tyr Asn Tyr Leu Lys Arg Met Glu Lys Tyr Tyr Pro Asn Ala Met Ala
 65                  70                  75                  80

Tyr Phe Asp Lys Val Thr Ile Asn Pro Gln Gly Asn Asp Phe Tyr Ile
                 85                  90                  95

Asn Asn Pro Lys Val Glu Leu Asp Gly Glu Pro Ser Met Asn Tyr Leu
                100                 105                 110

Glu Asp Val Tyr Val Gly Lys Ala Leu Leu Thr Asn Asp Thr Gln Gln
            115                 120                 125

Glu Gln Lys Leu Lys Ser Gln Ser Phe Thr Cys Lys Asn Thr Asp Thr
            130                 135                 140

Val Thr Ala Thr Thr Thr His Thr Val Gly Thr Ser Ile Gln Ala Thr
145                 150                 155                 160

Ala Lys Phe Thr Val Pro Phe Asn Glu Thr Gly Val Ser Leu Thr Thr
                165                 170                 175

Ser Tyr Ser Phe Ala Asn Thr Asn Thr Asn Thr Asn Ser Lys Glu Ile
                180                 185                 190

Thr His Asn Val Pro Ser Gln Asp Ile Leu Val Pro Ala Asn Thr Thr
            195                 200                 205

Val Glu Val Ile Ala Tyr Leu Lys Lys Val Asn Val Lys Gly Asn Val
210                 215                 220

Lys Leu Val Gly Gln Val Ser Gly Ser Glu Trp Gly Glu Ile Pro Ser
225                 230                 235                 240

Tyr Leu Ala Phe Pro Arg Asp Gly Tyr Lys Phe Ser Leu Ser Asp Thr
                245                 250                 255

Val Asn Lys Ser Asp Leu Asn Glu Asp Gly Thr Ile Asn Ile Asn Gly
            260                 265                 270

Lys Gly Asn Tyr Ser Ala Val Met Gly Asp Glu Leu Ile Val Lys Val
            275                 280                 285

Arg Asn Leu Asn Thr Asn Asn Val Gln Glu Tyr Val Ile Pro Val Asp
            290                 295                 300

Lys Lys Glu Lys Ser Asn Asp Ser Asn Ile Val Lys Tyr Arg Ser Leu
305                 310                 315                 320

Ser Ile Lys Ala Pro Gly Ile Lys
                325

<210> SEQ ID NO 3
<211> LENGTH: 296
<212> TYPE: PRT
<213> ORGANISM: Artificial Sequence
<220> FEATURE:
<223> OTHER INFORMATION: Crystallography sequence

<400> SEQUENCE: 3

Lys Glu Ile Ser Asn Thr Val Ser Asn Glu Met Ser Lys Lys Ala Ser
 1               5                  10                  15

Tyr Asp Asn Val Asp Thr Leu Ile Glu Lys Gly Arg Tyr Asn Thr Lys
                 20                  25                  30

Tyr Asn Tyr Leu Lys Arg Met Glu Lys Tyr Tyr Pro Asn Ala Met Ala
             35                  40                  45

Tyr Phe Asp Lys Val Thr Ile Asn Pro Gln Gly Asn Asp Phe Tyr Ile
         50                  55                  60

Asn Asn Pro Lys Val Glu Leu Asp Gly Glu Pro Ser Met Asn Tyr Leu
 65                  70                  75                  80

-continued

Glu Asp Val Tyr Val Gly Lys Ala Leu Leu Thr Asn Asp Thr Gln Gln
                85                  90                  95

Glu Gln Lys Leu Lys Ser Gln Ser Phe Thr Cys Lys Asn Thr Asp Thr
            100                 105                 110

Val Thr Ala Thr Thr Thr His Thr Val Gly Thr Ser Ile Gln Ala Thr
            115                 120                 125

Ala Lys Phe Thr Val Pro Phe Asn Glu Thr Gly Val Ser Leu Thr Thr
            130                 135                 140

Ser Tyr Ser Phe Ala Asn Thr Asn Thr Asn Thr Asn Ser Lys Glu Ile
145                 150                 155                 160

Thr His Asn Val Pro Ser Gln Asp Ile Leu Val Pro Ala Asn Thr Thr
                165                 170                 175

Val Glu Val Ile Ala Tyr Leu Lys Lys Val Asn Val Lys Gly Asn Val
            180                 185                 190

Lys Leu Val Gly Gln Val Ser Gly Ser Glu Trp Gly Glu Ile Pro Ser
            195                 200                 205

Tyr Leu Ala Phe Pro Arg Asp Gly Tyr Lys Phe Ser Leu Ser Asp Thr
            210                 215                 220

Val Asn Lys Ser Asp Leu Asn Glu Asp Gly Thr Ile Asn Ile Asn Gly
225                 230                 235                 240

Lys Gly Asn Tyr Ser Ala Val Met Gly Asp Glu Leu Ile Val Lys Val
                245                 250                 255

Arg Asn Leu Asn Thr Asn Asn Val Gln Glu Tyr Val Ile Pro Val Asp
                260                 265                 270

Lys Lys Glu Lys Ser Asn Asp Ser Asn Ile Val Lys Tyr Arg Ser Leu
            275                 280                 285

Ser Ile Lys Ala Pro Gly Ile Lys
            290                 295

<210> SEQ ID NO 4
<211> LENGTH: 328
<212> TYPE: PRT
<213> ORGANISM: Artificial Sequence
<220> FEATURE:
<223> OTHER INFORMATION: Mutation sequence

<400> SEQUENCE: 4

Met Lys Lys Asn Leu Val Lys Ser Leu Ala Ile Ala Ser Ala Val Ile
1               5                   10                  15

Ser Ile Tyr Ser Ile Val Asn Ile Val Ser Pro Thr Asn Val Ile Ala
            20                  25                  30

Lys Glu Ile Ser Asn Thr Val Ser Asn Glu Met Ser Lys Lys Ala Ser
            35                  40                  45

Tyr Asp Asn Val Asp Thr Leu Ile Glu Lys Gly Arg Tyr Asn Thr Lys
50                  55                  60

Tyr Asn Tyr Leu Lys Arg Met Glu Lys Tyr Ala Pro Asn Ala Met Ala
65                  70                  75                  80

Tyr Phe Asp Lys Val Thr Ile Asn Pro Gln Gly Asn Asp Phe Tyr Ile
                85                  90                  95

Asn Asn Pro Lys Val Glu Leu Asp Gly Glu Pro Ser Met Asn Tyr Leu
            100                 105                 110

Glu Asp Val Tyr Val Gly Lys Ala Leu Leu Thr Asn Asp Thr Gln Gln
            115                 120                 125

Glu Gln Lys Leu Lys Ser Gln Ser Phe Thr Cys Lys Asn Thr Asp Thr
            130                 135                 140

```
Val Thr Ala Thr Thr Thr His Thr Val Gly Thr Ser Ile Gln Ala Thr
145                 150                 155                 160

Ala Lys Phe Thr Val Pro Phe Asn Glu Thr Gly Val Ser Leu Thr Thr
            165                 170                 175

Ser Tyr Ser Phe Ala Asn Thr Asn Thr Asn Ser Lys Glu Ile
        180                 185                 190

Thr Ala Asn Val Pro Ser Gln Asp Ile Leu Val Pro Ala Asn Thr Thr
        195                 200                 205

Val Glu Val Ile Ala Tyr Leu Lys Lys Val Asn Val Lys Gly Asn Val
    210                 215                 220

Lys Leu Val Gly Gln Val Ser Gly Ser Glu Trp Gly Glu Ile Pro Ser
225                 230                 235                 240

Ala Leu Ala Phe Pro Arg Asp Gly Tyr Lys Phe Ser Leu Ser Asp Thr
                245                 250                 255

Val Asn Lys Ser Asp Leu Asn Glu Asp Gly Thr Ile Asn Ile Asn Gly
            260                 265                 270

Lys Gly Asn Tyr Ser Ala Val Met Gly Asp Glu Leu Ile Val Lys Val
        275                 280                 285

Arg Asn Leu Asn Thr Asn Asn Val Gln Glu Tyr Val Ile Pro Val Asp
290                 295                 300

Lys Lys Glu Lys Ser Asn Asp Ser Asn Ile Val Lys Tyr Arg Ser Leu
305                 310                 315                 320

Ser Ile Lys Ala Pro Gly Ile Lys
                325

<210> SEQ ID NO 5
<211> LENGTH: 263
<212> TYPE: PRT
<213> ORGANISM: Clostridium perfringens

<400> SEQUENCE: 5

Met Gly Lys Ala Ser Tyr Asp Asn Val Asp Thr Leu Ile Glu Lys Gly
1               5                   10                  15

Arg Tyr Asn Thr Lys Tyr Asn Tyr Leu Lys Arg Met Glu Lys Tyr Tyr
            20                  25                  30

Pro Asn Ala Met Ala Tyr Phe Asp Lys Val Thr Ile Asn Pro Gln Gly
        35                  40                  45

Asn Asp Phe Tyr Ile Asn Asn Pro Lys Val Glu Leu Asp Gly Glu Pro
    50                  55                  60

Ser Met Asn Tyr Leu Glu Asp Val Tyr Val Gly Lys Ala Leu Leu Thr
65                  70                  75                  80

Asn Asp Thr Gln Gln Glu Gln Lys Leu Lys Ser Gln Ser Phe Thr Cys
                85                  90                  95

Lys Asn Thr Asp Thr Val Thr Ala Thr Thr His Thr Val Gly Thr
            100                 105                 110

Ser Ile Gln Ala Thr Ala Lys Phe Thr Val Pro Phe Asn Glu Thr Gly
        115                 120                 125

Val Ser Leu Thr Thr Ser Tyr Ser Phe Ala Asn Thr Asn Thr Asn Thr
    130                 135                 140

Asn Ser Lys Glu Ile Thr His Asn Val Pro Ser Gln Asp Ile Leu Val
145                 150                 155                 160

Pro Ala Asn Thr Thr Val Glu Val Ile Ala Tyr Leu Lys Lys Val Asn
                165                 170                 175

Val Lys Gly Asn Val Lys Leu Val Gly Gln Val Ser Gly Ser Glu Trp
```

```
                180              185              190
Gly Glu Ile Pro Ser Tyr Leu Ala Phe Pro Arg Asp Gly Tyr Lys Phe
            195              200              205
Ser Leu Ser Asp Thr Val Asn Lys Ser Asp Leu Asn Glu Asp Gly Thr
        210              215              220
Ile Asn Ile Asn Gly Lys Gly Asn Tyr Ser Ala Val Met Gly Asp Glu
225              230              235              240
Leu Ile Val Lys Val Arg Asn Leu Asn Thr Asn Asn Val Gln Glu Tyr
                245              250              255
Val Ile Pro Val Asp Lys Lys
            260

<210> SEQ ID NO 6
<211> LENGTH: 263
<212> TYPE: PRT
<213> ORGANISM: Artificial Sequence
<220> FEATURE:
<223> OTHER INFORMATION: Mutation sequence

<400> SEQUENCE: 6

Met Gly Lys Ala Ser Tyr Asp Asn Val Asp Thr Leu Ile Glu Lys Gly
1               5                   10                  15
Arg Tyr Asn Thr Lys Tyr Asn Tyr Leu Lys Arg Met Glu Lys Tyr Ala
                20                  25                  30
Pro Asn Ala Met Ala Tyr Phe Asp Lys Val Thr Ile Asn Pro Gln Gly
            35                  40                  45
Asn Asp Phe Tyr Ile Asn Asn Pro Lys Val Glu Leu Asp Gly Glu Pro
        50                  55                  60
Ser Met Asn Tyr Leu Glu Asp Val Tyr Val Gly Lys Ala Leu Leu Thr
65                  70                  75                  80
Asn Asp Thr Gln Gln Glu Gln Lys Leu Lys Ser Gln Ser Phe Thr Cys
                85                  90                  95
Lys Asn Thr Asp Thr Val Thr Ala Thr Thr His Thr Val Gly Thr
                100                 105                 110
Ser Ile Gln Ala Thr Ala Lys Phe Thr Val Pro Phe Asn Glu Thr Gly
            115                 120                 125
Val Ser Leu Thr Thr Ser Tyr Ser Phe Ala Asn Thr Asn Thr Asn Thr
        130                 135                 140
Asn Ser Lys Glu Ile Thr His Asn Val Pro Ser Gln Asp Ile Leu Val
145                 150                 155                 160
Pro Ala Asn Thr Thr Val Glu Val Ile Ala Tyr Leu Lys Lys Val Asn
                165                 170                 175
Val Lys Gly Asn Val Lys Leu Val Gly Gln Val Ser Gly Ser Glu Trp
            180                 185                 190
Gly Glu Ile Pro Ser Ala Leu Ala Phe Pro Arg Asp Gly Tyr Lys Phe
        195                 200                 205
Ser Leu Ser Asp Thr Val Asn Lys Ser Asp Leu Asn Glu Asp Gly Thr
    210                 215                 220
Ile Asn Ile Asn Gly Lys Gly Asn Tyr Ser Ala Val Met Gly Asp Glu
225                 230                 235                 240
Leu Ile Val Lys Val Arg Asn Leu Asn Thr Asn Asn Val Gln Glu Tyr
                245                 250                 255
Val Ile Pro Val Asp Lys Lys
            260
```

<210> SEQ ID NO 7
<211> LENGTH: 328
<212> TYPE: PRT
<213> ORGANISM: Artificial Sequence
<220> FEATURE:
<223> OTHER INFORMATION: Mutation sequence

<400> SEQUENCE: 7

```
Met Lys Lys Asn Leu Val Lys Ser Leu Ala Ile Ala Ser Ala Val Ile
1               5                   10                  15

Ser Ile Tyr Ser Ile Val Asn Ile Val Ser Pro Thr Asn Val Ile Ala
            20                  25                  30

Lys Glu Ile Ser Asn Thr Val Ser Asn Glu Met Ser Lys Lys Ala Ser
        35                  40                  45

Tyr Asp Asn Val Asp Thr Leu Ile Glu Lys Gly Arg Tyr Asn Thr Lys
    50                  55                  60

Tyr Asn Tyr Leu Lys Arg Met Glu Lys Tyr Ala Pro Asn Ala Met Ala
65              70                  75                  80

Tyr Phe Asp Lys Val Thr Ile Asn Pro Gln Gly Asn Asp Phe Tyr Ile
                85                  90                  95

Asn Asn Pro Lys Val Glu Leu Asp Gly Glu Pro Ser Met Asn Tyr Leu
            100                 105                 110

Glu Asp Val Tyr Val Gly Lys Ala Leu Leu Thr Asn Asp Thr Gln Gln
        115                 120                 125

Glu Gln Lys Leu Lys Ser Gln Ser Phe Thr Cys Lys Asn Thr Asp Thr
    130                 135                 140

Val Thr Ala Thr Thr His Thr Val Gly Thr Ser Ile Gln Ala Thr
145                 150                 155                 160

Ala Lys Phe Thr Val Pro Phe Asn Glu Thr Gly Val Ser Leu Thr Thr
                165                 170                 175

Ser Tyr Ser Phe Ala Asn Thr Asn Thr Asn Ser Lys Glu Ile
            180                 185                 190

Thr His Asn Val Pro Ser Gln Asp Ile Leu Val Pro Ala Asn Thr Thr
        195                 200                 205

Val Glu Val Ile Ala Tyr Leu Lys Lys Val Asn Val Lys Gly Asn Val
    210                 215                 220

Lys Leu Val Gly Gln Val Ser Gly Ser Glu Trp Gly Glu Ile Pro Ser
225                 230                 235                 240

Tyr Leu Ala Phe Pro Arg Asp Gly Tyr Lys Phe Ser Leu Ser Asp Thr
                245                 250                 255

Val Asn Lys Ser Asp Leu Asn Glu Asp Gly Thr Ile Asn Ile Asn Gly
            260                 265                 270

Lys Gly Asn Tyr Ser Ala Val Met Gly Asp Glu Leu Ile Val Lys Val
        275                 280                 285

Arg Asn Leu Asn Thr Asn Asn Val Gln Glu Tyr Val Ile Pro Val Asp
    290                 295                 300

Lys Lys Glu Lys Ser Asn Asp Ser Asn Ile Val Lys Tyr Arg Ser Leu
305                 310                 315                 320

Ser Ile Lys Ala Pro Gly Ile Lys
                325
```

<210> SEQ ID NO 8
<211> LENGTH: 328
<212> TYPE: PRT
<213> ORGANISM: Artificial Sequence
<220> FEATURE:
<223> OTHER INFORMATION: Mutation sequence

<400> SEQUENCE: 8

```
Met Lys Lys Asn Leu Val Lys Ser Leu Ala Ile Ala Ser Ala Val Ile
1               5                   10                  15

Ser Ile Tyr Ser Ile Val Asn Ile Val Ser Pro Thr Asn Val Ile Ala
                20                  25                  30

Lys Glu Ile Ser Asn Thr Val Ser Asn Glu Met Ser Lys Lys Ala Ser
            35                  40                  45

Tyr Asp Asn Val Asp Thr Leu Ile Glu Lys Gly Arg Tyr Asn Thr Lys
    50                  55                  60

Tyr Asn Tyr Leu Lys Arg Met Glu Lys Tyr Tyr Pro Asn Ala Met Ala
65                  70                  75                  80

Tyr Phe Asp Lys Val Thr Ile Asn Pro Gln Gly Asn Asp Phe Tyr Ile
                85                  90                  95

Asn Asn Pro Lys Val Glu Leu Asp Gly Glu Pro Ser Met Asn Tyr Leu
            100                 105                 110

Glu Asp Val Tyr Val Gly Lys Ala Leu Leu Thr Asn Asp Thr Gln Gln
    115                 120                 125

Glu Gln Lys Leu Lys Ser Gln Ser Phe Thr Cys Lys Asn Thr Asp Thr
130                 135                 140

Val Thr Ala Thr Thr His Thr Val Gly Thr Ser Ile Gln Ala Thr
145                 150                 155                 160

Ala Lys Phe Thr Val Pro Phe Asn Glu Thr Gly Val Ser Leu Thr Thr
                165                 170                 175

Ser Tyr Ser Phe Ala Asn Thr Asn Thr Asn Ser Lys Glu Ile
            180                 185                 190

Thr His Asn Val Pro Ser Gln Asp Ile Leu Val Pro Ala Asn Thr Thr
    195                 200                 205

Val Glu Val Ile Ala Tyr Leu Lys Lys Val Asn Val Lys Gly Asn Val
210                 215                 220

Lys Leu Val Gly Gln Val Ser Gly Ser Glu Trp Gly Glu Ile Pro Ser
225                 230                 235                 240

Ala Leu Ala Phe Pro Arg Asp Gly Tyr Lys Phe Ser Leu Ser Asp Thr
                245                 250                 255

Val Asn Lys Ser Asp Leu Asn Glu Asp Gly Thr Ile Asn Ile Asn Gly
            260                 265                 270

Lys Gly Asn Tyr Ser Ala Val Met Gly Asp Glu Leu Ile Val Lys Val
    275                 280                 285

Arg Asn Leu Asn Thr Asn Asn Val Gln Glu Tyr Val Ile Pro Val Asp
290                 295                 300

Lys Lys Glu Lys Ser Asn Asp Ser Asn Ile Val Lys Tyr Arg Ser Leu
305                 310                 315                 320

Ser Ile Lys Ala Pro Gly Ile Lys
                325
```

<210> SEQ ID NO 9
<211> LENGTH: 328
<212> TYPE: PRT
<213> ORGANISM: Artificial Sequence
<220> FEATURE:
<223> OTHER INFORMATION: Mutation sequence

<400> SEQUENCE: 9

```
Met Lys Lys Asn Leu Val Lys Ser Leu Ala Ile Ala Ser Ala Val Ile
1               5                   10                  15
```

```
Ser Ile Tyr Ser Ile Val Asn Ile Val Ser Pro Thr Asn Val Ile Ala
            20                  25                  30

Lys Glu Ile Ser Asn Thr Val Ser Asn Glu Met Ser Lys Lys Ala Ser
        35                  40                  45

Tyr Asp Asn Val Asp Thr Leu Ile Glu Lys Gly Arg Tyr Asn Thr Lys
 50                  55                  60

Tyr Asn Tyr Leu Lys Arg Met Glu Lys Tyr Tyr Pro Asn Ala Met Ala
 65                  70                  75                  80

Tyr Phe Asp Lys Val Thr Ile Asn Pro Gln Gly Asn Asp Phe Tyr Ile
                85                  90                  95

Asn Asn Pro Lys Val Glu Leu Asp Gly Glu Pro Ser Met Asn Tyr Leu
            100                 105                 110

Glu Asp Val Tyr Val Gly Lys Ala Leu Leu Thr Asn Asp Thr Gln Gln
        115                 120                 125

Glu Gln Lys Leu Lys Ser Gln Ser Phe Thr Cys Lys Asn Thr Asp Thr
130                 135                 140

Val Thr Ala Thr Thr His Thr Val Gly Thr Ser Ile Gln Ala Thr
145                 150                 155                 160

Ala Lys Phe Thr Val Pro Phe Asn Glu Thr Gly Val Ser Leu Thr Thr
                165                 170                 175

Ser Tyr Ser Phe Ala Asn Thr Asn Thr Asn Thr Asn Ser Lys Glu Ile
            180                 185                 190

Thr Ala Asn Val Pro Ser Gln Asp Ile Leu Val Pro Ala Asn Thr Thr
        195                 200                 205

Val Glu Val Ile Ala Tyr Leu Lys Lys Val Asn Val Lys Gly Asn Val
210                 215                 220

Lys Leu Val Gly Gln Val Ser Gly Ser Glu Trp Gly Glu Ile Pro Ser
225                 230                 235                 240

Tyr Leu Ala Phe Pro Arg Asp Gly Tyr Lys Phe Ser Leu Ser Asp Thr
                245                 250                 255

Val Asn Lys Ser Asp Leu Asn Glu Asp Gly Thr Ile Asn Ile Asn Gly
            260                 265                 270

Lys Gly Asn Tyr Ser Ala Val Met Gly Asp Glu Leu Ile Val Lys Val
        275                 280                 285

Arg Asn Leu Asn Thr Asn Asn Val Gln Glu Tyr Val Ile Pro Val Asp
290                 295                 300

Lys Lys Glu Lys Ser Asn Asp Ser Asn Ile Val Lys Tyr Arg Ser Leu
305                 310                 315                 320

Ser Ile Lys Ala Pro Gly Ile Lys
                325

<210> SEQ ID NO 10
<211> LENGTH: 328
<212> TYPE: PRT
<213> ORGANISM: Artificial Sequence
<220> FEATURE:
<223> OTHER INFORMATION: Mutation sequence

<400> SEQUENCE: 10

Met Lys Lys Asn Leu Val Lys Ser Leu Ala Ile Ala Ser Ala Val Ile
1               5                   10                  15

Ser Ile Tyr Ser Ile Val Asn Ile Val Ser Pro Thr Asn Val Ile Ala
            20                  25                  30

Lys Glu Ile Ser Asn Thr Val Ser Asn Glu Met Ser Lys Lys Ala Ser
        35                  40                  45
```

```
Tyr Asp Asn Val Asp Thr Leu Ile Glu Lys Gly Arg Tyr Asn Thr Lys
 50                  55                  60

Tyr Asn Tyr Leu Lys Arg Met Glu Lys Tyr Ala Pro Asn Ala Met Ala
 65                  70                  75                  80

Tyr Phe Asp Lys Val Thr Ile Asn Pro Gln Gly Asn Asp Phe Tyr Ile
                 85                  90                  95

Asn Asn Pro Lys Val Glu Leu Asp Gly Glu Pro Ser Met Asn Tyr Leu
            100                 105                 110

Glu Asp Val Tyr Val Gly Lys Ala Leu Leu Thr Asn Asp Thr Gln Gln
            115                 120                 125

Glu Gln Lys Leu Lys Ser Gln Ser Phe Thr Cys Lys Asn Thr Asp Thr
130                 135                 140

Val Thr Ala Thr Thr His Thr Val Gly Thr Ser Ile Gln Ala Thr
145                 150                 155                 160

Ala Lys Phe Thr Val Pro Phe Asn Glu Thr Gly Val Ser Leu Thr Thr
                165                 170                 175

Ser Tyr Ser Phe Ala Asn Thr Asn Thr Asn Ser Lys Glu Ile
            180                 185                 190

Thr Ala Asn Val Pro Ser Gln Asp Ile Leu Val Pro Ala Asn Thr Thr
            195                 200                 205

Val Glu Val Ile Ala Tyr Leu Lys Lys Val Asn Val Lys Gly Asn Val
210                 215                 220

Lys Leu Val Gly Gln Val Ser Gly Ser Glu Trp Gly Glu Ile Pro Ser
225                 230                 235                 240

Tyr Leu Ala Phe Pro Arg Asp Gly Tyr Lys Phe Ser Leu Ser Asp Thr
                245                 250                 255

Val Asn Lys Ser Asp Leu Asn Glu Asp Gly Thr Ile Asn Ile Asn Gly
            260                 265                 270

Lys Gly Asn Tyr Ser Ala Val Met Gly Asp Glu Leu Ile Val Lys Val
            275                 280                 285

Arg Asn Leu Asn Thr Asn Asn Val Gln Glu Tyr Val Ile Pro Val Asp
290                 295                 300

Lys Lys Glu Lys Ser Asn Asp Ser Asn Ile Val Lys Tyr Arg Ser Leu
305                 310                 315                 320

Ser Ile Lys Ala Pro Gly Ile Lys
            325

<210> SEQ ID NO 11
<211> LENGTH: 328
<212> TYPE: PRT
<213> ORGANISM: Artificial Sequence
<220> FEATURE:
<223> OTHER INFORMATION: Mutation sequence

<400> SEQUENCE: 11

Met Lys Lys Asn Leu Val Lys Ser Leu Ala Ile Ala Ser Ala Val Ile
 1               5                  10                  15

Ser Ile Tyr Ser Ile Val Asn Ile Val Ser Pro Thr Asn Val Ile Ala
                 20                  25                  30

Lys Glu Ile Ser Asn Thr Val Ser Asn Glu Met Ser Lys Lys Ala Ser
             35                  40                  45

Tyr Asp Asn Val Asp Thr Leu Ile Glu Lys Gly Arg Tyr Asn Thr Lys
 50                  55                  60

Tyr Asn Tyr Leu Lys Arg Met Glu Lys Tyr Tyr Pro Asn Ala Met Ala
 65                  70                  75                  80
```

```
Tyr Phe Asp Lys Val Thr Ile Asn Pro Gln Gly Asn Asp Phe Tyr Ile
                85                  90                  95

Asn Asn Pro Lys Val Glu Leu Asp Gly Glu Pro Ser Met Asn Tyr Leu
            100                 105                 110

Glu Asp Val Tyr Val Gly Lys Ala Leu Leu Thr Asn Asp Thr Gln Gln
            115                 120                 125

Glu Gln Lys Leu Lys Ser Gln Ser Phe Thr Cys Lys Asn Thr Asp Thr
130                 135                 140

Val Thr Ala Thr Thr Thr His Thr Val Gly Thr Ser Ile Gln Ala Thr
145                 150                 155                 160

Ala Lys Phe Thr Val Pro Phe Asn Glu Thr Gly Val Ser Leu Thr Thr
                165                 170                 175

Ser Tyr Ser Phe Ala Asn Thr Asn Thr Asn Thr Asn Ser Lys Glu Ile
            180                 185                 190

Thr Ala Asn Val Pro Ser Gln Asp Ile Leu Val Pro Ala Asn Thr Thr
            195                 200                 205

Val Glu Val Ile Ala Tyr Leu Lys Lys Val Asn Val Lys Gly Asn Val
210                 215                 220

Lys Leu Val Gly Gln Val Ser Gly Ser Glu Trp Gly Glu Ile Pro Ser
225                 230                 235                 240

Ala Leu Ala Phe Pro Arg Asp Gly Tyr Lys Phe Ser Leu Ser Asp Thr
                245                 250                 255

Val Asn Lys Ser Asp Leu Asn Glu Asp Gly Thr Ile Asn Ile Asn Gly
            260                 265                 270

Lys Gly Asn Tyr Ser Ala Val Met Gly Asp Glu Leu Ile Val Lys Val
            275                 280                 285

Arg Asn Leu Asn Thr Asn Asn Val Gln Glu Tyr Val Ile Pro Val Asp
290                 295                 300

Lys Lys Glu Lys Ser Asn Asp Ser Asn Ile Val Lys Tyr Arg Ser Leu
305                 310                 315                 320

Ser Ile Lys Ala Pro Gly Ile Lys
                325

<210> SEQ ID NO 12
<211> LENGTH: 315
<212> TYPE: PRT
<213> ORGANISM: Artificial Sequence
<220> FEATURE:
<223> OTHER INFORMATION: Recombinant sequence

<400> SEQUENCE: 12

Met Lys Tyr Leu Leu Pro Thr Ala Ala Ala Gly Leu Leu Leu Leu Ala
1               5                   10                  15

Ala Gln Pro Ala Met Ala Met Gly Lys Ala Ser Tyr Asp Asn Val Asp
                20                  25                  30

Thr Leu Ile Glu Lys Gly Arg Tyr Asn Thr Lys Tyr Asn Tyr Leu Lys
            35                  40                  45

Arg Met Glu Lys Tyr Tyr Pro Asn Ala Met Ala Tyr Phe Asp Lys Val
50                  55                  60

Thr Ile Asn Pro Gln Gly Asn Asp Phe Tyr Ile Asn Asn Pro Lys Val
65                  70                  75                  80

Glu Leu Asp Gly Glu Pro Ser Met Asn Tyr Leu Glu Asp Val Tyr Val
                85                  90                  95

Gly Lys Ala Leu Leu Thr Asn Asp Thr Gln Gln Glu Gln Lys Leu Lys
            100                 105                 110
```

```
Ser Gln Ser Phe Thr Cys Lys Asn Thr Asp Thr Val Thr Ala Thr Thr
            115                 120                 125
Thr His Thr Val Gly Thr Ser Ile Gln Ala Thr Ala Lys Phe Thr Val
        130                 135                 140
Pro Phe Asn Glu Thr Gly Val Ser Leu Thr Thr Ser Tyr Ser Phe Ala
145                 150                 155                 160
Asn Thr Asn Thr Asn Thr Asn Ser Lys Glu Ile Thr His Asn Val Pro
                165                 170                 175
Ser Gln Asp Ile Leu Val Pro Ala Asn Thr Thr Val Glu Val Ile Ala
            180                 185                 190
Tyr Leu Lys Lys Val Asn Val Lys Gly Asn Val Lys Leu Val Gly Gln
        195                 200                 205
Val Ser Gly Ser Glu Trp Gly Glu Ile Pro Ser Tyr Leu Ala Phe Pro
210                 215                 220
Arg Asp Gly Tyr Lys Phe Ser Leu Ser Asp Thr Val Asn Lys Ser Asp
225                 230                 235                 240
Leu Asn Glu Asp Gly Thr Ile Asn Ile Asn Gly Lys Gly Asn Tyr Ser
                245                 250                 255
Ala Val Met Gly Asp Glu Leu Ile Val Lys Val Arg Asn Leu Asn Thr
            260                 265                 270
Asn Asn Val Gln Glu Tyr Val Ile Pro Val Asp Lys Lys Glu Lys Ser
        275                 280                 285
Asn Asp Ser Asn Ile Val Lys Tyr Arg Ser Leu Tyr Ile Lys Ala Pro
290                 295                 300
Gly Ile Lys Leu Glu His His His His His
305                 310                 315
```

<210> SEQ ID NO 13
<211> LENGTH: 315
<212> TYPE: PRT
<213> ORGANISM: Artificial Sequence
<220> FEATURE:
<223> OTHER INFORMATION: Recombinant mutation sequence

<400> SEQUENCE: 13

```
Met Lys Tyr Leu Leu Pro Thr Ala Ala Ala Gly Leu Leu Leu Leu Ala
1               5                   10                  15
Ala Gln Pro Ala Met Ala Met Gly Lys Ala Ser Tyr Asp Asn Val Asp
            20                  25                  30
Thr Leu Ile Glu Lys Gly Arg Tyr Asn Thr Lys Tyr Asn Tyr Leu Lys
        35                  40                  45
Arg Met Glu Lys Tyr Ala Pro Asn Ala Met Ala Tyr Phe Asp Lys Val
50                  55                  60
Thr Ile Asn Pro Gln Gly Asn Asp Phe Tyr Ile Asn Asn Pro Lys Val
65                  70                  75                  80
Glu Leu Asp Gly Glu Pro Ser Met Asn Tyr Leu Glu Asp Val Tyr Val
                85                  90                  95
Gly Lys Ala Leu Leu Thr Asn Asp Thr Gln Glu Gln Lys Leu Lys
            100                 105                 110
Ser Gln Ser Phe Thr Cys Lys Asn Thr Asp Thr Val Thr Ala Thr Thr
            115                 120                 125
Thr His Thr Val Gly Thr Ser Ile Gln Ala Thr Ala Lys Phe Thr Val
        130                 135                 140
Pro Phe Asn Glu Thr Gly Val Ser Leu Thr Thr Ser Tyr Ser Phe Ala
145                 150                 155                 160
```

```
Asn Thr Asn Thr Asn Thr Asn Ser Lys Glu Ile Thr His Asn Val Pro
                165                 170                 175

Ser Gln Asp Ile Leu Val Pro Ala Asn Thr Thr Val Glu Val Ile Ala
            180                 185                 190

Tyr Leu Lys Lys Val Asn Val Lys Gly Asn Val Lys Leu Val Gly Gln
        195                 200                 205

Val Ser Gly Ser Glu Trp Gly Glu Ile Pro Ser Tyr Leu Ala Phe Pro
210                 215                 220

Arg Asp Gly Tyr Lys Phe Ser Leu Ser Asp Thr Val Asn Lys Ser Asp
225                 230                 235                 240

Leu Asn Glu Asp Gly Thr Ile Asn Ile Asn Gly Lys Gly Asn Tyr Ser
                245                 250                 255

Ala Val Met Gly Asp Glu Leu Ile Val Lys Val Arg Asn Leu Asn Thr
            260                 265                 270

Asn Asn Val Gln Glu Tyr Val Ile Pro Val Asp Lys Lys Glu Lys Ser
        275                 280                 285

Asn Asp Ser Asn Ile Val Lys Tyr Arg Ser Leu Tyr Ile Lys Ala Pro
290                 295                 300

Gly Ile Lys Leu Glu His His His His His His
305                 310                 315

<210> SEQ ID NO 14
<211> LENGTH: 315
<212> TYPE: PRT
<213> ORGANISM: Artificial Sequence
<220> FEATURE:
<223> OTHER INFORMATION: Recombinant mutation sequence

<400> SEQUENCE: 14

Met Lys Tyr Leu Leu Pro Thr Ala Ala Gly Leu Leu Leu Leu Ala
1               5                   10                  15

Ala Gln Pro Ala Met Ala Met Gly Lys Ala Ser Tyr Asp Asn Val Asp
            20                  25                  30

Thr Leu Ile Glu Lys Gly Arg Tyr Asn Thr Lys Tyr Asn Tyr Leu Lys
        35                  40                  45

Arg Met Glu Lys Tyr Tyr Pro Asn Ala Met Ala Tyr Phe Asp Lys Val
50                  55                  60

Thr Ile Asn Pro Gln Gly Asn Asp Phe Tyr Ile Asn Asn Pro Lys Val
65                  70                  75                  80

Glu Leu Asp Gly Glu Pro Ser Met Asn Tyr Leu Glu Asp Val Tyr Val
                85                  90                  95

Gly Lys Ala Leu Leu Thr Asn Asp Thr Gln Glu Gln Lys Leu Lys
            100                 105                 110

Ser Gln Ser Phe Thr Cys Lys Asn Thr Asp Thr Val Thr Ala Thr Thr
        115                 120                 125

Thr His Thr Val Gly Thr Ser Ile Gln Ala Thr Ala Lys Phe Thr Val
130                 135                 140

Pro Phe Asn Glu Thr Gly Val Ser Leu Thr Thr Ser Tyr Ser Phe Ala
145                 150                 155                 160

Asn Thr Asn Thr Asn Thr Asn Ser Lys Glu Ile Thr His Asn Val Pro
                165                 170                 175

Ser Gln Asp Ile Leu Val Pro Ala Asn Thr Thr Val Glu Val Ile Ala
            180                 185                 190

Tyr Leu Lys Lys Val Asn Val Lys Gly Asn Val Lys Leu Val Gly Gln
        195                 200                 205
```

```
Val Ser Gly Ser Glu Trp Gly Glu Ile Pro Ser Ala Leu Ala Phe Pro
    210                 215                 220

Arg Asp Gly Tyr Lys Phe Ser Leu Ser Asp Thr Val Asn Lys Ser Asp
225                 230                 235                 240

Leu Asn Glu Asp Gly Thr Ile Asn Ile Asn Gly Lys Gly Asn Tyr Ser
                245                 250                 255

Ala Val Met Gly Asp Glu Leu Ile Val Lys Val Arg Asn Leu Asn Thr
            260                 265                 270

Asn Asn Val Gln Glu Tyr Val Ile Pro Val Asp Lys Lys Glu Lys Ser
        275                 280                 285

Asn Asp Ser Asn Ile Val Lys Tyr Arg Ser Leu Tyr Ile Lys Ala Pro
290                 295                 300

Gly Ile Lys Leu Glu His His His His His
305                 310                 315

<210> SEQ ID NO 15
<211> LENGTH: 315
<212> TYPE: PRT
<213> ORGANISM: Artificial Sequence
<220> FEATURE:
<223> OTHER INFORMATION: Recombinant mutation sequence

<400> SEQUENCE: 15

Met Lys Tyr Leu Leu Pro Thr Ala Ala Ala Gly Leu Leu Leu Leu Ala
1               5                   10                  15

Ala Gln Pro Ala Met Ala Met Gly Lys Ala Ser Tyr Asp Asn Val Asp
            20                  25                  30

Thr Leu Ile Glu Lys Gly Arg Tyr Asn Thr Lys Tyr Asn Tyr Leu Lys
        35                  40                  45

Arg Met Glu Lys Tyr Ala Pro Asn Ala Met Ala Tyr Phe Asp Lys Val
50                  55                  60

Thr Ile Asn Pro Gln Gly Asn Asp Phe Tyr Ile Asn Asn Pro Lys Val
65                  70                  75                  80

Glu Leu Asp Gly Glu Pro Ser Met Asn Tyr Leu Glu Asp Val Tyr Val
                85                  90                  95

Gly Lys Ala Leu Leu Thr Asn Asp Thr Gln Gln Glu Lys Leu Lys
            100                 105                 110

Ser Gln Ser Phe Thr Cys Lys Asn Thr Asp Thr Val Thr Ala Thr Thr
        115                 120                 125

Thr His Thr Val Gly Thr Ser Ile Gln Ala Thr Ala Lys Phe Thr Val
    130                 135                 140

Pro Phe Asn Glu Thr Gly Val Ser Leu Thr Thr Ser Tyr Ser Phe Ala
145                 150                 155                 160

Asn Thr Asn Thr Asn Thr Asn Ser Lys Glu Ile Thr His Asn Val Pro
                165                 170                 175

Ser Gln Asp Ile Leu Val Pro Ala Asn Thr Thr Val Glu Val Ile Ala
            180                 185                 190

Tyr Leu Lys Lys Val Asn Val Lys Gly Asn Val Lys Leu Val Gly Gln
        195                 200                 205

Val Ser Gly Ser Glu Trp Gly Glu Ile Pro Ser Ala Leu Ala Phe Pro
    210                 215                 220

Arg Asp Gly Tyr Lys Phe Ser Leu Ser Asp Thr Val Asn Lys Ser Asp
225                 230                 235                 240

Leu Asn Glu Asp Gly Thr Ile Asn Ile Asn Gly Lys Gly Asn Tyr Ser
                245                 250                 255
```

```
Ala Val Met Gly Asp Glu Leu Ile Val Lys Val Arg Asn Leu Asn Thr
            260                 265                 270

Asn Asn Val Gln Glu Tyr Val Ile Pro Val Asp Lys Lys Glu Lys Ser
        275                 280                 285

Asn Asp Ser Asn Ile Val Lys Tyr Arg Ser Leu Tyr Ile Lys Ala Pro
    290                 295                 300

Gly Ile Lys Leu Glu His His His His His
305                 310             315

<210> SEQ ID NO 16
<211> LENGTH: 315
<212> TYPE: PRT
<213> ORGANISM: Artificial Sequence
<220> FEATURE:
<223> OTHER INFORMATION: Recombinant mutation sequence

<400> SEQUENCE: 16

Met Lys Tyr Leu Leu Pro Thr Ala Ala Ala Gly Leu Leu Leu Leu Ala
1               5                   10                  15

Ala Gln Pro Ala Met Ala Met Gly Lys Ala Ser Tyr Asp Asn Val Asp
            20                  25                  30

Thr Leu Ile Glu Lys Gly Arg Tyr Asn Thr Lys Tyr Asn Tyr Leu Lys
        35                  40                  45

Arg Met Glu Lys Tyr Tyr Pro Asn Ala Met Ala Tyr Phe Asp Lys Val
50                  55                  60

Thr Ile Asn Pro Gln Gly Asn Asp Phe Tyr Ile Asn Asn Pro Lys Val
65                  70                  75                  80

Glu Leu Asp Gly Glu Pro Ser Met Asn Tyr Leu Glu Asp Val Tyr Val
                85                  90                  95

Gly Lys Ala Leu Leu Thr Asn Asp Thr Gln Gln Glu Gln Lys Leu Lys
            100                 105                 110

Ser Gln Ser Phe Thr Cys Lys Asn Thr Asp Thr Val Thr Ala Thr Thr
        115                 120                 125

Thr His Thr Val Gly Thr Ser Ile Gln Ala Thr Ala Lys Phe Thr Val
    130                 135                 140

Pro Phe Asn Glu Thr Gly Val Ser Leu Thr Thr Ser Tyr Ser Phe Ala
145                 150                 155                 160

Asn Thr Asn Thr Asn Thr Asn Ser Lys Glu Ile Thr Ala Asn Val Pro
                165                 170                 175

Ser Gln Asp Ile Leu Val Pro Ala Asn Thr Thr Val Glu Val Ile Ala
            180                 185                 190

Tyr Leu Lys Lys Val Asn Val Lys Gly Asn Val Lys Leu Val Gly Gln
        195                 200                 205

Val Ser Gly Ser Glu Trp Gly Glu Ile Pro Ser Tyr Leu Ala Phe Pro
    210                 215                 220

Arg Asp Gly Tyr Lys Phe Ser Leu Ser Asp Thr Val Asn Lys Ser Asp
225                 230                 235                 240

Leu Asn Glu Asp Gly Thr Ile Asn Ile Asn Gly Lys Gly Asn Tyr Ser
                245                 250                 255

Ala Val Met Gly Asp Glu Leu Ile Val Lys Val Arg Asn Leu Asn Thr
            260                 265                 270

Asn Asn Val Gln Glu Tyr Val Ile Pro Val Asp Lys Lys Glu Lys Ser
        275                 280                 285

Asn Asp Ser Asn Ile Val Lys Tyr Arg Ser Leu Tyr Ile Lys Ala Pro
    290                 295                 300
```

```
Gly Ile Lys Leu Glu His His His His His
305                 310                 315

<210> SEQ ID NO 17
<211> LENGTH: 315
<212> TYPE: PRT
<213> ORGANISM: Artificial Sequence
<220> FEATURE:
<223> OTHER INFORMATION: Recombinant mutation sequence

<400> SEQUENCE: 17

Met Lys Tyr Leu Leu Pro Thr Ala Ala Ala Gly Leu Leu Leu Leu Ala
1               5                   10                  15

Ala Gln Pro Ala Met Ala Met Gly Lys Ala Ser Tyr Asp Asn Val Asp
            20                  25                  30

Thr Leu Ile Glu Lys Gly Arg Tyr Asn Thr Lys Tyr Asn Tyr Leu Lys
        35                  40                  45

Arg Met Glu Lys Tyr Ala Pro Asn Ala Met Ala Tyr Phe Asp Lys Val
50                  55                  60

Thr Ile Asn Pro Gln Gly Asn Asp Phe Tyr Ile Asn Asn Pro Lys Val
65                  70                  75                  80

Glu Leu Asp Gly Glu Pro Ser Met Asn Tyr Leu Glu Asp Val Tyr Val
                85                  90                  95

Gly Lys Ala Leu Leu Thr Asn Asp Thr Gln Gln Glu Gln Lys Leu Lys
            100                 105                 110

Ser Gln Ser Phe Thr Cys Lys Asn Thr Asp Thr Val Thr Ala Thr Thr
        115                 120                 125

Thr His Thr Val Gly Thr Ser Ile Gln Ala Thr Ala Lys Phe Thr Val
130                 135                 140

Pro Phe Asn Glu Thr Gly Val Ser Leu Thr Thr Ser Tyr Ser Phe Ala
145                 150                 155                 160

Asn Thr Asn Thr Asn Thr Asn Ser Lys Glu Ile Thr Ala Asn Val Pro
                165                 170                 175

Ser Gln Asp Ile Leu Val Pro Ala Asn Thr Thr Val Glu Val Ile Ala
            180                 185                 190

Tyr Leu Lys Lys Val Asn Val Lys Gly Asn Val Lys Leu Val Gly Gln
        195                 200                 205

Val Ser Gly Ser Glu Trp Gly Glu Ile Pro Ser Tyr Leu Ala Phe Pro
210                 215                 220

Arg Asp Gly Tyr Lys Phe Ser Leu Ser Asp Thr Val Asn Lys Ser Asp
225                 230                 235                 240

Leu Asn Glu Asp Gly Thr Ile Asn Ile Asn Gly Lys Gly Asn Tyr Ser
                245                 250                 255

Ala Val Met Gly Asp Glu Leu Ile Val Lys Val Arg Asn Leu Asn Thr
            260                 265                 270

Asn Asn Val Gln Glu Tyr Val Ile Pro Val Asp Lys Lys Glu Lys Ser
        275                 280                 285

Asn Asp Ser Asn Ile Val Lys Tyr Arg Ser Leu Tyr Ile Lys Ala Pro
290                 295                 300

Gly Ile Lys Leu Glu His His His His His
305                 310                 315

<210> SEQ ID NO 18
<211> LENGTH: 315
<212> TYPE: PRT
<213> ORGANISM: Artificial Sequence
<220> FEATURE:
```

-continued

<223> OTHER INFORMATION: Recombinant mutation sequence

<400> SEQUENCE: 18

Met Lys Tyr Leu Leu Pro Thr Ala Ala Ala Gly Leu Leu Leu Leu Ala
1               5                   10                  15

Ala Gln Pro Ala Met Ala Met Gly Lys Ala Ser Tyr Asp Asn Val Asp
            20                  25                  30

Thr Leu Ile Glu Lys Gly Arg Tyr Asn Thr Lys Tyr Asn Tyr Leu Lys
        35                  40                  45

Arg Met Glu Lys Tyr Tyr Pro Asn Ala Met Ala Tyr Phe Asp Lys Val
    50                  55                  60

Thr Ile Asn Pro Gln Gly Asn Asp Phe Tyr Ile Asn Asn Pro Lys Val
65                  70                  75                  80

Glu Leu Asp Gly Glu Pro Ser Met Asn Tyr Leu Glu Asp Val Tyr Val
                85                  90                  95

Gly Lys Ala Leu Leu Thr Asn Asp Thr Gln Gln Glu Gln Lys Leu Lys
            100                 105                 110

Ser Gln Ser Phe Thr Cys Lys Asn Thr Asp Thr Val Thr Ala Thr Thr
        115                 120                 125

Thr His Thr Val Gly Thr Ser Ile Gln Ala Thr Ala Lys Phe Thr Val
    130                 135                 140

Pro Phe Asn Glu Thr Gly Val Ser Leu Thr Thr Ser Tyr Ser Phe Ala
145                 150                 155                 160

Asn Thr Asn Thr Asn Thr Asn Ser Lys Glu Ile Thr Ala Asn Val Pro
                165                 170                 175

Ser Gln Asp Ile Leu Val Pro Ala Asn Thr Thr Val Glu Val Ile Ala
            180                 185                 190

Tyr Leu Lys Lys Val Asn Val Lys Gly Asn Val Lys Leu Val Gly Gln
        195                 200                 205

Val Ser Gly Ser Glu Trp Gly Glu Ile Pro Ser Ala Leu Ala Phe Pro
    210                 215                 220

Arg Asp Gly Tyr Lys Phe Ser Leu Ser Asp Thr Val Asn Lys Ser Asp
225                 230                 235                 240

Leu Asn Glu Asp Gly Thr Ile Asn Ile Asn Gly Lys Gly Asn Tyr Ser
                245                 250                 255

Ala Val Met Gly Asp Glu Leu Ile Val Lys Val Arg Asn Leu Asn Thr
            260                 265                 270

Asn Asn Val Gln Glu Tyr Val Ile Pro Val Asp Lys Lys Glu Lys Ser
        275                 280                 285

Asn Asp Ser Asn Ile Val Lys Tyr Arg Ser Leu Tyr Ile Lys Ala Pro
    290                 295                 300

Gly Ile Lys Leu Glu His His His His His
305                 310                 315

<210> SEQ ID NO 19
<211> LENGTH: 315
<212> TYPE: PRT
<213> ORGANISM: Artificial Sequence
<220> FEATURE:
<223> OTHER INFORMATION: Recombinant mutation sequence

<400> SEQUENCE: 19

Met Lys Tyr Leu Leu Pro Thr Ala Ala Ala Gly Leu Leu Leu Leu Ala
1               5                   10                  15

Ala Gln Pro Ala Met Ala Met Gly Lys Ala Ser Tyr Asp Asn Val Asp
            20                  25                  30

```
Thr Leu Ile Glu Lys Gly Arg Tyr Asn Thr Lys Tyr Asn Tyr Leu Lys
         35                  40                  45

Arg Met Glu Lys Tyr Ala Pro Asn Ala Met Ala Tyr Phe Asp Lys Val
 50                  55                  60

Thr Ile Asn Pro Gln Gly Asn Asp Phe Tyr Ile Asn Asn Pro Lys Val
 65                  70                  75                  80

Glu Leu Asp Gly Glu Pro Ser Met Asn Tyr Leu Glu Asp Val Tyr Val
                 85                  90                  95

Gly Lys Ala Leu Leu Thr Asn Asp Thr Gln Glu Gln Lys Leu Lys
                 100                 105                 110

Ser Gln Ser Phe Thr Cys Lys Asn Thr Asp Thr Val Thr Ala Thr Thr
             115                 120                 125

Thr His Thr Val Gly Thr Ser Ile Gln Ala Thr Ala Lys Phe Thr Val
         130                 135                 140

Pro Phe Asn Glu Thr Gly Val Ser Leu Thr Thr Ser Tyr Ser Phe Ala
145                 150                 155                 160

Asn Thr Asn Thr Asn Thr Asn Ser Lys Glu Ile Thr Ala Asn Val Pro
                 165                 170                 175

Ser Gln Asp Ile Leu Val Pro Ala Asn Thr Thr Val Glu Val Ile Ala
             180                 185                 190

Tyr Leu Lys Lys Val Asn Val Lys Gly Asn Val Lys Leu Val Gly Gln
         195                 200                 205

Val Ser Gly Ser Glu Trp Gly Glu Ile Pro Ser Ala Leu Ala Phe Pro
210                 215                 220

Arg Asp Gly Tyr Lys Phe Ser Leu Ser Asp Thr Val Asn Lys Ser Asp
225                 230                 235                 240

Leu Asn Glu Asp Gly Thr Ile Asn Ile Asn Gly Lys Gly Asn Tyr Ser
                 245                 250                 255

Ala Val Met Gly Asp Glu Leu Ile Val Lys Val Arg Asn Leu Asn Thr
             260                 265                 270

Asn Asn Val Gln Glu Tyr Val Ile Pro Val Asp Lys Lys Glu Lys Ser
         275                 280                 285

Asn Asp Ser Asn Ile Val Lys Tyr Arg Ser Leu Tyr Ile Lys Ala Pro
     290                 295                 300

Gly Ile Lys Leu Glu His His His His His
305                 310                 315

<210> SEQ ID NO 20
<211> LENGTH: 263
<212> TYPE: PRT
<213> ORGANISM: Artificial Sequence
<220> FEATURE:
<223> OTHER INFORMATION: Recombinant mutation sequence

<400> SEQUENCE: 20

Met Gly Lys Ala Ser Tyr Asp Asn Val Asp Thr Leu Ile Glu Lys Gly
 1               5                  10                  15

Arg Tyr Asn Thr Lys Tyr Asn Tyr Leu Lys Arg Met Glu Lys Tyr Ala
                 20                  25                  30

Pro Asn Ala Met Ala Tyr Phe Asp Lys Val Thr Ile Asn Pro Gln Gly
             35                  40                  45

Asn Asp Phe Tyr Ile Asn Asn Pro Lys Val Glu Leu Asp Gly Glu Pro
         50                  55                  60

Ser Met Asn Tyr Leu Glu Asp Val Tyr Val Gly Lys Ala Leu Leu Thr
 65                  70                  75                  80
```

```
Asn Asp Thr Gln Gln Glu Gln Lys Leu Lys Ser Gln Ser Phe Thr Cys
                85                  90                  95

Lys Asn Thr Asp Thr Val Thr Ala Thr Thr His Thr Val Gly Thr
            100                 105                 110

Ser Ile Gln Ala Thr Ala Lys Phe Thr Val Pro Phe Asn Glu Thr Gly
        115                 120                 125

Val Ser Leu Thr Thr Ser Tyr Ser Phe Ala Asn Thr Asn Thr Asn Thr
130                 135                 140

Asn Ser Lys Glu Ile Thr His Asn Val Pro Ser Gln Asp Ile Leu Val
145                 150                 155                 160

Pro Ala Asn Thr Thr Val Glu Val Ile Ala Tyr Leu Lys Lys Val Asn
                165                 170                 175

Val Lys Gly Asn Val Lys Leu Val Gly Gln Val Ser Gly Ser Glu Trp
            180                 185                 190

Gly Glu Ile Pro Ser Tyr Leu Ala Phe Pro Arg Asp Gly Tyr Lys Phe
        195                 200                 205

Ser Leu Ser Asp Thr Val Asn Lys Ser Asp Leu Asn Glu Asp Gly Thr
        210                 215                 220

Ile Asn Ile Asn Gly Lys Gly Asn Tyr Ser Ala Val Met Gly Asp Glu
225                 230                 235                 240

Leu Ile Val Lys Val Arg Asn Leu Asn Thr Asn Asn Val Gln Glu Tyr
                245                 250                 255

Val Ile Pro Val Asp Lys Lys
            260

<210> SEQ ID NO 21
<211> LENGTH: 263
<212> TYPE: PRT
<213> ORGANISM: Artificial Sequence
<220> FEATURE:
<223> OTHER INFORMATION: Recombinant mutation sequence

<400> SEQUENCE: 21

Met Gly Lys Ala Ser Tyr Asp Asn Val Asp Thr Leu Ile Glu Lys Gly
1               5                   10                  15

Arg Tyr Asn Thr Lys Tyr Asn Tyr Leu Lys Arg Met Glu Lys Tyr Tyr
            20                  25                  30

Pro Asn Ala Met Ala Tyr Phe Asp Lys Val Thr Ile Asn Pro Gln Gly
        35                  40                  45

Asn Asp Phe Tyr Ile Asn Asn Pro Lys Val Glu Leu Asp Gly Glu Pro
    50                  55                  60

Ser Met Asn Tyr Leu Glu Asp Val Tyr Val Gly Lys Ala Leu Leu Thr
65                  70                  75                  80

Asn Asp Thr Gln Gln Glu Gln Lys Leu Lys Ser Gln Ser Phe Thr Cys
                85                  90                  95

Lys Asn Thr Asp Thr Val Thr Ala Thr Thr His Thr Val Gly Thr
            100                 105                 110

Ser Ile Gln Ala Thr Ala Lys Phe Thr Val Pro Phe Asn Glu Thr Gly
        115                 120                 125

Val Ser Leu Thr Thr Ser Tyr Ser Phe Ala Asn Thr Asn Thr Asn Thr
130                 135                 140

Asn Ser Lys Glu Ile Thr His Asn Val Pro Ser Gln Asp Ile Leu Val
145                 150                 155                 160

Pro Ala Asn Thr Thr Val Glu Val Ile Ala Tyr Leu Lys Lys Val Asn
                165                 170                 175
```

```
Val Lys Gly Asn Val Lys Leu Val Gly Gln Val Ser Gly Ser Glu Trp
            180                 185                 190

Gly Glu Ile Pro Ser Ala Leu Ala Phe Pro Arg Asp Gly Tyr Lys Phe
            195                 200                 205

Ser Leu Ser Asp Thr Val Asn Lys Ser Asp Leu Asn Glu Asp Gly Thr
    210                 215                 220

Ile Asn Ile Asn Gly Lys Gly Asn Tyr Ser Ala Val Met Gly Asp Glu
225                 230                 235                 240

Leu Ile Val Lys Val Arg Asn Leu Asn Thr Asn Asn Val Gln Glu Tyr
                245                 250                 255

Val Ile Pro Val Asp Lys Lys
            260

<210> SEQ ID NO 22
<211> LENGTH: 263
<212> TYPE: PRT
<213> ORGANISM: Artificial Sequence
<220> FEATURE:
<223> OTHER INFORMATION: Recombinant mutation sequence

<400> SEQUENCE: 22

Met Gly Lys Ala Ser Tyr Asp Asn Val Asp Thr Leu Ile Glu Lys Gly
1               5                   10                  15

Arg Tyr Asn Thr Lys Tyr Asn Tyr Leu Lys Arg Met Glu Lys Tyr Tyr
            20                  25                  30

Pro Asn Ala Met Ala Tyr Phe Asp Lys Val Thr Ile Asn Pro Gln Gly
            35                  40                  45

Asn Asp Phe Tyr Ile Asn Asn Pro Lys Val Glu Leu Asp Gly Glu Pro
    50                  55                  60

Ser Met Asn Tyr Leu Glu Asp Val Tyr Val Gly Lys Ala Leu Leu Thr
65                  70                  75                  80

Asn Asp Thr Gln Gln Glu Gln Lys Leu Lys Ser Gln Ser Phe Thr Cys
                85                  90                  95

Lys Asn Thr Asp Thr Val Thr Ala Thr Thr Thr His Thr Val Gly Thr
            100                 105                 110

Ser Ile Gln Ala Thr Ala Lys Phe Thr Val Pro Phe Asn Glu Thr Gly
            115                 120                 125

Val Ser Leu Thr Thr Ser Tyr Ser Phe Ala Asn Thr Asn Thr Asn Thr
    130                 135                 140

Asn Ser Lys Glu Ile Thr Ala Asn Val Pro Ser Gln Asp Ile Leu Val
145                 150                 155                 160

Pro Ala Asn Thr Thr Val Glu Val Ile Ala Tyr Leu Lys Lys Val Asn
                165                 170                 175

Val Lys Gly Asn Val Lys Leu Val Gly Gln Val Ser Gly Ser Glu Trp
            180                 185                 190

Gly Glu Ile Pro Ser Tyr Leu Ala Phe Pro Arg Asp Gly Tyr Lys Phe
            195                 200                 205

Ser Leu Ser Asp Thr Val Asn Lys Ser Asp Leu Asn Glu Asp Gly Thr
    210                 215                 220

Ile Asn Ile Asn Gly Lys Gly Asn Tyr Ser Ala Val Met Gly Asp Glu
225                 230                 235                 240

Leu Ile Val Lys Val Arg Asn Leu Asn Thr Asn Asn Val Gln Glu Tyr
                245                 250                 255

Val Ile Pro Val Asp Lys Lys
            260
```

<210> SEQ ID NO 23
<211> LENGTH: 263
<212> TYPE: PRT
<213> ORGANISM: Artificial Sequence
<220> FEATURE:
<223> OTHER INFORMATION: Recombinant mutation sequence

<400> SEQUENCE: 23

```
Met Gly Lys Ala Ser Tyr Asp Asn Val Asp Thr Leu Ile Glu Lys Gly
1               5                   10                  15

Arg Tyr Asn Thr Lys Tyr Asn Tyr Leu Lys Arg Met Glu Lys Tyr Ala
            20                  25                  30

Pro Asn Ala Met Ala Tyr Phe Asp Lys Val Thr Ile Asn Pro Gln Gly
        35                  40                  45

Asn Asp Phe Tyr Ile Asn Pro Lys Val Glu Leu Asp Gly Glu Pro
    50                  55                  60

Ser Met Asn Tyr Leu Glu Asp Val Tyr Val Gly Lys Ala Leu Leu Thr
65                  70                  75                  80

Asn Asp Thr Gln Gln Glu Gln Lys Leu Lys Ser Gln Ser Phe Thr Cys
                85                  90                  95

Lys Asn Thr Asp Thr Val Thr Ala Thr Thr His Thr Val Gly Thr
            100                 105                 110

Ser Ile Gln Ala Thr Ala Lys Phe Thr Val Pro Phe Asn Glu Thr Gly
        115                 120                 125

Val Ser Leu Thr Thr Ser Tyr Ser Phe Ala Asn Thr Asn Thr Asn Thr
    130                 135                 140

Asn Ser Lys Glu Ile Thr Ala Asn Val Pro Ser Gln Asp Ile Leu Val
145                 150                 155                 160

Pro Ala Asn Thr Thr Val Glu Val Ile Ala Tyr Leu Lys Lys Val Asn
                165                 170                 175

Val Lys Gly Asn Val Lys Leu Val Gly Gln Val Ser Gly Ser Glu Trp
            180                 185                 190

Gly Glu Ile Pro Ser Tyr Leu Ala Phe Pro Arg Asp Gly Tyr Lys Phe
        195                 200                 205

Ser Leu Ser Asp Thr Val Asn Lys Ser Asp Leu Asn Glu Asp Gly Thr
    210                 215                 220

Ile Asn Ile Asn Gly Lys Gly Asn Tyr Ser Ala Val Met Gly Asp Glu
225                 230                 235                 240

Leu Ile Val Lys Val Arg Asn Leu Asn Thr Asn Asn Val Gln Glu Tyr
                245                 250                 255

Val Ile Pro Val Asp Lys Lys
            260
```

<210> SEQ ID NO 24
<211> LENGTH: 263
<212> TYPE: PRT
<213> ORGANISM: Artificial Sequence
<220> FEATURE:
<223> OTHER INFORMATION: Recombinant mutation sequence

<400> SEQUENCE: 24

```
Met Gly Lys Ala Ser Tyr Asp Asn Val Asp Thr Leu Ile Glu Lys Gly
1               5                   10                  15

Arg Tyr Asn Thr Lys Tyr Asn Tyr Leu Lys Arg Met Glu Lys Tyr Tyr
            20                  25                  30

Pro Asn Ala Met Ala Tyr Phe Asp Lys Val Thr Ile Asn Pro Gln Gly
```

-continued

```
                35                  40                  45
Asn Asp Phe Tyr Ile Asn Asn Pro Lys Val Glu Leu Asp Gly Glu Pro
 50                  55                  60

Ser Met Asn Tyr Leu Glu Asp Val Tyr Val Gly Lys Ala Leu Leu Thr
 65                  70                  75                  80

Asn Asp Thr Gln Gln Glu Gln Lys Leu Lys Ser Gln Ser Phe Thr Cys
                 85                  90                  95

Lys Asn Thr Asp Thr Val Thr Ala Thr Thr Thr His Thr Val Gly Thr
                100                 105                 110

Ser Ile Gln Ala Thr Ala Lys Phe Thr Val Pro Phe Asn Glu Thr Gly
                115                 120                 125

Val Ser Leu Thr Thr Ser Tyr Ser Phe Ala Asn Thr Asn Thr Asn Thr
            130                 135                 140

Asn Ser Lys Glu Ile Thr Ala Asn Val Pro Ser Gln Asp Ile Leu Val
145                 150                 155                 160

Pro Ala Asn Thr Thr Val Glu Val Ile Ala Tyr Leu Lys Lys Val Asn
                165                 170                 175

Val Lys Gly Asn Val Lys Leu Val Gly Gln Val Ser Gly Ser Glu Trp
                180                 185                 190

Gly Glu Ile Pro Ser Ala Leu Ala Phe Pro Arg Asp Gly Tyr Lys Phe
            195                 200                 205

Ser Leu Ser Asp Thr Val Asn Lys Ser Asp Leu Asn Glu Asp Gly Thr
 210                 215                 220

Ile Asn Ile Asn Gly Lys Gly Asn Tyr Ser Ala Val Met Gly Asp Glu
225                 230                 235                 240

Leu Ile Val Lys Val Arg Asn Leu Asn Thr Asn Asn Val Gln Glu Tyr
                245                 250                 255

Val Ile Pro Val Asp Lys Lys
            260

<210> SEQ ID NO 25
<211> LENGTH: 263
<212> TYPE: PRT
<213> ORGANISM: Artificial Sequence
<220> FEATURE:
<223> OTHER INFORMATION: Recombinant mutation sequence

<400> SEQUENCE: 25

Met Gly Lys Ala Ser Tyr Asp Asn Val Asp Thr Leu Ile Glu Lys Gly
 1               5                  10                  15

Arg Tyr Asn Thr Lys Tyr Asn Tyr Leu Lys Arg Met Glu Lys Tyr Ala
                20                  25                  30

Pro Asn Ala Met Ala Tyr Phe Asp Lys Val Thr Ile Asn Pro Gln Gly
            35                  40                  45

Asn Asp Phe Tyr Ile Asn Asn Pro Lys Val Glu Leu Asp Gly Glu Pro
 50                  55                  60

Ser Met Asn Tyr Leu Glu Asp Val Tyr Val Gly Lys Ala Leu Leu Thr
 65                  70                  75                  80

Asn Asp Thr Gln Gln Glu Gln Lys Leu Lys Ser Gln Ser Phe Thr Cys
                 85                  90                  95

Lys Asn Thr Asp Thr Val Thr Ala Thr Thr Thr His Thr Val Gly Thr
                100                 105                 110

Ser Ile Gln Ala Thr Ala Lys Phe Thr Val Pro Phe Asn Glu Thr Gly
                115                 120                 125

Val Ser Leu Thr Thr Ser Tyr Ser Phe Ala Asn Thr Asn Thr Asn Thr
```

```
                130                 135                 140
Asn Ser Lys Glu Ile Thr Ala Asn Val Pro Ser Gln Asp Ile Leu Val
145                 150                 155                 160

Pro Ala Asn Thr Thr Val Glu Val Ile Ala Tyr Leu Lys Lys Val Asn
                165                 170                 175

Val Lys Gly Asn Val Lys Leu Val Gly Gln Val Ser Gly Ser Glu Trp
                180                 185                 190

Gly Glu Ile Pro Ser Ala Leu Ala Phe Pro Arg Asp Gly Tyr Lys Phe
                195                 200                 205

Ser Leu Ser Asp Thr Val Asn Lys Ser Asp Leu Asn Glu Asp Gly Thr
                210                 215                 220

Ile Asn Ile Asn Gly Lys Gly Asn Tyr Ser Ala Val Met Gly Asp Glu
225                 230                 235                 240

Leu Ile Val Lys Val Arg Asn Leu Asn Thr Asn Asn Val Gln Glu Tyr
                245                 250                 255

Val Ile Pro Val Asp Lys Lys
                260

<210> SEQ ID NO 26
<211> LENGTH: 283
<212> TYPE: PRT
<213> ORGANISM: Clostridium perfringens

<400> SEQUENCE: 26

Lys Ala Ser Tyr Asp Asn Val Asp Thr Leu Ile Glu Lys Gly Arg Tyr
1               5                   10                  15

Asn Thr Lys Tyr Asn Tyr Leu Lys Arg Met Glu Lys Tyr Tyr Pro Asn
                20                  25                  30

Ala Met Ala Tyr Phe Asp Lys Val Thr Ile Asn Pro Gln Gly Asn Asp
            35                  40                  45

Phe Tyr Ile Asn Asn Pro Lys Val Glu Leu Asp Gly Glu Pro Ser Met
    50                  55                  60

Asn Tyr Leu Glu Asp Val Tyr Val Gly Lys Ala Leu Leu Thr Asn Asp
65                  70                  75                  80

Thr Gln Gln Glu Gln Lys Leu Lys Ser Gln Ser Phe Thr Cys Lys Asn
                85                  90                  95

Thr Asp Thr Val Thr Ala Thr Thr Thr His Thr Val Gly Thr Ser Ile
                100                 105                 110

Gln Ala Thr Ala Lys Phe Thr Val Pro Phe Asn Glu Thr Gly Val Ser
            115                 120                 125

Leu Thr Thr Ser Tyr Ser Phe Ala Asn Thr Asn Thr Asn Thr Asn Ser
    130                 135                 140

Lys Glu Ile Thr His Asn Val Pro Ser Gln Asp Ile Leu Val Pro Ala
145                 150                 155                 160

Asn Thr Thr Val Glu Val Ile Ala Tyr Leu Lys Lys Val Asn Val Lys
                165                 170                 175

Gly Asn Val Lys Leu Val Gly Gln Val Ser Gly Ser Glu Trp Gly Glu
                180                 185                 190

Ile Pro Ser Tyr Leu Ala Phe Pro Arg Asp Gly Tyr Lys Phe Ser Leu
            195                 200                 205

Ser Asp Thr Val Asn Lys Ser Asp Leu Asn Glu Asp Gly Thr Ile Asn
    210                 215                 220

Ile Asn Gly Lys Gly Asn Tyr Ser Ala Val Met Gly Asp Glu Leu Ile
225                 230                 235                 240
```

Val Lys Val Arg Asn Leu Asn Thr Asn Asn Val Gln Glu Tyr Val Ile
            245                 250                 255

Pro Val Asp Lys Lys Glu Lys Ser Asn Asp Ser Asn Ile Val Lys Tyr
            260                 265                 270

Arg Ser Leu Ser Ile Lys Ala Pro Gly Ile Lys
            275                 280

<210> SEQ ID NO 27
<211> LENGTH: 283
<212> TYPE: PRT
<213> ORGANISM: Artificial Sequence
<220> FEATURE:
<223> OTHER INFORMATION: Mutation sequence

<400> SEQUENCE: 27

Lys Ala Ser Tyr Asp Asn Val Asp Thr Leu Ile Glu Lys Gly Arg Tyr
1               5                   10                  15

Asn Thr Lys Tyr Asn Tyr Leu Lys Arg Met Glu Lys Tyr Tyr Pro Asn
            20                  25                  30

Ala Met Ala Tyr Phe Asp Lys Val Thr Ile Asn Pro Gln Gly Asn Asp
        35                  40                  45

Phe Tyr Ile Asn Asn Pro Lys Val Glu Leu Asp Gly Glu Pro Ser Met
    50                  55                  60

Asn Tyr Leu Glu Asp Val Tyr Val Gly Lys Ala Leu Leu Thr Asn Asp
65                  70                  75                  80

Thr Gln Gln Glu Gln Lys Leu Lys Ser Gln Ser Phe Thr Cys Lys Asn
                85                  90                  95

Thr Asp Thr Val Thr Ala Thr Thr His Thr Val Gly Thr Ser Ile
            100                 105                 110

Gln Ala Thr Ala Lys Phe Thr Val Pro Phe Asn Glu Thr Gly Val Ser
        115                 120                 125

Leu Thr Thr Ser Tyr Ser Phe Ala Asn Thr Asn Thr Asn Thr Asn Ser
    130                 135                 140

Lys Glu Ile Thr Ala Asn Val Pro Ser Gln Asp Ile Leu Val Pro Ala
145                 150                 155                 160

Asn Thr Thr Val Glu Val Ile Ala Tyr Leu Lys Lys Val Asn Val Lys
                165                 170                 175

Gly Asn Val Lys Leu Val Gly Gln Val Ser Gly Ser Glu Trp Gly Glu
            180                 185                 190

Ile Pro Ser Tyr Leu Ala Phe Pro Arg Asp Gly Tyr Lys Phe Ser Leu
        195                 200                 205

Ser Asp Thr Val Asn Lys Ser Asp Leu Asn Glu Asp Gly Thr Ile Asn
    210                 215                 220

Ile Asn Gly Lys Gly Asn Tyr Ser Ala Val Met Gly Asp Glu Leu Ile
225                 230                 235                 240

Val Lys Val Arg Asn Leu Asn Thr Asn Asn Val Gln Glu Tyr Val Ile
                245                 250                 255

Pro Val Asp Lys Lys Glu Lys Ser Asn Asp Ser Asn Ile Val Lys Tyr
            260                 265                 270

Arg Ser Leu Ser Ile Lys Ala Pro Gly Ile Lys
        275                 280

<210> SEQ ID NO 28
<211> LENGTH: 293
<212> TYPE: PRT
<213> ORGANISM: Artificial Sequence
<220> FEATURE:

```
<223> OTHER INFORMATION: Recombinant sequence

<400> SEQUENCE: 28

Met Gly Lys Ala Ser Tyr Asp Asn Val Asp Thr Leu Ile Glu Lys Gly
 1               5                  10                  15

Arg Tyr Asn Thr Lys Tyr Asn Tyr Leu Lys Arg Met Glu Lys Tyr Tyr
                20                  25                  30

Pro Asn Ala Met Ala Tyr Phe Asp Lys Val Thr Ile Asn Pro Gln Gly
            35                  40                  45

Asn Asp Phe Tyr Ile Asn Asn Pro Lys Val Glu Leu Asp Gly Glu Pro
     50                  55                  60

Ser Met Asn Tyr Leu Glu Asp Val Tyr Val Gly Lys Ala Leu Leu Thr
 65                  70                  75                  80

Asn Asp Thr Gln Gln Glu Gln Lys Leu Lys Ser Gln Ser Phe Thr Cys
                85                  90                  95

Lys Asn Thr Asp Thr Val Thr Ala Thr Thr Thr His Thr Val Gly Thr
               100                 105                 110

Ser Ile Gln Ala Thr Ala Lys Phe Thr Val Pro Phe Asn Glu Thr Gly
            115                 120                 125

Val Ser Leu Thr Thr Ser Tyr Ser Phe Ala Asn Thr Asn Thr Asn Thr
    130                 135                 140

Asn Ser Lys Glu Ile Thr Ala Asn Val Pro Ser Gln Asp Ile Leu Val
145                 150                 155                 160

Pro Ala Asn Thr Thr Val Glu Val Ile Ala Tyr Leu Lys Lys Val Asn
                165                 170                 175

Val Lys Gly Asn Val Lys Leu Val Gly Gln Val Ser Gly Ser Glu Trp
            180                 185                 190

Gly Glu Ile Pro Ser Tyr Leu Ala Phe Pro Arg Asp Gly Tyr Lys Phe
        195                 200                 205

Ser Leu Ser Asp Thr Val Asn Lys Ser Asp Leu Asn Glu Asp Gly Thr
    210                 215                 220

Ile Asn Ile Asn Gly Lys Gly Asn Tyr Ser Ala Val Met Gly Asp Glu
225                 230                 235                 240

Leu Ile Val Lys Val Arg Asn Leu Asn Thr Asn Asn Val Gln Glu Tyr
                245                 250                 255

Val Ile Pro Val Asp Lys Lys Glu Lys Ser Asn Asp Ser Asn Ile Val
            260                 265                 270

Lys Tyr Arg Ser Leu Tyr Ile Lys Ala Pro Gly Ile Lys Leu Glu His
        275                 280                 285

His His His His
    290

<210> SEQ ID NO 29
<211> LENGTH: 293
<212> TYPE: PRT
<213> ORGANISM: Artificial Sequence
<220> FEATURE:
<223> OTHER INFORMATION: Recombinant mutation sequence

<400> SEQUENCE: 29

Met Gly Lys Ala Ser Tyr Asp Asn Val Asp Thr Leu Ile Glu Lys Gly
 1               5                  10                  15

Arg Tyr Asn Thr Lys Tyr Asn Tyr Leu Lys Arg Met Glu Lys Tyr Tyr
                20                  25                  30

Pro Asn Ala Met Ala Tyr Phe Asp Lys Val Thr Ile Asn Pro Gln Gly
            35                  40                  45
```

-continued

```
Asn Asp Phe Tyr Ile Asn Asn Pro Lys Val Glu Leu Asp Gly Glu Pro
         50                  55                  60

Ser Met Asn Tyr Leu Glu Asp Val Tyr Val Gly Lys Ala Leu Leu Thr
 65                  70                  75                  80

Asn Asp Thr Gln Gln Glu Gln Lys Leu Lys Ser Gln Ser Phe Thr Cys
                 85                  90                  95

Lys Asn Thr Asp Thr Val Thr Ala Thr Thr Thr His Thr Val Gly Thr
                100                 105                 110

Ser Ile Gln Ala Thr Ala Lys Phe Thr Val Pro Phe Asn Glu Thr Gly
            115                 120                 125

Val Ser Leu Thr Thr Ser Tyr Ser Phe Ala Asn Thr Asn Thr Asn Thr
        130                 135                 140

Asn Ser Lys Glu Ile Thr Ala Asn Val Pro Ser Gln Asp Ile Leu Val
145                 150                 155                 160

Pro Ala Asn Thr Thr Val Glu Val Ile Ala Tyr Leu Lys Lys Val Asn
                165                 170                 175

Val Lys Gly Asn Val Lys Leu Val Gly Gln Val Ser Gly Ser Glu Trp
                180                 185                 190

Gly Glu Ile Pro Ser Tyr Leu Ala Phe Pro Arg Asp Gly Tyr Lys Phe
            195                 200                 205

Ser Leu Ser Asp Thr Val Asn Lys Ser Asp Leu Asn Glu Asp Gly Thr
        210                 215                 220

Ile Asn Ile Asn Gly Lys Gly Asn Tyr Ser Ala Val Met Gly Asp Glu
225                 230                 235                 240

Leu Ile Val Lys Val Arg Asn Leu Asn Thr Asn Val Gln Glu Tyr
                245                 250                 255

Val Ile Pro Val Asp Lys Lys Glu Lys Ser Asn Asp Ser Asn Ile Val
                260                 265                 270

Lys Tyr Arg Ser Leu Tyr Ile Lys Ala Pro Gly Ile Lys Leu Glu His
            275                 280                 285

His His His His His
    290
```

<210> SEQ ID NO 30
<211> LENGTH: 35
<212> TYPE: DNA
<213> ORGANISM: Artificial Sequence
<220> FEATURE:
<223> OTHER INFORMATION: Amplification primer

<400> SEQUENCE: 30
ggaattccca tgggtaaagc ttcttatgat aatgt        35

<210> SEQ ID NO 31
<211> LENGTH: 29
<212> TYPE: DNA
<213> ORGANISM: Artificial Sequence
<220> FEATURE:
<223> OTHER INFORMATION: Amplification primer

<400> SEQUENCE: 31
attgccgctc gagtttatt cctggtgcc        29

<210> SEQ ID NO 32
<211> LENGTH: 13
<212> TYPE: PRT
<213> ORGANISM: Artificial Sequence
<220> FEATURE:

<223> OTHER INFORMATION: Protein fragment

<400> SEQUENCE: 32

Lys Glu Ile Ser Asn Thr Val Ser Asn Glu Met Ser Lys
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Protein fragment
<220> FEATURE:
<221> NAME/KEY: misc_feature
<222> LOCATION: (6)..(6)
<223> OTHER INFORMATION: Xaa can be any naturally occurring amino acid

<400> SEQUENCE: 33

Arg Met Glu Lys Tyr Xaa Pro Asn Ala Met
1               5                   10

<210> SEQ ID NO 34
<211> LENGTH: 20
<212> TYPE: PRT
<213> ORGANISM: Artificial Sequence
<220> FEATURE:
<223> OTHER INFORMATION: Protein fragment
<220> FEATURE:
<221> NAME/KEY: misc_feature
<222> LOCATION: (11)..(11)
<223> OTHER INFORMATION: Xaa can be any naturally occurring amino acid

<400> SEQUENCE: 34

Tyr Asn Tyr Leu Lys Arg Met Glu Lys Tyr Xaa Pro Asn Ala Met Ala
1               5                   10                  15

Tyr Phe Asp Lys
            20

<210> SEQ ID NO 35
<211> LENGTH: 10
<212> TYPE: PRT
<213> ORGANISM: Artificial Sequence
<220> FEATURE:
<223> OTHER INFORMATION: Protein fragment
<220> FEATURE:
<221> NAME/KEY: misc_feature
<222> LOCATION: (6)..(6)
<223> OTHER INFORMATION: Xaa can be any naturally occurring amino acid

<400> SEQUENCE: 35

Gly Glu Ile Pro Ser Xaa Leu Ala Phe Pro
1               5                   10

<210> SEQ ID NO 36
<211> LENGTH: 20
<212> TYPE: PRT
<213> ORGANISM: Artificial Sequence
<220> FEATURE:
<223> OTHER INFORMATION: Protein fragment
<220> FEATURE:
<221> NAME/KEY: misc_feature
<222> LOCATION: (11)..(11)
<223> OTHER INFORMATION: Xaa can be any naturally occurring amino acid

<400> SEQUENCE: 36

Ser Gly Ser Glu Trp Gly Glu Ile Pro Ser Xaa Leu Ala Phe Pro Arg
1               5                   10                  15

Asp Gly Tyr Lys

20

<210> SEQ ID NO 37
<211> LENGTH: 85
<212> TYPE: DNA
<213> ORGANISM: Artificial Sequence
<220> FEATURE:
<223> OTHER INFORMATION: Amplification primer

<400> SEQUENCE: 37
cttcttatga taatgtagat acattaattg agaaggaag agcgaataca aaatataatt    60
acttaaagag aatggaaaaa tatta                                        85

<210> SEQ ID NO 38
<211> LENGTH: 85
<212> TYPE: DNA
<213> ORGANISM: Artificial Sequence
<220> FEATURE:
<223> OTHER INFORMATION: Amplification primer

<400> SEQUENCE: 38
taatattttt ccattctctt taagtaatta tattttgtat tcgctcttcc tttctcaatt    60
aatgtatcta cattatcata agaag                                        85

<210> SEQ ID NO 39
<211> LENGTH: 81
<212> TYPE: DNA
<213> ORGANISM: Artificial Sequence
<220> FEATURE:
<223> OTHER INFORMATION: Amplification primer

<400> SEQUENCE: 39
gtagatacat taattgagaa aggaagatat aatacaaaag cgaattactt aaagagaatg    60 gaaaatatt atcctaatgc t                                             81

<210> SEQ ID NO 40
<211> LENGTH: 81
<212> TYPE: DNA
<213> ORGANISM: Artificial Sequence
<220> FEATURE:
<223> OTHER INFORMATION: Amplification primer

<400> SEQUENCE: 40
agcattagga taatattttt ccattctctt taagtaattc gcttttgtat tatatcttcc    60
tttctcaatt aatgtatcta c                                            81

<210> SEQ ID NO 41
<211> LENGTH: 80
<212> TYPE: DNA
<213> ORGANISM: Artificial Sequence
<220> FEATURE:
<223> OTHER INFORMATION: Amplification primer

<400> SEQUENCE: 41
aaaggaagat ataatacaaa atataattac ttaaagagaa tggaaaaagc gtatcctaat    60
gctatggcat attttgataa                                              80

<210> SEQ ID NO 42
<211> LENGTH: 80
<212> TYPE: DNA
<213> ORGANISM: Artificial Sequence
<220> FEATURE:
<223> OTHER INFORMATION: Amplification primer

<400> SEQUENCE: 42
ttatcaaaat atgccatagc attaggatac gcttttttcca ttctctttaa gtaattatat    60
tttgtattat atcttccttt                                                80

<210> SEQ ID NO 43
<211> LENGTH: 80
<212> TYPE: DNA
<213> ORGANISM: Artificial Sequence
<220> FEATURE:
<223> OTHER INFORMATION: Amplification primer

<400> SEQUENCE: 43
aaaggaagat ataatacaaa atataattac ttaaagagaa tggaaaaata tgcgcctaat    60
gctatggcat attttgataa                                                80

<210> SEQ ID NO 44
<211> LENGTH: 80
<212> TYPE: DNA
<213> ORGANISM: Artificial Sequence
<220> FEATURE:
<223> OTHER INFORMATION: Amplification primer

<400> SEQUENCE: 44
ttatcaaaat atgccatagc attaggcgca tattttttcca ttctctttaa gtaattatat    60
tttgtattat atcttccttt                                                80

<210> SEQ ID NO 45
<211> LENGTH: 83
<212> TYPE: DNA
<213> ORGANISM: Artificial Sequence
<220> FEATURE:
<223> OTHER INFORMATION: Amplification primer

<400> SEQUENCE: 45
gaaaggaaga tataatacaa aatataatta cttaaagaga atggaaaaat atgcgcctaa    60
tgctatggca tattttgata agg                                            83

<210> SEQ ID NO 46
<211> LENGTH: 83
<212> TYPE: DNA
<213> ORGANISM: Artificial Sequence
<220> FEATURE:
<223> OTHER INFORMATION: Amplification primer

<400> SEQUENCE: 46
ccttatcaaa atatgccata gcattaggcg catattttc cattctcttt aagtaattat    60
attttgtatt atatcttcct ttc                                            83

<210> SEQ ID NO 47
<211> LENGTH: 67
<212> TYPE: DNA
<213> ORGANISM: Artificial Sequence
<220> FEATURE:
<223> OTHER INFORMATION: Amplification primer

<400> SEQUENCE: 47
gaatggaaaa atattatcct aatgctatgg cagcgtttga taaggttact ataaatccac    60
aaggaaa                                                              67

<210> SEQ ID NO 48

```
<211> LENGTH: 67
<212> TYPE: DNA
<213> ORGANISM: Artificial Sequence
<220> FEATURE:
<223> OTHER INFORMATION: Amplification primer

<400> SEQUENCE: 48
tttccttgtg gatttatagt aaccttatca aacgctgcca tagcattagg ataatatttt      60
tccattc                                                                67

<210> SEQ ID NO 49
<211> LENGTH: 49
<212> TYPE: DNA
<213> ORGANISM: Artificial Sequence
<220> FEATURE:
<223> OTHER INFORMATION: Amplification primer

<400> SEQUENCE: 49
gtgaatgggg agagatacct agtgcgttag cttttcctag ggatggtta                  49

<210> SEQ ID NO 50
<211> LENGTH: 49
<212> TYPE: DNA
<213> ORGANISM: Artificial Sequence
<220> FEATURE:
<223> OTHER INFORMATION: Amplification primer

<400> SEQUENCE: 50
taaccatccc taggaaaagc taacgcacta ggtatctctc cccattcac                  49

<210> SEQ ID NO 51
<211> LENGTH: 66
<212> TYPE: DNA
<213> ORGANISM: Artificial Sequence
<220> FEATURE:
<223> OTHER INFORMATION: Amplification primer

<400> SEQUENCE: 51
caaatacaaa tacaaatact aattcaaaag aaattactca taatgtccct tcacaagata      60
tactag                                                                 66

<210> SEQ ID NO 52
<211> LENGTH: 66
<212> TYPE: DNA
<213> ORGANISM: Artificial Sequence
<220> FEATURE:
<223> OTHER INFORMATION: Amplification primer

<400> SEQUENCE: 52
ctagtatatc ttgtgaaggg acattatgag taatttcttt tgaattagta tttgtatttg      60
tatttg                                                                 66

<210> SEQ ID NO 53
<211> LENGTH: 34
<212> TYPE: PRT
<213> ORGANISM: Artificial Sequence
<220> FEATURE:
<223> OTHER INFORMATION: Protein fragment

<400> SEQUENCE: 53

Met Lys Tyr Leu Leu Pro Thr Ala Ala Ala Gly Leu Leu Leu Leu Ala
1               5                   10                  15

Ala Gln Pro Ala Met Ala Met Gly Lys Ala Ser Tyr Asp Asn Val Asp
            20                  25                  30
```

Thr Leu

<210> SEQ ID NO 54
<211> LENGTH: 12
<212> TYPE: PRT
<213> ORGANISM: Artificial Sequence
<220> FEATURE:
<223> OTHER INFORMATION: Protein fragment

<400> SEQUENCE: 54

Glu Tyr Val Ile Pro Val Asp Lys Lys Glu Lys Ser
1               5                   10

<210> SEQ ID NO 55
<211> LENGTH: 987
<212> TYPE: DNA
<213> ORGANISM: Artificial Sequence
<220> FEATURE:
<223> OTHER INFORMATION: Synthetic encoding sequence

<400> SEQUENCE: 55

| | | | | | |
|---|---|---|---|---|---|
| atgaaaaaaa | atcttgtaaa | aagtttagca | atcgcatcag | cggtgatatc | catctattca | 60 |
| atagttaata | ttgtttcacc | aactaatgta | atagctaagg | aaatatctaa | tacagtatct | 120 |
| aatgaaatgt | ccaaaaaagc | ttcttatgat | aatgtagata | cattaattga | gaaaggaaga | 180 |
| tataatacaa | aatataatta | cttaaagaga | atggaaaaat | atgcgcctaa | tgctatggca | 240 |
| tattttgata | aggttactat | aaatccacaa | ggaaatgatt | tttatattaa | taatcctaaa | 300 |
| gttgaattag | atggagaacc | atcaatgaat | tatcttgaag | atgtttatgt | tggaaaagct | 360 |
| ctcttaacta | atgatactca | acaagaacaa | aaattaaaat | cacaatcatt | cacttgtaaa | 420 |
| aatactgata | cagtaactgc | aactactact | catactgtgg | gaacttcgat | acaagcaact | 480 |
| gctaagttta | ctgttccttt | taatgaaaca | ggagtatcat | taactactag | ttatagtttt | 540 |
| gcaaatacaa | atacaaatac | taattcaaaa | gaaattactc | ataatgtccc | ttcacaagat | 600 |
| atactagtac | cagctaatac | tactgtagaa | gtaatagcat | atttaaaaaa | agttaatgtt | 660 |
| aaaggaaatg | taaagttagt | aggacaagta | agtggaagtg | aatggggaga | gatacctagt | 720 |
| gcgttagctt | ttcctaggga | tggttataaa | tttagtttat | cggatacagt | aaataagagt | 780 |
| gatttaaatg | aagatggtac | tattaatatt | aatggaaaag | gaaattatag | tgcagttatg | 840 |
| ggagatgagt | taatagttaa | ggttagaaat | ttaaatacaa | ataatgtaca | agaatatgta | 900 |
| atacctgtag | ataaaaaaga | aaaagtaat | gattcaaata | tagtaaaata | taggagtctt | 960 |
| tatattaagg | caccaggaat | aaaataa | | | | 987 |

<210> SEQ ID NO 56
<211> LENGTH: 987
<212> TYPE: DNA
<213> ORGANISM: Artificial Sequence
<220> FEATURE:
<223> OTHER INFORMATION: Synthetic encoding sequence

<400> SEQUENCE: 56

| | | | | | |
|---|---|---|---|---|---|
| atgaaaaaaa | atcttgtaaa | aagtttagca | atcgcatcag | cggtgatatc | catctattca | 60 |
| atagttaata | ttgtttcacc | aactaatgta | atagctaagg | aaatatctaa | tacagtatct | 120 |
| aatgaaatgt | ccaaaaaagc | ttcttatgat | aatgtagata | cattaattga | gaaaggaaga | 180 |
| tataatacaa | aatataatta | cttaaagaga | atggaaaaat | atgcgcctaa | tgctatggca | 240 |
| tattttgata | aggttactat | aaatccacaa | ggaaatgatt | tttatattaa | taatcctaaa | 300 |

```
gttgaattag atggagaacc atcaatgaat tatcttgaag atgtttatgt tggaaaagct     360
ctcttaacta atgatactca acaagaacaa aaattaaaat cacaatcatt cacttgtaaa     420
aatactgata cagtaactgc aactactact catactgtgg aacttcgat acaagcaact      480 gctaagttta ctgttccttt taatgaaaca ggagtatcat taactactag ttatagtttt     540
gcaaatacaa atacaaatac taattcaaaa gaaattactg ctaatgtccc ttcacaagat     600
atactagtac cagctaatac tactgtagaa gtaatagcat atttaaaaaa agttaatgtt     660
aaaggaaatg taaagttagt aggacaagta agtggaagtg aatggggaga gatacctagt     720
gcgttagctt ttcctaggga tggttataaa tttagtttat cggatacagt aaataagagt     780
gatttaaatg aagatggtac tattaatatt aatggaaaag gaaattatag tgcagttatg     840
ggagatgagt taatagttaa ggttagaaat ttaaatacaa ataatgtaca agaatatgta     900
atacctgtag ataaaaaaga aaaagtaat gattcaaata tagtaaaata taggagtctt      960
tatattaagg caccaggaat aaaataa                                         987

<210> SEQ ID NO 57
<211> LENGTH: 789
<212> TYPE: DNA
<213> ORGANISM: Artificial Sequence
<220> FEATURE:
<223> OTHER INFORMATION: Synthetic encoding sequence

<400> SEQUENCE: 57
atgggtaaag cttcttatga taatgtagat acattaattg agaaaggaag atataataca      60
aaatataatt acttaaagag aatggaaaaa tatgcgccta atgctatggc atattttgat     120
aaggttacta taaatccaca aggaaatgat ttttatatta ataatcctaa agttgaatta     180
gatggagaac catcaatgaa ttatcttgaa gatgtttatg ttggaaaagc tctcttaact     240
aatgatactc aacaagaaca aaaattaaaa tcacaatcat tcacttgtaa aaatactgat     300
acagtaactg caactactac tcatactgtg gaacttcgat acaagcaac tgctaagttt      360 actgttcctt ttaatgaaac aggagtatca ttaactacta gttatagttt tgcaaataca     420
aatacaaata ctaattcaaa agaaattact cataatgtcc cttcacaaga tatactagta     480
ccagctaata ctactgtaga agtaatagca tatttaaaaa agttaatgt taaaggaaat      540 gtaaagttag taggacaagt aagtggaagt gaatggggag agatacctag tgcgttagct     600
tttcctaggg atggttataa atttagttta tcggatacag taaataagag tgatttaaat     660
gaagatggta ctattaatat taatggaaaa ggaaattata gtgcagttat gggagatgag     720
ttaatagtta aggttagaaa tttaaataca aataatgtac aagaatatgt aatacctgta     780
gataaaaaa                                                             789

<210> SEQ ID NO 58
<211> LENGTH: 949
<212> TYPE: DNA
<213> ORGANISM: Artificial Sequence
<220> FEATURE:
<223> OTHER INFORMATION: Synthetic encoding sequence

<400> SEQUENCE: 58
atgaaatacc tgctgccgac cgctgctgct ggtctgctgc tcctcgctgc ccagccggcg      60
atggccatgg gtaaagcttc ttatgataat gtagatacat taattgagaa aggaagatat     120
aatacaaaat ataattactt aaagagaatg gaaaaatatg cgcctaatgc tatggcatat     180
```

| | |
|---|---|
| tttgataagg ttactataaa tccacaagga aatgatttt atattaataa tcctaaagtt | 240 |
| gaattagatg gagaaccatc aatgaattat cttgaagatg tttatgttgg aaaagctctc | 300 |
| ttaactaatg atactcaaca agaacaaaaa ttaaaatcac aatcattcac ttgtaaaaat | 360 |
| actgatacag taactgcaac tactactcat actgtgggaa cttcgataca agcaactgct | 420 |
| aagtttactg ttccttttaa tgaaacagga gtatcattaa ctactagtta tagttttgca | 480 |
| aatacaaata caaatactaa ttcaaaagaa attactcata atgtcccttc acaagatata | 540 |
| ctagtaccag ctaatactac tgtagaagta atagcatatt taaaaaaagt taatgttaaa | 600 |
| ggaaatgtaa agttagtagg acaagtaagt ggaagtgaat ggggagagat acctagtgcg | 660 |
| ttagcttttc ctagggatgg ttataaattt agtttatcgg atacagtaaa taagagtgat | 720 |
| ttaaatgaag atggtactat taatattaat ggaaaaggaa attatagtgc agttatggga | 780 |
| gatgagttaa tagttaaggt tagaaattta aatacaaata atgtacaaga atatgtaata | 840 |
| cctgtagata aaaagaaaa aagtaatgat tcaaatatag taaaatatag gagtctttat | 900 |
| attaaggcac caggaataaa actcgagcac caccaccacc accactgag | 949 |

<210> SEQ ID NO 59
<211> LENGTH: 949
<212> TYPE: DNA
<213> ORGANISM: Artificial Sequence
<220> FEATURE:
<223> OTHER INFORMATION: Synthetic encoding sequence

<400> SEQUENCE: 59

| | |
|---|---|
| atgaaatacc tgctgccgac cgctgctgct ggtctgctgc tcctcgctgc ccagccggcg | 60 |
| atggccatgg gtaaagcttc ttatgataat gtagatacat taattgagaa aggaagatat | 120 |
| aatacaaaat ataattactt aaagagaatg gaaaatatg cgcctaatgc tatggcatat | 180 |
| tttgataagg ttactataaa tccacaagga atgatttt atattaataa tcctaaagtt | 240 |
| gaattagatg gagaaccatc aatgaattat cttgaagatg tttatgttgg aaaagctctc | 300 |
| ttaactaatg atactcaaca agaacaaaaa ttaaaatcac aatcattcac ttgtaaaaat | 360 |
| actgatacag taactgcaac tactactcat actgtgggaa cttcgataca agcaactgct | 420 |
| aagtttactg ttccttttaa tgaaacagga gtatcattaa ctactagtta tagttttgca | 480 |
| aatacaaata caaatactaa ttcaaaagaa attactgcta atgtcccttc acaagatata | 540 |
| ctagtaccag ctaatactac tgtagaagta atagcatatt taaaaaaagt taatgttaaa | 600 |
| ggaaatgtaa agttagtagg acaagtaagt ggaagtgaat ggggagagat acctagtgcg | 660 |
| ttagcttttc ctagggatgg ttataaattt agtttatcgg atacagtaaa taagagtgat | 720 |
| ttaaatgaag atggtactat taatattaat ggaaaaggaa attatagtgc agttatggga | 780 |
| gatgagttaa tagttaaggt tagaaattta aatacaaata atgtacaaga atatgtaata | 840 |
| cctgtagata aaaagaaaa aagtaatgat tcaaatatag taaaatatag gagtctttat | 900 |
| attaaggcac caggaataaa actcgagcac caccaccacc accactgag | 949 |

<210> SEQ ID NO 60
<211> LENGTH: 789
<212> TYPE: DNA
<213> ORGANISM: Artificial Sequence
<220> FEATURE:
<223> OTHER INFORMATION: Synthetic encoding sequence

<400> SEQUENCE: 60

| | |
|---|---|
| atgggtaaag cttcttatga taatgtagat acattaattg agaaaggaag atataataca | 60 |

```
aaatataatt acttaaagag aatggaaaaa tatgcgccta atgctatggc atattttgat      120
aaggttacta taaatccaca aggaaatgat ttttatatta ataatcctaa agttgaatta      180
gatggagaac catcaatgaa ttatcttgaa gatgtttatg ttggaaaagc tctcttaact      240
aatgatactc aacaagaaca aaaattaaaa tcacaatcat tcacttgtaa aaatactgat      300
acagtaactg caactactac tcatactgtg ggaacttcga tacaagcaac tgctaagttt      360
actgttcctt ttaatgaaac aggagtatca ttaactacta gttatagttt tgcaaataca      420
aatacaaata ctaattcaaa agaaattact gctaatgtcc cttcacaaga tatactagta      480
ccagctaata ctactgtaga agtaatagca tatttaaaaa aagttaatgt taaaggaaat      540
gtaaagttag taggacaagt aagtggaagt gaatggggag agatacctag tgcgttagct      600
tttcctaggg atggttataa atttagttta tcggatacag taaataagag tgatttaaat      660
gaagatggta ctattaatat taatggaaaa ggaaattata gtgcagttat gggagatgag      720
ttaatagtta aggttagaaa tttaaataca aataatgtac aagaatatgt aatacctgta      780
gataaaaaa                                                              789
```

UNITED STATES PATENT AND TRADEMARK OFFICE
CERTIFICATE OF CORRECTION

PATENT NO. : 9,573,981 B2  
APPLICATION NO. : 14/387809  
DATED : February 21, 2017  
INVENTOR(S) : Titball et al.

Page 1 of 1

It is certified that error appears in the above-identified patent and that said Letters Patent is hereby corrected as shown below:

In the Claims

In Column 88, in Claim 15, at Line 47, please delete "(New; Withdrawn)".

Signed and Sealed this
Fifth Day of September, 2017

Joseph Matal
*Performing the Functions and Duties of the
Under Secretary of Commerce for Intellectual Property and
Director of the United States Patent and Trademark Office*